United States Patent
Friedlander et al.

(10) Patent No.: US 11,298,409 B2
(45) Date of Patent: *Apr. 12, 2022

(54) MUTANT HUNTINGTIN-MEDIATED PROTEIN DYSFUNCTION

(71) Applicants: UNIVERSITY OF PITTSBURGH—OF THE COMMONWEALTH SYSTEM OF HIGHER EDUCATION, Pittsburgh, PA (US); WASHINGTON UNIVERSITY, St. Louis, MO (US)

(72) Inventors: Robert Friedlander, Pittsburgh, PA (US); Hiroko Yano, Richmond Heights, MO (US)

(73) Assignees: UNIVERSITY OF PITTSBURGH—OF THE COMMONWEALTH SYSTEM OF HIGHER EDUCATION, Pittsburgh, PA (US); WASHINGTON UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/689,523

(22) Filed: Nov. 20, 2019

(65) Prior Publication Data

US 2020/0085917 A1    Mar. 19, 2020

Related U.S. Application Data

(63) Continuation of application No. 15/295,538, filed on Oct. 17, 2016, now Pat. No. 10,525,108, which is a continuation of application No. PCT/US2015/026473, filed on Apr. 17, 2015.

(60) Provisional application No. 61/992,504, filed on May 13, 2014, provisional application No. 61/981,092, filed on Apr. 17, 2014.

(51) Int. Cl.
| | |
|---|---|
| *A61K 38/45* | (2006.01) |
| *C12N 9/12* | (2006.01) |
| *C12N 15/62* | (2006.01) |
| *A61K 38/17* | (2006.01) |

(52) U.S. Cl.
CPC .......... *A61K 38/45* (2013.01); *A61K 38/1709* (2013.01); *C12N 9/1205* (2013.01); *C12N 15/62* (2013.01); *C12Y 207/11001* (2013.01)

(58) Field of Classification Search
CPC .. A61K 38/45; A61K 38/1709; C12N 9/1205; C12N 15/62; C12Y 207/11001; A61P 25/28

See application file for complete search history.

(56) References Cited

PUBLICATIONS

U.S. Appl. No. 15/295,528 (US 2017/028034), filed Oct. 17, 2016 (Feb. 2, 2017).
U.S. Appl. No. 15/295,538, Aug. 21, 2019 Notice of Allowance.
U.S. Appl. No. 15/295,538, May 30, 2019 Response to Non-Final Office Action.
U.S. Appl. No. 15/295,538, Mar. 1, 2019 Non-Final Office Action.
U.S. Appl. No. 15/295,538, Sep. 11, 2018 Amendment and Request for Continued Examination (RCE).
U.S. Appl. No. 15/295,538, Jul. 11, 2018, Final Office Action.
U.S. Appl. No. 15/295,538, Mar. 27, 2018 Response to Non-Final Office Action.
U.S. Appl. No. 15/295,538, Dec. 12, 2017 Non-Final Office Action.
Acevedo-Torres et al., "Mitochondrial DNA damage is a hallmark of chemically induced and the R6/2 transgenic model of Huntington's disease," DNA Repair (Amst) 8(1):126-136 (2009).
Ahting et al., "Neurological phenotype and reduced lifespan in heterozygous Tim23 knockout mice, the first mouse model of defective mitochondrial import," Biochimica et Biophysica Acta 1787:371-376 (2009).
Altmann et al., "Role of Essential Genes in Mitochondrial Morphogenesis in *Saccharomyces cerevisiae*," Mol. Biol. Cell 16:5410-5417 (2005).
Atwal et al., "Kinase inhibitors modulate huntingtin cell localization and toxicity," Nature Chemical Biology, 7(7):453-460 (2011) with Suppl. information.
Baker et al., "Mitochondrial protein-import machinery: correlating structure with function," Trends in Cell Biol. 17(9):456-464 (2007).
Baranov et al., "Kinetic Model for Ca2+-induced Permeability Transition in Energized Liver Mitochondria Discriminates between Inhibitor Mechanisms," J. Biol. Chem. 283(2):665-676 (2008).
Bates, G., "Huntingtin aggregation and toxicity in Huntington's disease," Lancet 361:1642-1644 (2003).
Browne et al., "Oxidative damage and Metabolic Dysfunction in Huntington's Disease: Selective Vulnerability of the Basal Ganglia," Ann. Neurol. 41:646-653 (1997).
Browne et al., "The Energetics of Huntington's Disease," Neurochem. Res. 29(3):531-546 (2004).
Chacinska et al., "Importing Mitochondrial Proteins: Machineries and Mechanisms," Cell 138:628-644 (2009).
Choo et al., "Mutant huntingtin directly increases susceptibility of mitochondria to the calcium-induced permeability transition and cytochrome c release," Hum. Mol. Genet. 13(14):1407-1420 (2004).
Costa et al., "Mitochondrial fission and cristae disruption increase the response of cell models of Huntington's disease to apoptotic stimuli," EMBO Mol. Med. 2:490-503 (2010).
Costa et al., "Shaping the role of mitochondria in the pathogenesis of Huntington's disease," The EMBO Journal 31:1853-1864 (2012).
Cui et al., "Transcriptional Repression of PGC-1α by Mutant Huntingtin Leads to Mitochondrial Dysfunction and Neurodegeneration," Cell 127:59-69 (2006).
Damiano et al., "Mitochondria in Huntington's disease," Biochimica et Biophysica Acta 1802:52-61 (2010).

(Continued)

*Primary Examiner* — Kimberly Ballard
*Assistant Examiner* — Stacey N MacFarlane
(74) *Attorney, Agent, or Firm* — Baker Botts L.L.P.

(57) ABSTRACT

The present invention relates to methods of inhibiting neurodegeneration in a subject suffering from or genetically at risk and/or destined to develop Huntington's Disease comprising increasing, in neurons of the subject, the activity of the TIM23 mitochondrial protein import complex.

13 Claims, 32 Drawing Sheets

Figures 1A, 1B:
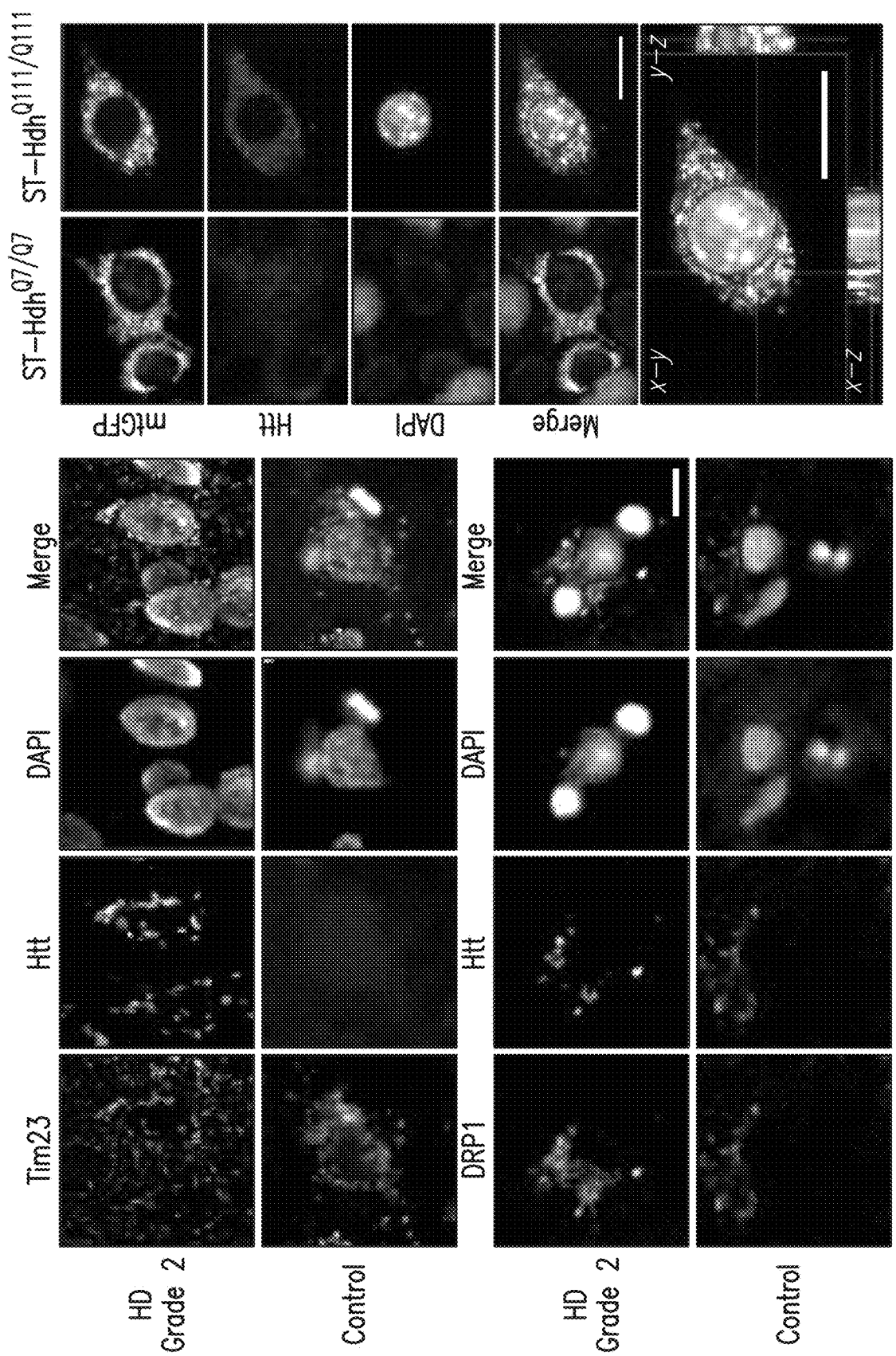

Specification includes a Sequence Listing.

(56) References Cited

PUBLICATIONS

Devi et al., "Accumulation of Amyloid Precursor Protein in the Mitochondrial Import Channels of Human Alzheimer's Disease Brain Is Associated with Mitochondrial Dysfunction," J. Neurosci. 26(35):9057-9068 (2006).
DiFiglia et al., "Aggregation of Huntingtin in Neuronal Intranuclear Inclusions and Dystrophic Neurites in Brain," Science 277:1990-1993 (1997).
Ehrlich et al., "ST14A Cells Have Properties of a Medium-Size Spiny Neuron," Exp. Neurol. 167:215-226 (2001).
Fulda et al., Nature Reviews, 9:477-464, Jun. 2010.
Gines et al., "Specific progressive cAMP reduction implicates energy deficit in presymptomatic Huntington's disease knock-in mice," Hum. Mol. Genet. 12(5):497-508 (2003).
Gu et al., "Mitochondrial Defect in Huntington's Disease Caudate Nucleus," Ann Neurol 39:385-389 (1996).
Gu et al., "Serines 13 and 16 Are Critical Determinants of Full-Length Human Mutant Huntingtin Induced Disease Pathogenesis in HD Mice," Neuron, 64(6):828-840 (2009) with Suppl. information.
Hersch et al., "Neuropathology and Pathophysiology of Huntington's Disease," Chapter 34 in Movement Disorders 3rd ed. (eds. Watts, R.L., Standaert, D.G. & Obeso, J.A.) 683-711 (McGraw-Hill, New York, 2012).
Humphries et al., "Dissection of the Mitochondrial Import and Assembly Pathway for Human Tom40," J. Biol. Chem. 280(12):11535-11543 (2005).
International Search Report dated Aug. 18, 2015 in International Application No. PCT/US2015/026473.
Johri et al., "Antioxidants in Huntington's Disease," Biochim. Biophys. Acta 1822(5):664-674 (2012).
Kim et al., "A Centrosomal Cdc20-APC Pathway Controls Dendrite Morphogenesis in Postmitotic Neurons," Cell 136:322-336 (2009).
Kim et al., "Mitochondrial loss, dysfunction and altered dynamics in Huntington's disease," Hum. Mol. Genet. 19(20):3919-3935 (2010).
Kristian, T., "Isolation of mitochondria from the CNS," Curr. Protoc. Neurosci., Chapter: Unit-7.22 (2010).
Li et al., "Amino-terminal fragments of mutant huntingtin show selective accumulation in striatal neurons and synaptic toxicity," Nat. Genet. 25:385-389 (2000).
Li et al., "ALS-linked mutant superoxide dismutase 1 (SOD1) alters mitochondrial protein composition and decreases protein import," PNAS 107(49):21146-21151 (2010).
Li et al., "Huntingtin Aggregate-Associated Axonal Degeneration is an Early Pathological Event in Huntington's Disease Mice," J. Neurosci. 21(21):8473-8481 (2001).
Liu et al., "Toxicity of Familial ALS-Linked SOD1 Mutants from Selective Recruitment to Spinal Mitochondria," Neuron 43:5-17 (2004).
MacKenzie et al., "Mitochondrial protein import and human health and disease," Biochimica et Biophysica Acta 1772:509-523 (2007).
Mangiarini et al., "Exon 1 of the HD Gene with an Expanded CAG Repeat Is Sufficient to Cause a Progressive Neurological Phenotype in Transgenic Mice," Cell 87:493-506 (1996).
Meisinger et al., "The Mitochondrial Morphology Protein Mdm10 Functions in Assembly of the Preprotein Translocase of the Outer Membrane," Dev. Cell 7:61-71 (2004).
Milnerwood et al., "Early synaptic pathophysiology in neurodegeneration: insights from Huntington's disease," Trends in Neurosciences 33(11):513-523 (2010).
Mochel et al., "Early Alterations of Brain Cellular Energy Homeostasis in Huntington Disease Models," J. Biol. Chem. 287(2):1361-1370 (2012).
Mochel et al., "Energy deficit in Huntington disease: why it matters," J. Clin. Invest. 121(2):493-499 (2011).
Ona et al., "Inhibition of caspase-1 slows disease progression in a mouse model of Huntington's disease," Nature 399:263-267 (1999).
Orr et al., "N-Terminal Mutant Huntingtin Associates with Mitochondria and Impairs Mitochondrial Trafficking," J. Neurosci. 28(11):2783-2792 (2008).
Panov et al., "Early mitochondrial calcium defects in Huntington's disease are a direct effect of polyglutamines," Nat. Neurosci. 5(8):731-736 (2002).
Reddy et al., "Mutant huntingtin, abnormal mitochondrial dynamics, defective axonal transport of mitochondria, and selective synaptic degeneration in Huntington's disease," Biochimica et Biophysica Acta 1822:101-110 (2012).
Reddy et al., "Abnormal mitochondrial dynamics and synaptic degeneration as early events in Alzheimer's disease: Implications to mitochondria-targeted antioxidant therapeutics," Biochimica et Biophysica Acta 1822:639-649 (2012).
Rockabrand et al., "The first 17 amino acids of Huntingtin modulate its sub-cellular localization, aggregation and effects on calcium homeostasis," Hum. Mol. Genet. 16(1):61-77 (2007).
Roesch et al., "Human deafness dystonia syndrome is caused by a defect in assembly of the DDP1/TIMM8a-TIMM13 complex," Hum. Mol. Genet. 11(5):477-486 (2002).
Shao et al., "Polyglutamine diseases: emerging concepts in pathogenesis and therapy," Hum. Mol. Genet. 16(2):R115-R123 (2007).
Shirendeb et al., "Abnormal mitochondrial dynamics, mitochondrial loss and mutant huntingtin oligomers in Huntington's disease: implications for selective neuronal damage," Human Molecular Genetics, 20(7):4438-1455 (2011).
Shirendeb et al., "Mutant huntingtin's interaction with mitochondrial protein Drp1 impairs mitochondrial biogenesis and causes defective axonal transport and synaptic degeneration in Huntington's disease," Hum. Mol. Genet. 21(2):406-420 (2012).
Song et al., "Mutant huntingtin binds the mitochondrial fission GTPase dynamin-related protein-1 and increases its enzymatic activity," Nat. Med. 17(3):377-382 (2011).
Steffan et al., "Post-Translational Modification of HTT Within Its First 17 Amino Acids Regulates Its Stability, Aggregation, Cellular Localization and Toxicity," Clinical Genetics, 76(Suppl. 1):5 (2009).
Terada et al., "Participation of the import receptor Tom20 in protein import into mammalian mitochondria: analyses in vitro and in cultured cells," FEBS Letters 403:309-312 (1997).
The Huntington's Disease Collaborative Research Group, "A Novel Gene Containing a Trinucleotide Repeat That Is Expanded and Unstable on Huntington's Disease Chromosomes," Cell 72:971-983 (1993).
Trettel et al., "Dominant phenotypes produced by the HD mutation in STHdhQ111 striatal cells," Hum. Mol. Genet. 9(19):2799-2809 (2000).
Vögtle et al., "Sensing Mitochondrial Homeostasis: the Protein Import Machinery Takes Control," Dev. Cell 23:234-236 (2012).
Wang et al., "Minocycline inhibits caspase-independent and -dependent mitochondrial cell death pathways in models of Huntington's disease," PNAS 100(18):10483-10487 (2003).
Weydt et al., "Thermoregulatory and metabolic defects in Huntington's disease transgenic mice implicate PGC-1α in Huntington's disease neurodegeneration," Cell Metab. 4:349-362 (2006).
Yano et al., "Identification and Functional Analysis of Human Tom22 for Protein Import into Mitochondria," Mol. Cell. Biol. 20(19):7205-7213 (2000).
Yano et al., "Inhibition of mitochondrial protein import by mutant huntingtin," Nature Neuroscience, 17(6):822-831 (2014).
Yu et al., "Mutant Huntingtin Causes Context-Dependent Neurodegeneration in Mice with Huntington's Disease," J. Neurosci. 23(6):2193-2202 (2003).
Zoghbi et al., "Glutamine Repeats and Neurodegeneration," Annu. Rev. Neurosci. 23:217-247 (2000).

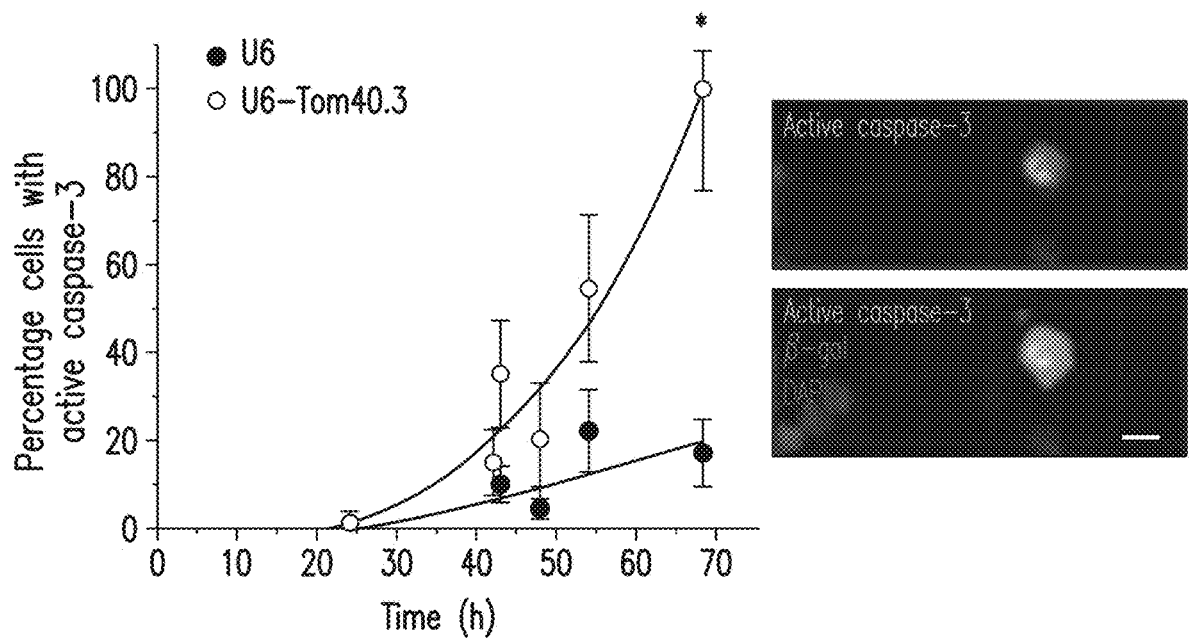
FIG. 5D
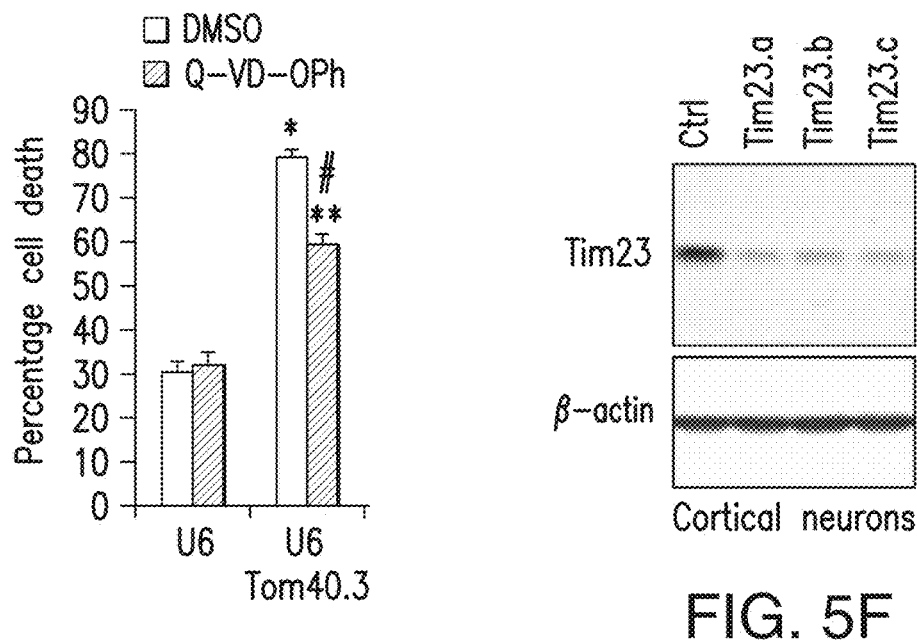
FIG. 5E
FIG. 5F

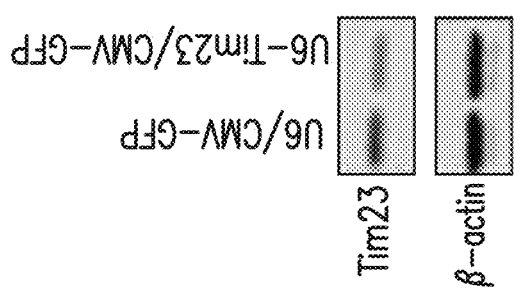
FIG. 5J
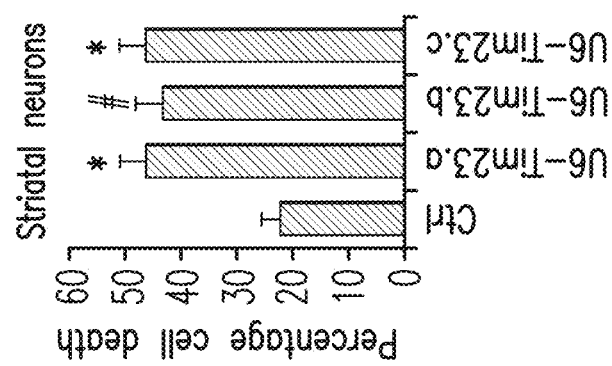
FIG. 5I
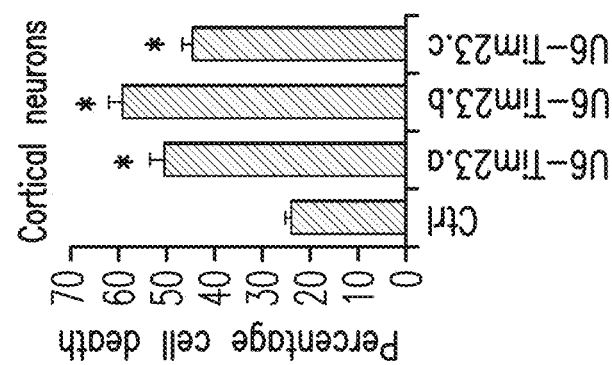

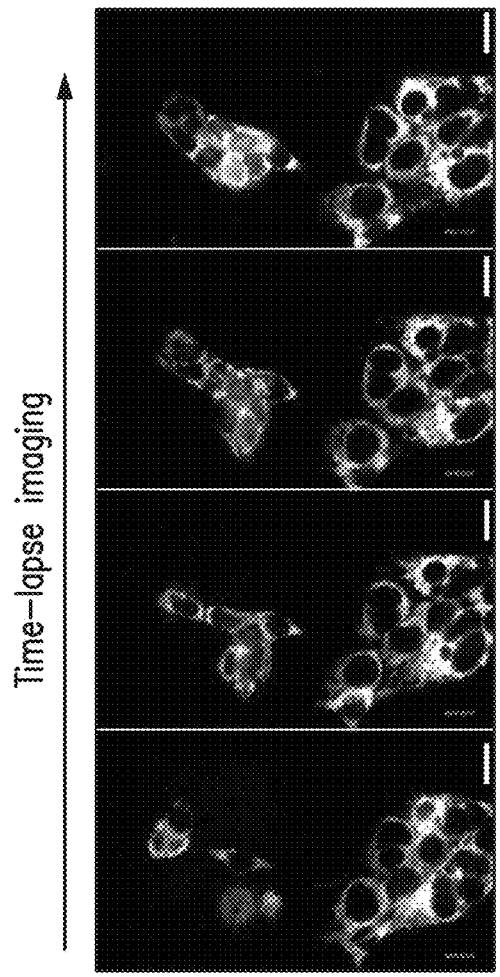
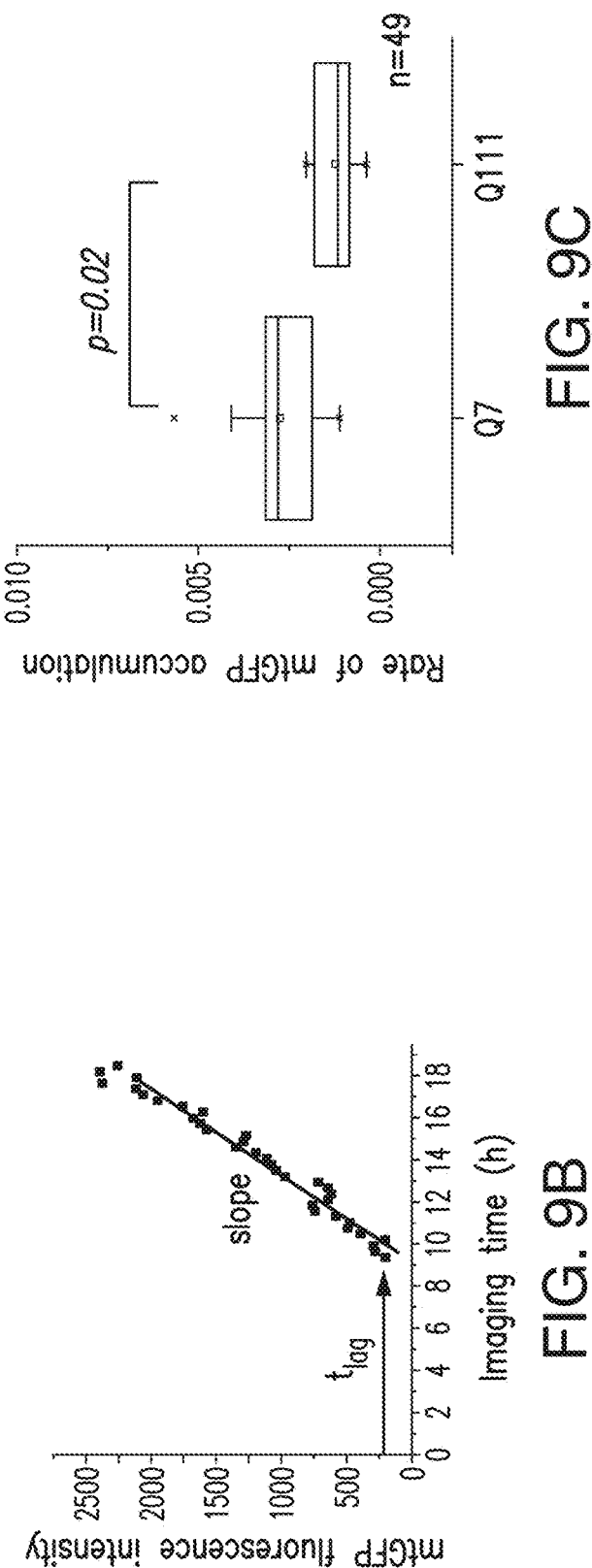
FIG. 9A
FIG. 9B
FIG. 9C

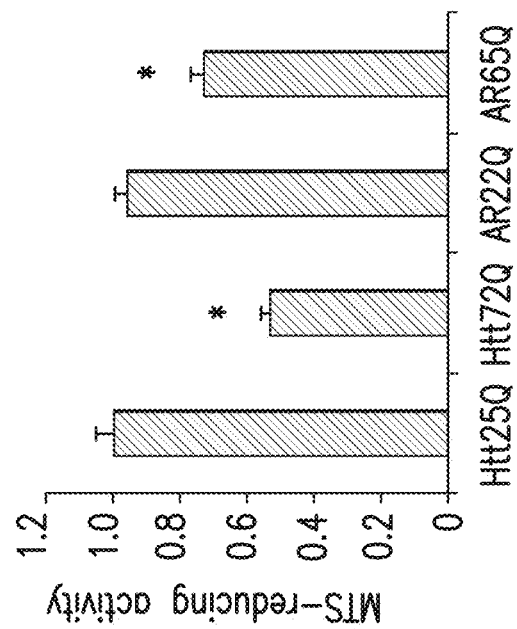
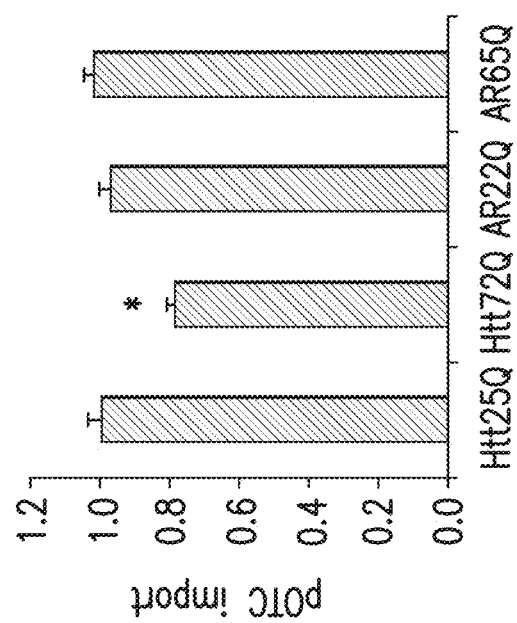
FIG. 12A
FIG. 12B

Figure 1C:
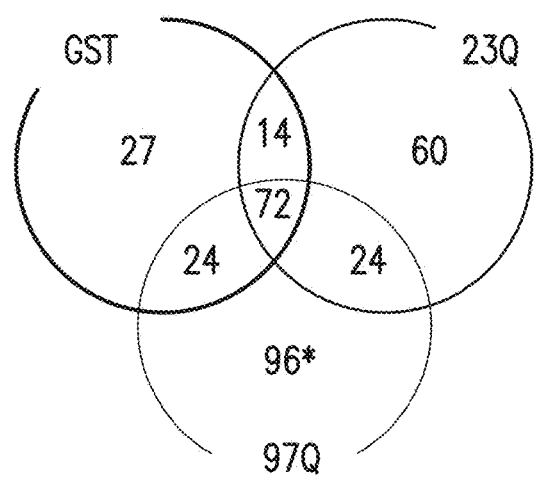
Figure 1D:
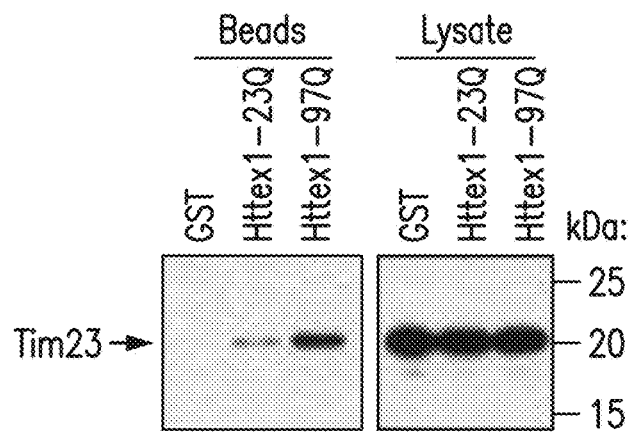
Figure 1E:
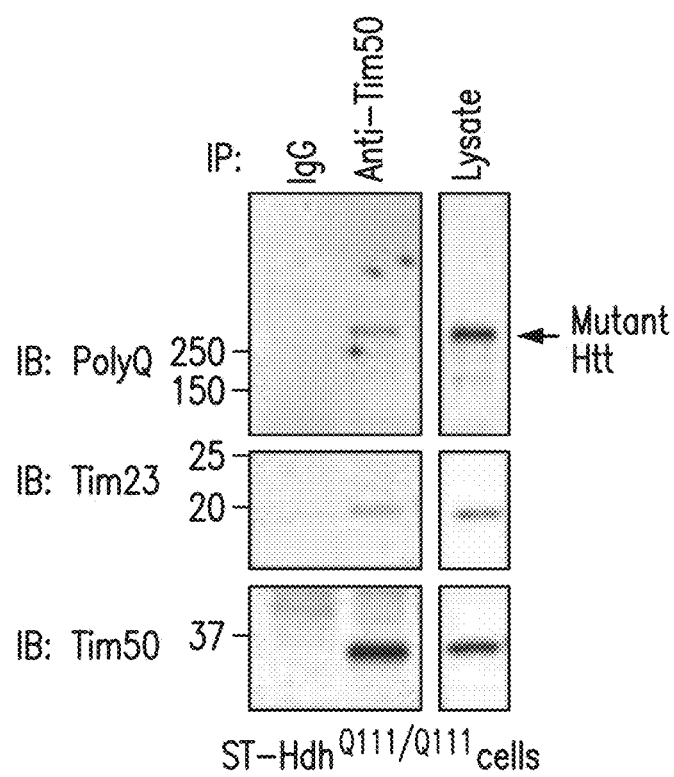
Figure 1F:
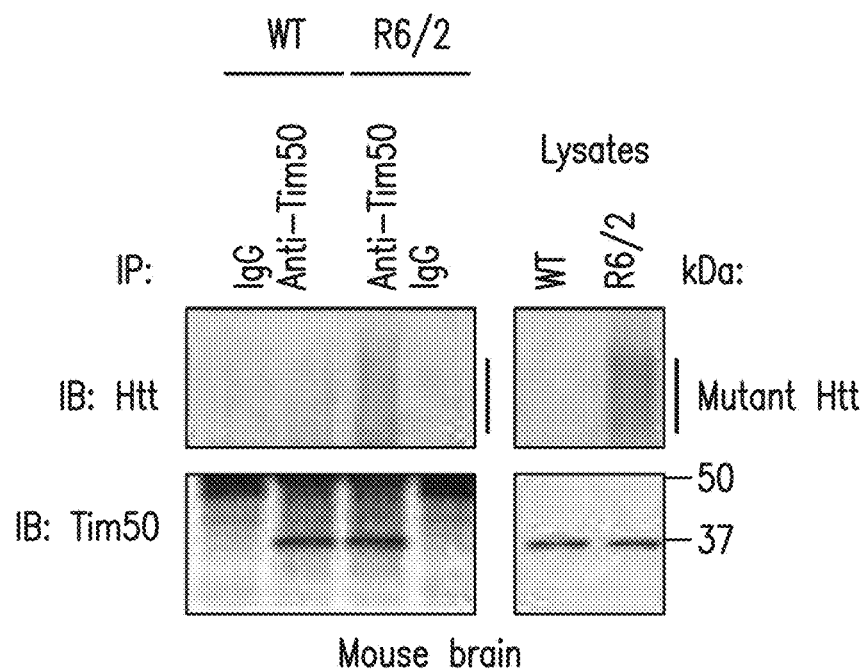
Figure 1G:
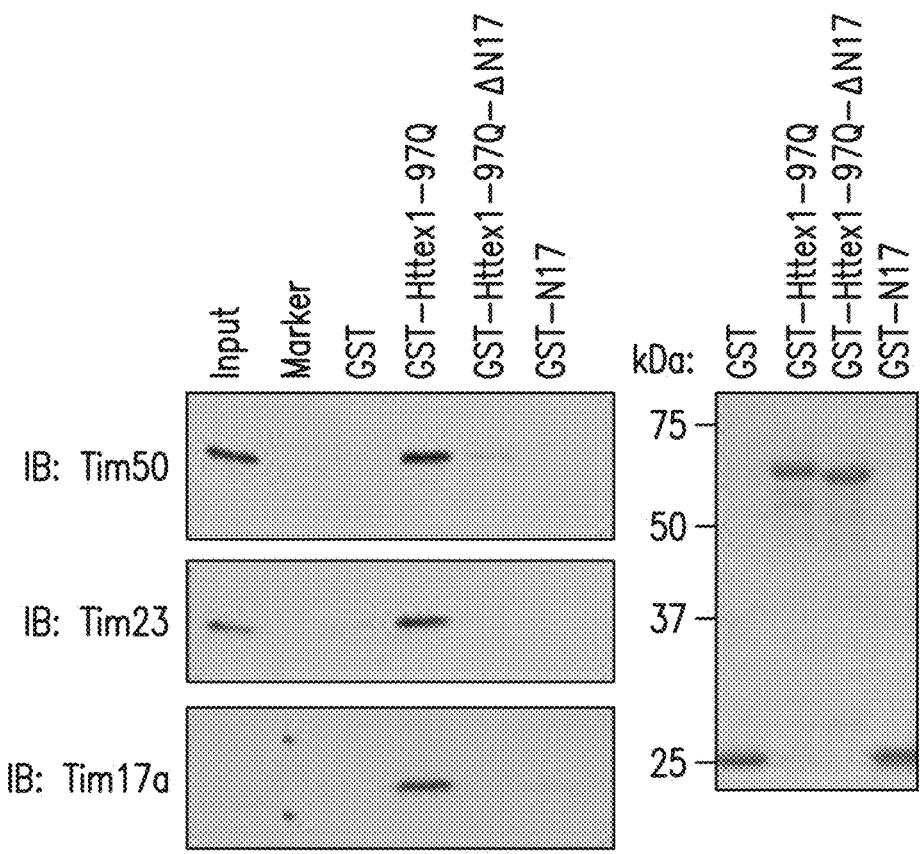
Figure 1H:
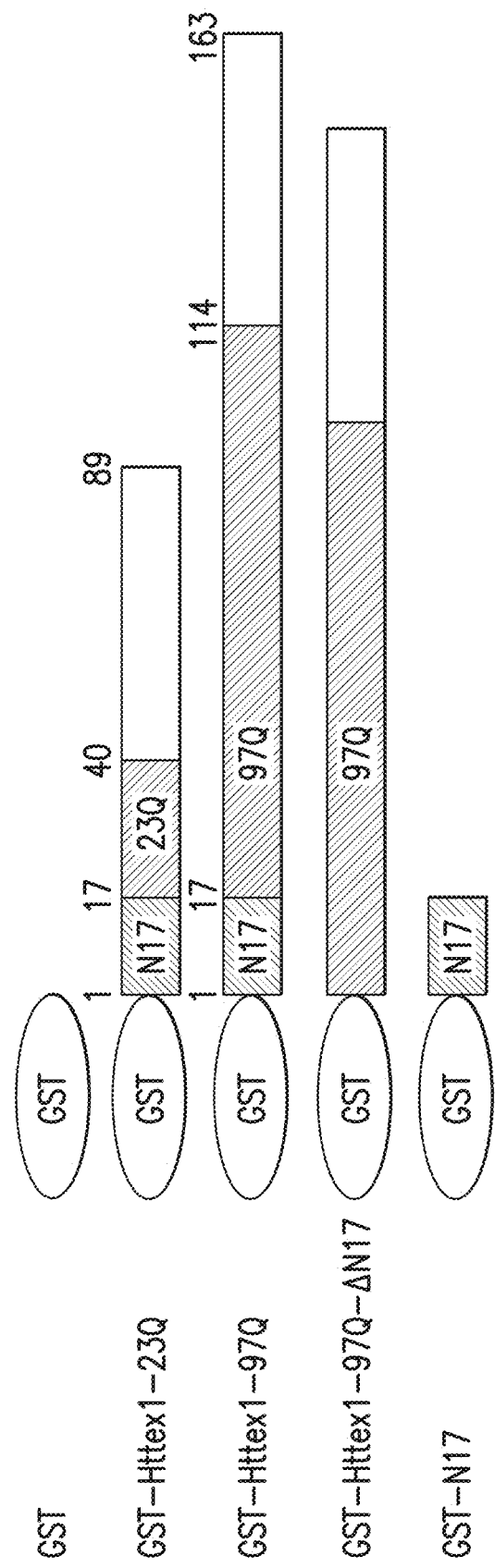
Figure 2B:
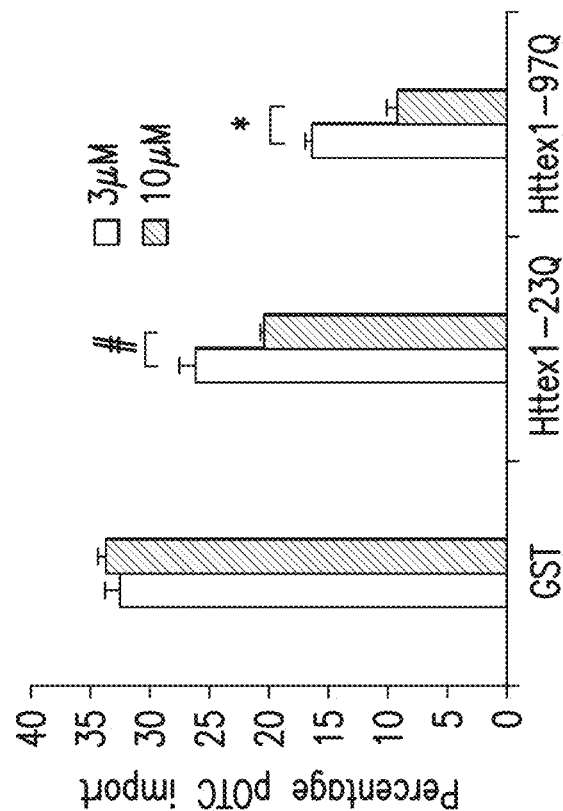
Figure 2A:
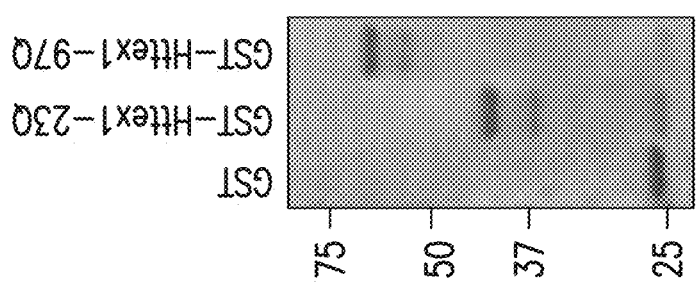
Figure 2C:
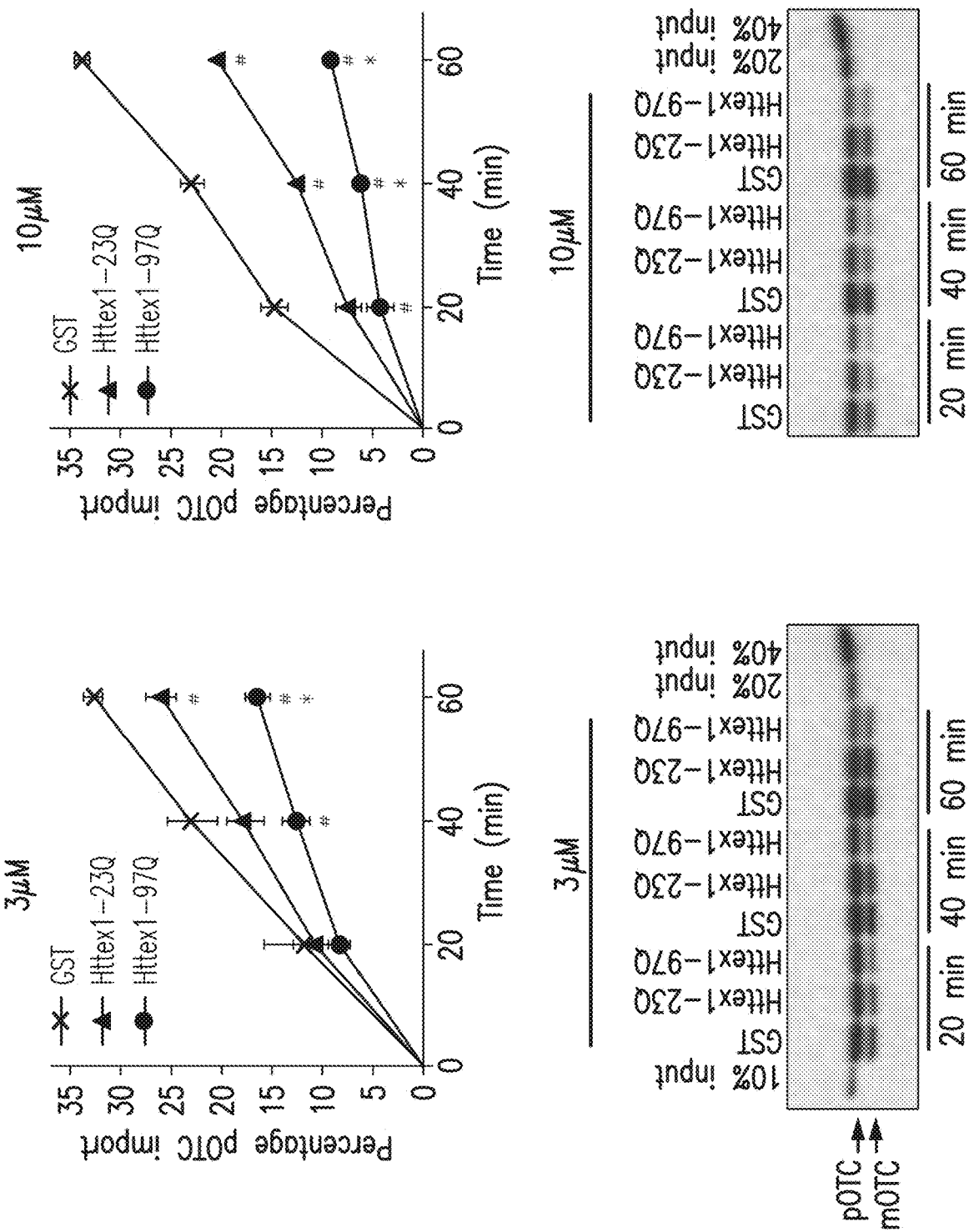
Figure 3A:
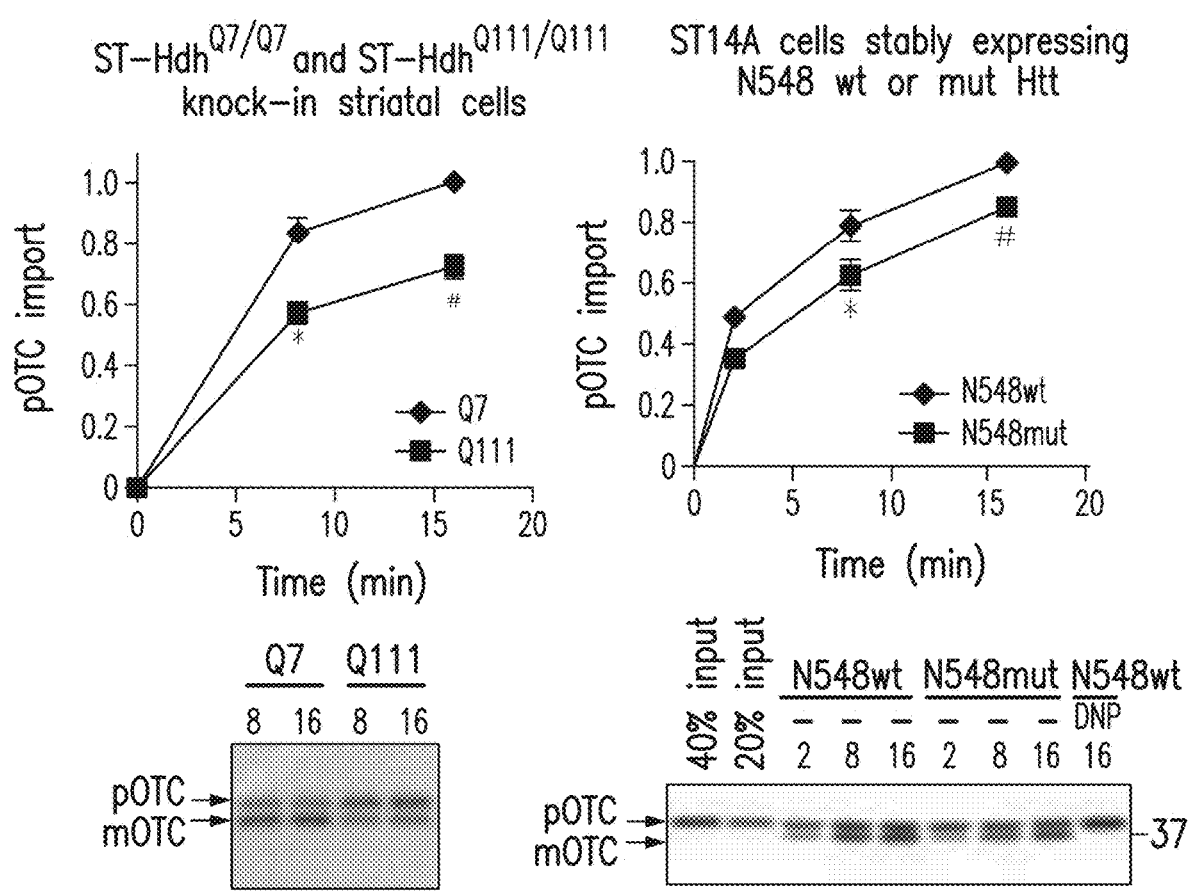
Figure 3B:
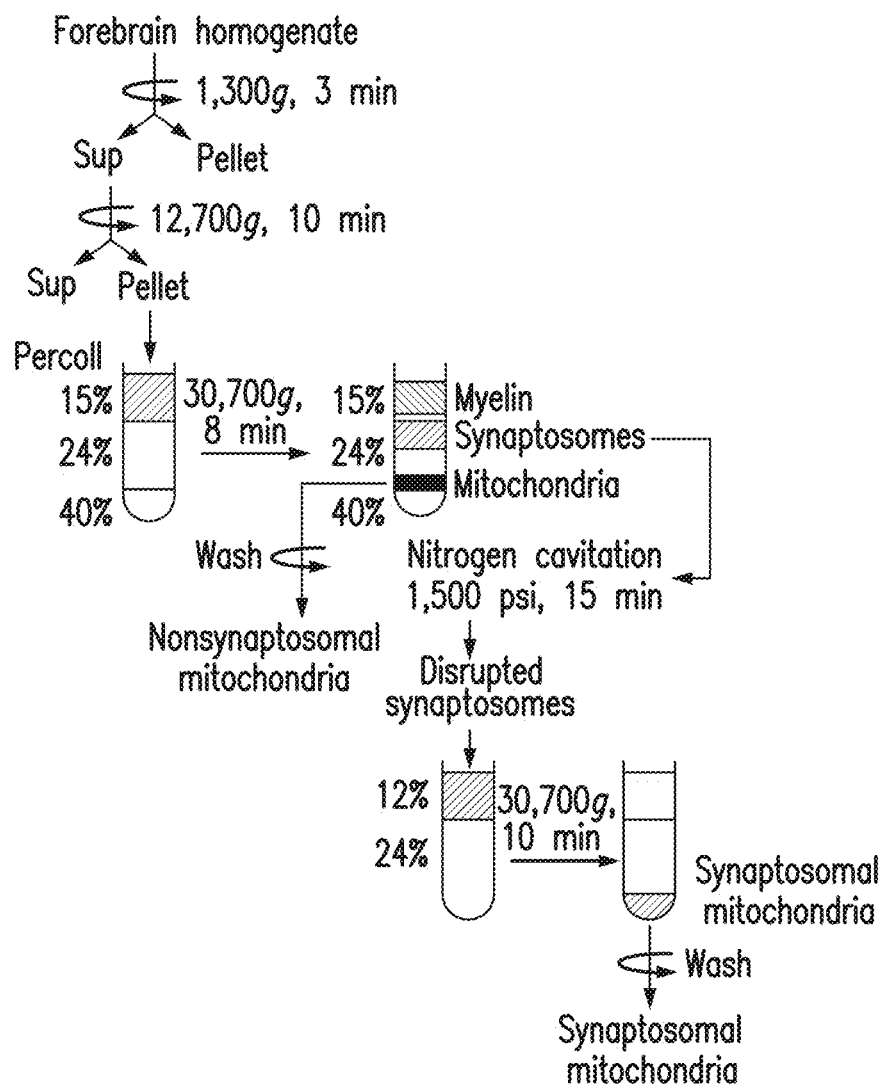
Figure 3C:
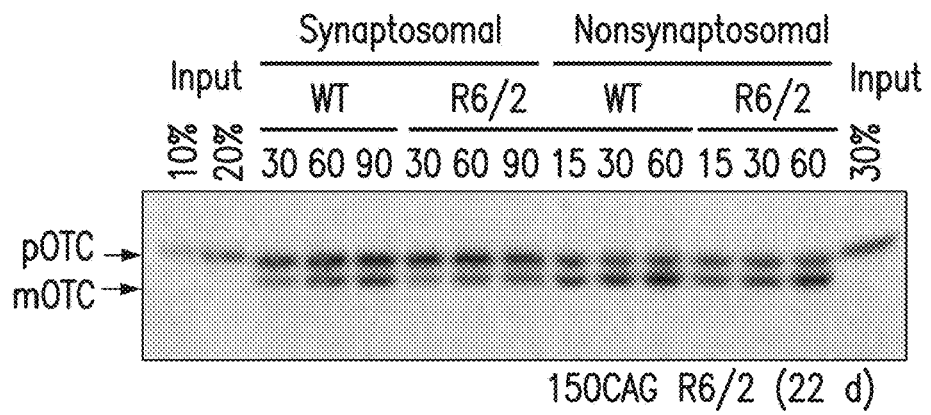
Figure 3C:
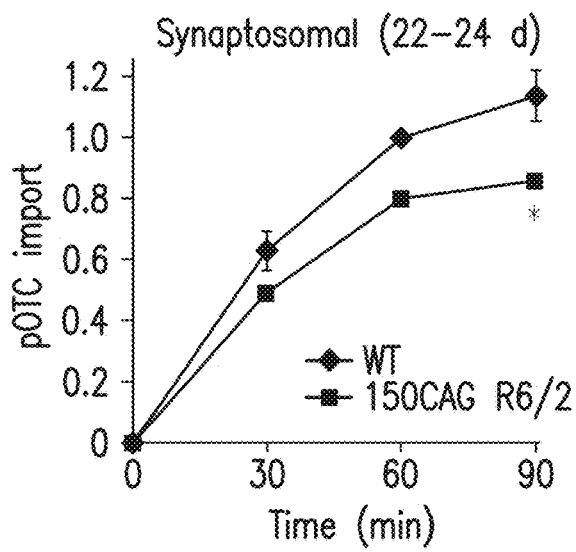
Figure 3C:
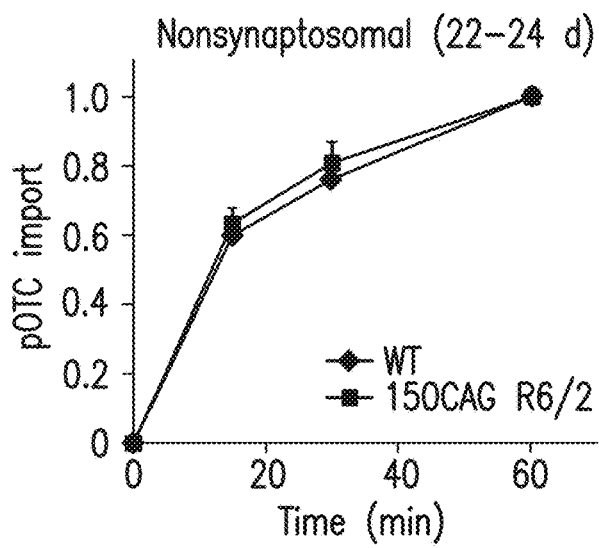
Figure 1E:
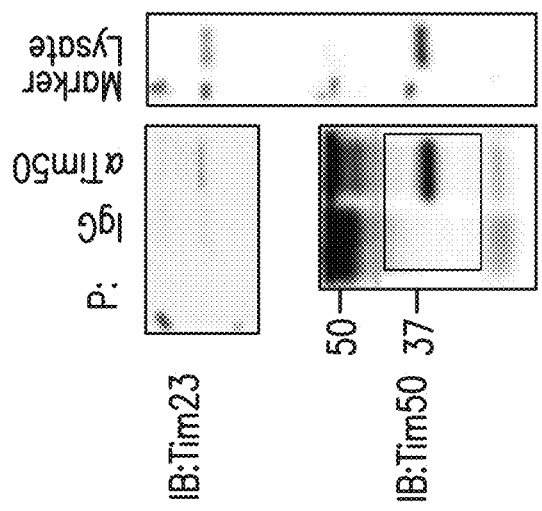
Figure 1S:
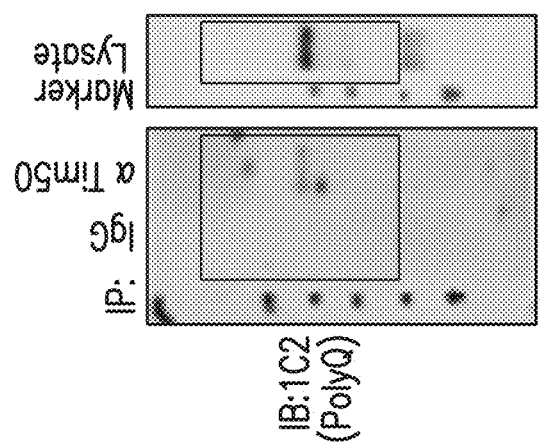
Figure 1D:
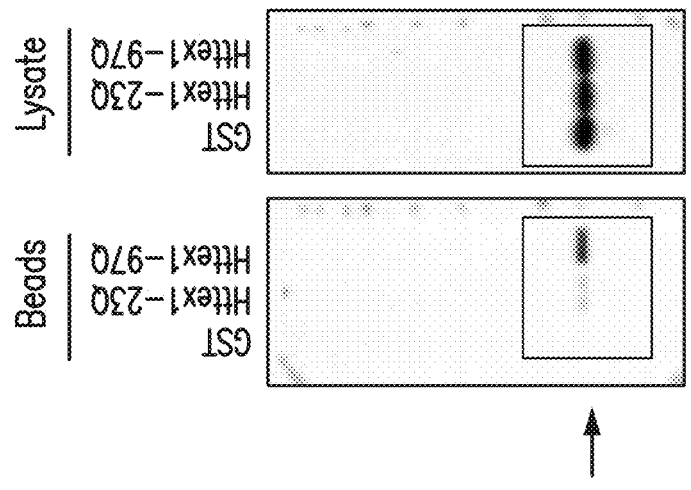
Figures 1F, 1G, 15:
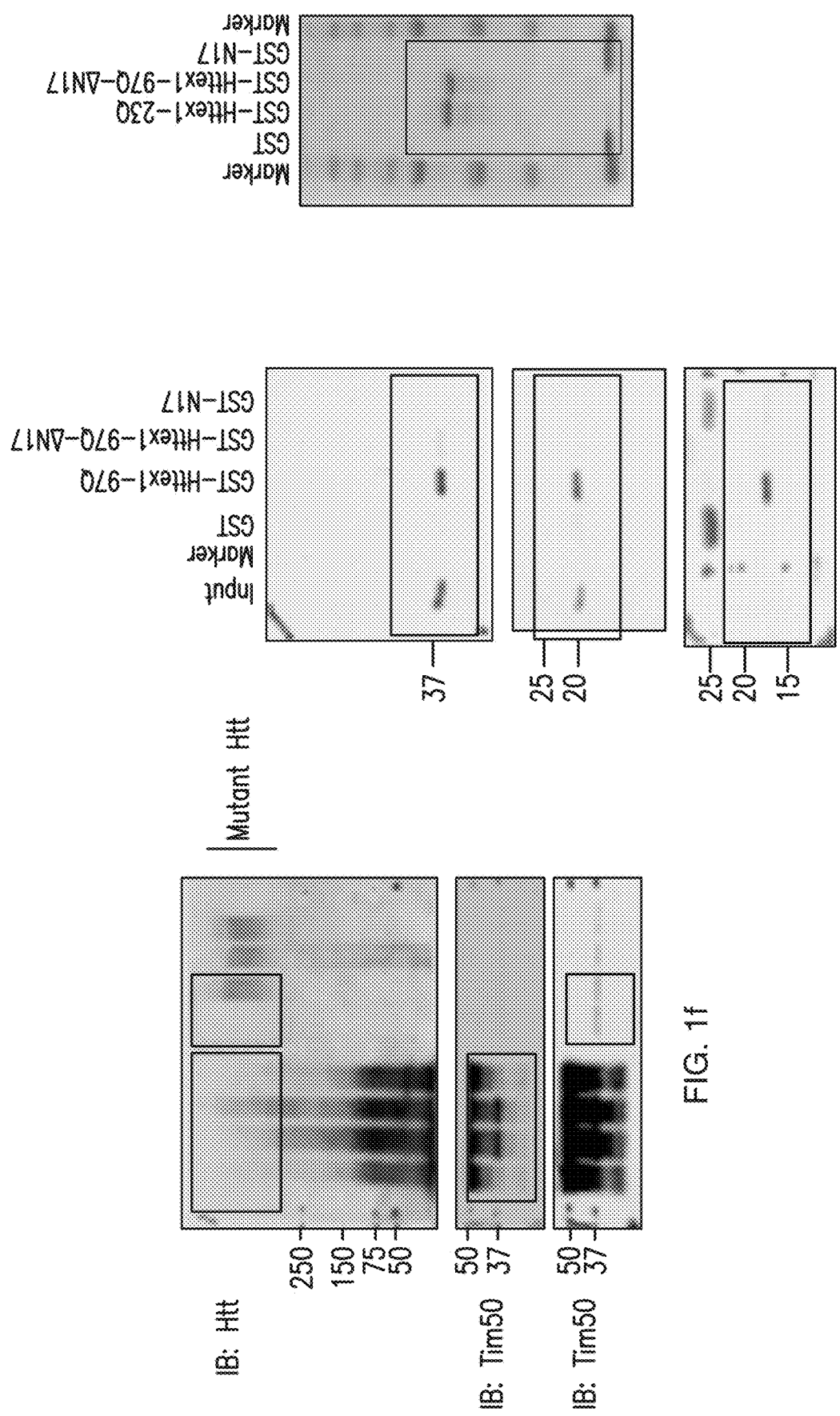
Figure 15:
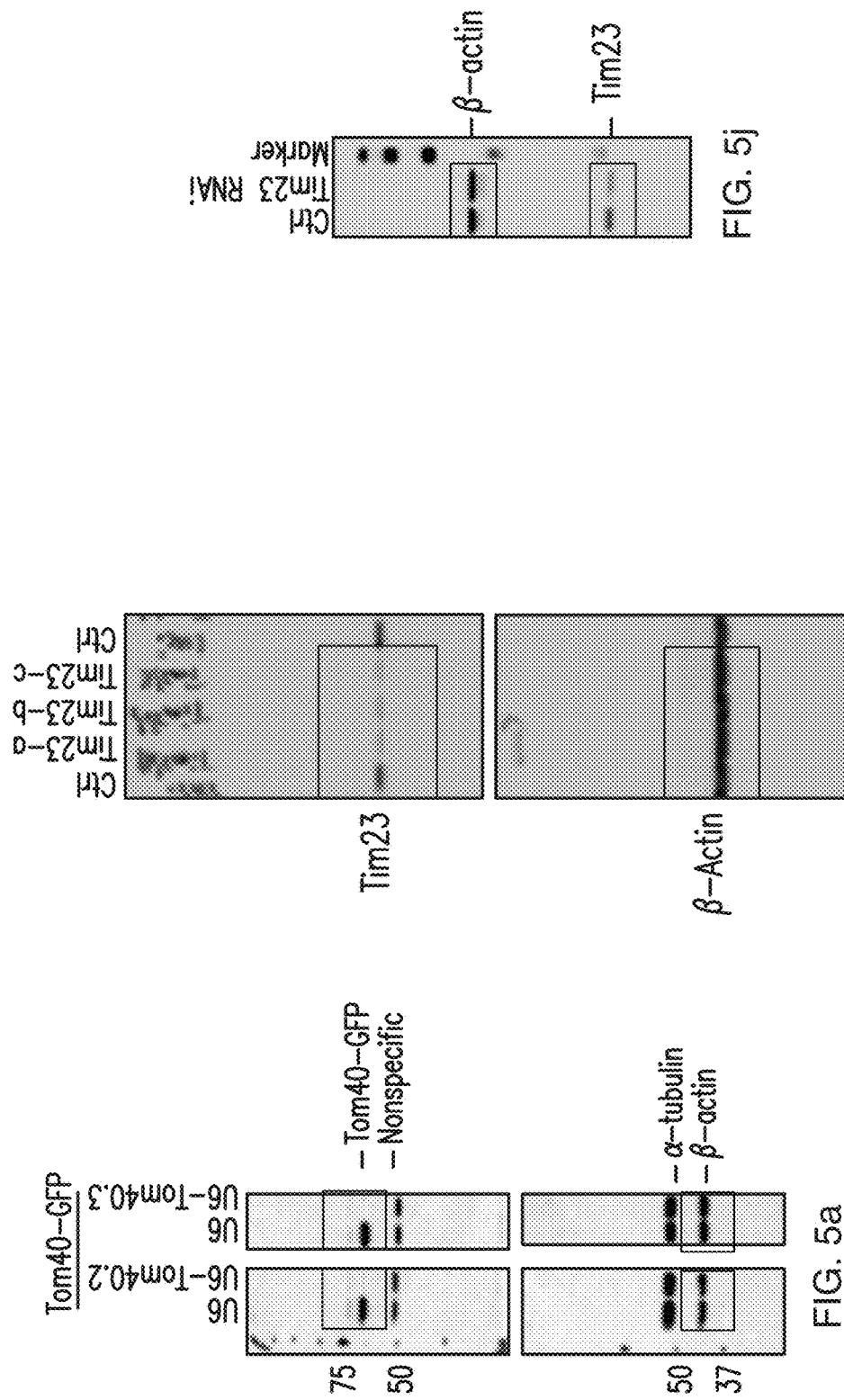

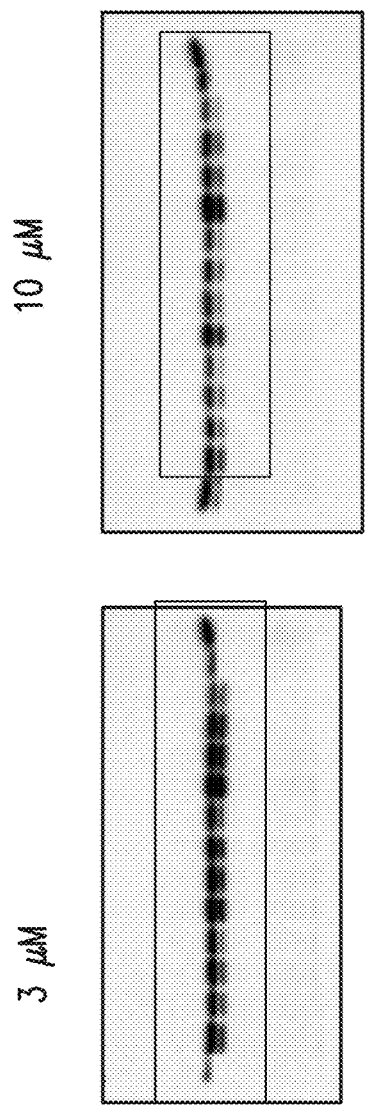
FIG. 2c
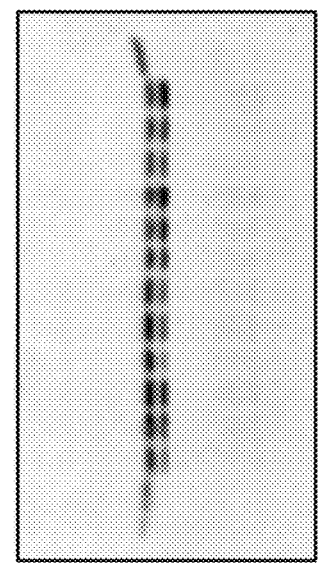
FIG. 3c
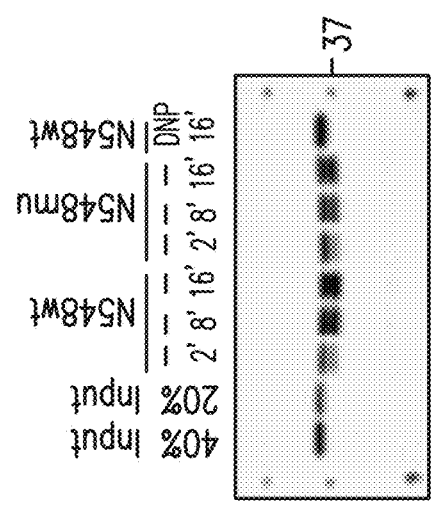
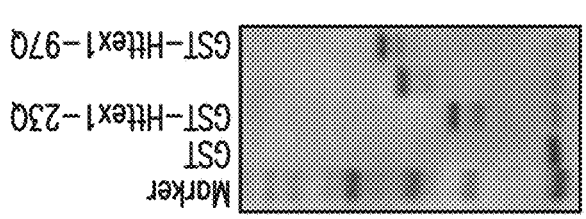
FIG. 2a
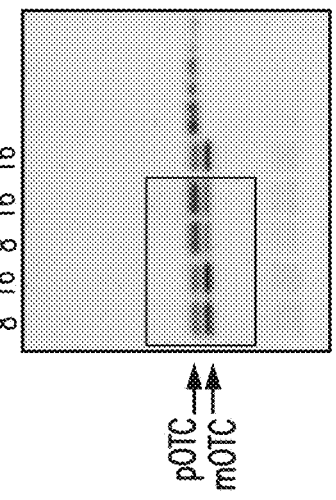
FIG. 3a
FIG. 15 (CONTINUED)

MUTANT HUNTINGTIN-MEDIATED PROTEIN DYSFUNCTION

CROSS-REFERENCE TO RELATED APPLICATIONS

This application is a continuation of U.S. patent application Ser. No. 15/295,538, filed Oct. 17, 2016, which is a continuation of International Patent Application No. PCT/US2015/026473, filed Apr. 17, 2015, which claims priority to U.S. Provisional Application Ser. No. 61/981,092, filed Apr. 17, 2014, and U.S. Provisional Application Ser. No. 61/992,504, filed May 13, 2014, priority to each of which is claimed and the contents of each of which are incorporated by reference in their entireties.

GRANT INFORMATION

This invention was made with government support under Grant Nos. R01 NS039324, NS077748, and K01 AG033724, awarded by the National Institutes of Health. The government has certain rights in the invention.

SEQUENCE LISTING

The specification incorporates by reference the Sequence Listing submitted herewith via EFS on Nov. 20, 2019. Pursuant to 37 C.F.R. § 1.52(e)(5), the Sequence Listing text file, identified as 0723960808_ST25.txt, is 2,995 bytes and was created on Nov. 14, 2019. The Sequence Listing, electronically filed herewith, does not extend beyond the scope of the specification and thus does not contain new matter.

1. INTRODUCTION

The present invention relates to methods and compositions for inhibiting neurodegeneration in a subject having, or genetically at risk to develop, Huntington's Disease.

2. BACKGROUND OF THE INVENTION

Huntington's Disease ("HD") is a fatal autosomal dominant neurodegenerative disorder characterized by age dependent progressive neurological dysfunction and selective loss of neurons in the striatum and cortex. The genetic cause of HD is an abnormal expansion of CAG repeats (>40 repeats) encoding polyglutamine (polyQ) in exon 1 of the huntingtin gene (Htt). Although the genetic cause of HD has been identified, the pathogenic mechanisms of the disease remain unclear, and no therapy that ameliorates the neurodegenerative process is available.

Mitochondrial dysfunction has been highlighted as a critical driver of HD pathophysiology[3-5]. Mitochondria are important in diverse cellular functions, including bioenergetics, calcium homeostasis and apoptotic signaling. Several proteolytically cleaved N-terminal fragments of mutant Htt proteins have been identified in cells and appear to be more cytotoxic and prone to aggregation than full-length mutant Htt[6-8]. Ultrastructural and biochemical evidence indicates that N-terminal fragments of mutant Htt associate with mitochondria in cellular and animal models of HD[9-11]. However, the mechanism directly linking mutant Htt and mitochondrial dysfunction remains unknown.

Mitochondria contain approximately 1,500 different proteins, 99% of which are encoded by the nuclear genome[12]. Therefore, the import, sorting and assembly of nuclearly encoded mitochondrial proteins are essential for normal mitochondrial function. Only 13 proteins of the respiratory chain are encoded by the mitochondrial genome and synthesized in mitochondria. Nuclearly encoded mitochondrial proteins are synthesized in cytosolic ribosomes as precursor proteins and imported into mitochondria by evolutionarily conserved multi-subunit mitochondrial membrane translocases: translocase of the outer membrane (TOM) and translocase of the inner membrane (TIM)[12,13]. Whereas the TOM complex serves as the entry gate for almost all nuclearly encoded proteins, two distinct TIM complexes, the TIM23 and TIM22 complexes, act in the inner membrane. The TIM23 complex imports all matrix proteins and a subset of inner membrane and intermembrane space proteins, which harbor N-terminal cleavable presequences. The TIM22 complex, a carrier translocase, imports hydrophobic inner membrane proteins through internal targeting signals. Thus, nuclearly encoded mitochondrial proteins use specific import systems for precise mitochondrial localization. Blockade of import pathways is believed to lead to mitochondrial dysfunction[14].

3. SUMMARY OF THE INVENTION

The present invention relates to methods of inhibiting neurodegeneration in a subject suffering from or genetically at risk and/or destined to develop Huntington's Disease (HD) comprising increasing, in neurons of the subject, the activity of the TIM23 mitochondrial protein import complex. It is based, at least in part, on the discoveries that (i) there is a hitherto unknown interaction between mutant Huntingtin (Htt) protein and the TIM23 mitochondrial protein import complex; (ii) recombinant mutant Htt directly inhibits mitochondrial protein import in vitro; (iii) mitochondria from brain synaptosomes of presymptomatic HD mice and from mutant Htt-expressing primary neurons exhibit a protein import defect; and (iv) mutant Htt-induced mitochondrial import defect and subsequent neuronal death were attenuated by overexpression of TIM23 complex subunits, demonstrating a causal role for deficient mitochondrial protein import in mutant Htt-induced neuronal death.

The present disclosure provides for methods of treating and/or inhibiting the progression of HD in a subject in need thereof by administering an agent in an amount effective to decrease an interaction between a mutant Htt and a TIM23 complex. An interaction can be, for example, a physical interaction, protein-protein binding interaction, covalent interaction, and/or non-covalent interaction.

In certain non-limiting embodiments, the agent is administered in an amount effective to increase activity of a TIM23 complex, for example, an increase in protein import into mitochondria of the subject.

In certain non-limiting embodiments, the TIM23 complex can comprise, for example, a TIM23 complex subunit selected from the group consisting of Tim23, Tim50, Tim17a, and combination thereof.

The present disclosure also provides for methods of reducing or inhibiting neurodegeneration, for example, neurodegeneration in a neuron expressing a mutant Htt, by contacting an agent to a neuron in an amount effective to inhibit or reduce neurodegeneration. In certain embodiments, the agent is contacted to the neuron in an amount effective to decrease an interaction between a mutant Htt and a TIM23 complex. In other embodiments, the agent is contacted to the neuron in an amount effective to increase activity of a TIM23 complex, for example, an increase in protein import into mitochondria of the neuron.

In certain embodiments, the agent is an agent that competes with a TIM23 complex, or a subunit thereof, for binding to a mutant Htt. In certain embodiments, the agent comprises a TIM23 complex protein; a TIM23 complex subunit selected from the group consisting of Tim23, Tim50, Tim17a, and combination thereof; and/or a nucleic acid encoding the TIM23 complex or subunits thereof.

In other non-limiting embodiments, the agent is an agent that phosphorylates the mutant Htt protein, for example, at serine amino acid residues S13 and/or S16 of the mutant Htt protein.

In certain embodiments, the mutant Htt protein comprises at least 97 glutamine repeats (97Q).

The present disclosure further provides for kits comprising an agent that can decrease interactions between Htt and a TIM23 complex, increase activity of a TIM23 complex, and/or reduce or inhibit neurodegeneration.

4. BRIEF DESCRIPTION OF THE FIGURES

FIGS. 1a-1h. Mutant Htt interacts with the TIM23 complex. (1a) Caudate nucleus sections from human HD grade 2 and control brains, subjected to immunohistochemistry for indicated proteins. Mutant Htt aggregates detected by anti-Htt (EM48) antibody colocalize with mitochondrial proteins Tim23 and DRP1 in human HD caudate nucleus in deconvolved confocal images. (1b) ST-Hdh cells transfected with mtGFP expression plasmid, subjected to immunofluorescence with anti-polyQ antibody (1C2) to label mutant Htt (red). Mutant Htt in ST-Hdh$^{Q111/Q111}$ cells partially colocalizes (yellow) with mitochondria in deconvolved confocal images. Scale bars (1a, 1b), 10 µm. (1c) Mouse forebrain mitochondria incubated with GST alone or GST-Httex1 proteins were subjected to GST pull-down assays. Bound proteins were identified by mass spectrometric analysis. Venn diagram represents the number of identified proteins. TIM23 complex components were identified among the Httex1-97Q-binding proteins. See also Table 1. (1d) Interaction between Tim23 and Httex1-97Q was verified by GST pull-down assays as in c, followed by immunoblotting with anti-Tim23 antibody. (1e, 1f) Endogenous interaction between mutant Htt and Tim50 was found in ST-HdhQ111/Q111 cells (1e) and 5-week-old R6/2 mouse forebrain (1f) by coimmunoprecipitation (IP) with anti-Tim50 antibody followed by immunoblotting (IB). Normal IgG is a negative control. (1g) Mitochondria isolated from ST14A cells were incubated with equimolar concentration of the indicated recombinant GST-fusion proteins and were subjected to GST pull-down assays. Bound proteins were analyzed by immunoblotting with indicated antibodies. Right, Coomassie blue staining of GST fusion proteins used in assays. (1h) A schematic representation of GST-Htt proteins used in 1c, 1d, 1g. The experiments (1a, 1b, 1d-1g) were successfully repeated three times. Full-length blots/gels (1d-1g) are presented in FIG. 15.

FIGS. 2a-2c. Mutant Htt directly inhibits mitochondrial protein import. (2a) Coomassie blue staining of GST fusion proteins used in 2b, 2c. (2b) Forebrain mitochondria prepared from adult WT mice were preincubated with GST or GST-Httex1 proteins (3 or 10 µM) on ice for 1 h and subjected to import assays using [$^{35}$S]pOTC (60 min). Final concentrations of GST-Htt proteins in the import reaction are 0.6 and 2 µM. Data are presented as mean+s.e.m. Inhibition of pOTC import by Httex1 proteins was dose dependent (#P=0.001 and *P=0.0001, F5,12=109.40). GST alone showed import activity similar to vehicle (phosphate-buffered saline), indicating no effect of GST on pOTC import (data not shown). (2c) Kinetic analysis of pOTC import reaction after preincubation with indicated recombinant proteins as in 2b. Representative gel images used for quantification are shown. Import reaction times are indicated. Httex1 proteins decreased the import of pOTC into mitochondria in a polyQ length-dependent manner. # and * represent significant difference compared to GST and GST-Httex1-23Q at the given time point, respectively. 3 µM, 40 min: Httex1-97Q, #P=0.008, F2,6=7.404. 3 µM, 60 min: Httex1-23Q, #P=0.009; Httex1-97Q, #P<0.0001, *P=0.002, F2,6=43.28. 10 µM, 20 min: Httex1-23Q, #P=0.002; Httex1-97Q, #P=0.0002, F2,6=31.29. 10 µM, 40 min: Httex1-23Q, #P<0.0001; Httex1-97Q, #P<0.0001, *P=0.0006, F2,6=153.73. 10 µM, 60 min: Httex1-23Q, #P<0.0001; Httex1-97Q, #P<0.0001, *P<0.0001, F2,6=1,111.73. Data are presented as mean±s.e.m. Percentage pOTC import (2b, 2c) represents the percentage of imported mOTC radioactivity compared to input (total [35S]pOTC radioactivity added to each reaction). One-way ANOVA, Bonferroni t-test. n=3 independent experiments (2b, 2c). Full-length blots/gels (2a, 2c) are presented in FIG. 15.

FIGS. 3a-3e. Mitochondria isolated from mutant Htt-expressing striatal cells and mouse brain exhibit decreased protein import. (3a) Mitochondria isolated from the indicated striatal cells were subjected to pOTC import assays. Addition of a mitochondrial uncoupler, 2,4-dinitrophenol (DNP), to mitochondria before starting the import reaction confirmed that dissipation of mitochondrial membrane potential blocks import. Mitochondria from ST-HdhQ111/Q111 and N548mut cells showed significantly decreased pOTC import compared to that of control cell lines. Times are indicated in minutes in 3a, 3c. ST-HdhQ111/Q111, 8 min: *P=0.0004, t=5.90, d.f.=8, n=5 independent experiments; ST-HdhQ111/Q111, 16 min: #P=0.0022, U=0, n=6 independent experiments; N548mut, 8 min: *P=0.045, t=2.29, d.f.=10, n=6 independent experiments; N548mut, 16 min: #P=0.0022, U=0, n=6 independent experiments. (3b) Schematic of synaptosomal and nonsynaptosomal mitochondria isolation protocol from mouse forebrain. Sup, supernatant. (3c) Synaptosomal mitochondria isolated from 22- to 24-d-old, presymptomatic 150CAG R6/2 mice showed significantly decreased pOTC import compared to that of WT (*P=0.029, t=3.34, d.f.=4, n=3 independent experiments; 3 or 4 WT or R6/2 brains were pooled in each experiment). (3d) Synaptosomal mitochondria isolated from 195CAG R6/2 showed significantly decreased pOTC import compared to that of WT (5-6 weeks, *P=0.012, t=3.59, d.f.=6, n=4 independent experiments; 10-11 weeks, *P=0.029, U=0, n=4 independent experiments). Modest reduction of pOTC import was also found in 195CAG R6/2 nonsynaptosomal mitochondria at 5-6 weeks of age compared to that of control WT (*P=0.0006, U=0, n=7 independent experiments), but not at 10-11 weeks of age (n=9 independent experiments). (3e) 195CAG R6/2 liver mitochondria showed significantly impaired pOTC import only in late-disease stage (13-14 weeks) (*P=0.0044, t=3.92, d.f.=8; #P=0.0079, U=0, n=5 independent experiments). (3a, 3c) Representative gel images of at least 3 independent experiments are shown. (3a, 3c-3e) Mann-Whitney U and unpaired t-tests (two-tailed). Data are presented as mean±s.e.m. Full-length blots/gels (3a, 3c) are presented in FIG. 15.

Figure 4B:
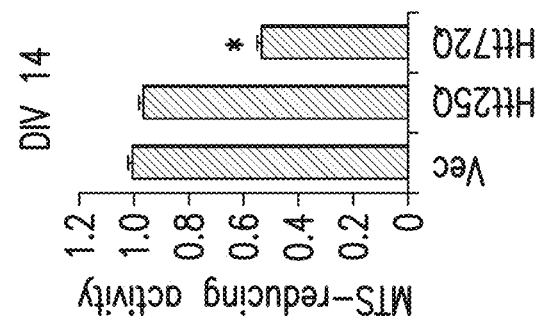
Figure 4C:
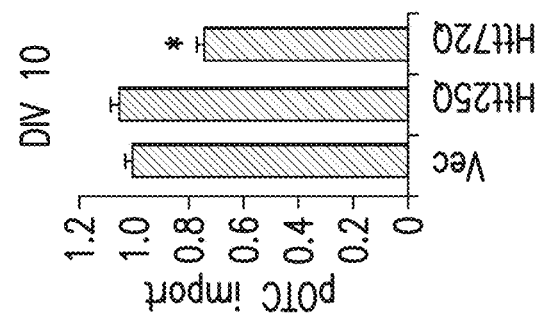
Figure 4A:
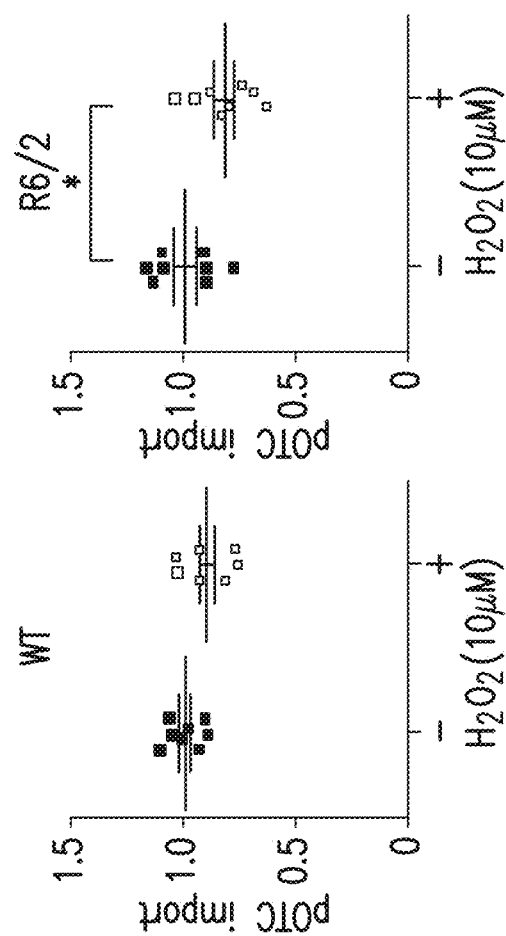

FIGS. 4a-4c. Mutant Htt-expressing primary neurons show impaired mitochondrial protein import. (4a) Primary cortical neurons from eight R6/2 and eight littermate WT embryos (E15.5) were individually plated into two dishes and treated at day in vitro (DIV) 7 with or without sublethal H2O2 (10 µM) for 2 h. Isolated mitochondria were then subjected to pOTC import assay (30 min). R6/2 neurons treated with sublethal H2O2 showed a significant decrease in pOTC import compared to vehicle-treated R6/2 neurons (unpaired t-test; *P=0.022, t=2.58, d.f.=14, n=8 cultures per condition prepared from 8 different embryos from 3 independent experiments). Data points are presented, with mean±s.e.m. (4b) Primary cortical neurons prepared from WT embryos were transduced with Httex1-25Q (Htt25Q), Htt72Q or control empty-vector lentivirus (Vec) at DIV 5. MTS assays were performed at DIV 14. Expression of Htt72Q, but not Htt25Q, decreased MTS-reducing activity, indicating that mutant Htt decreases mitochondrial metabolic activity (*P<0.0001 compared to Htt25Q or vector control, n=17 (vector), 12 (Htt25Q) or 12 (Htt72Q) cultures from 3 independent experiments). (4c) Primary cortical neurons were transduced as in b. Mitochondria were isolated from neurons at DIV 10 before mutant Htt-induced neuronal death and subjected to pOTC import assays (30 min). Mitochondria isolated from neurons expressing Htt72Q exhibited decreased protein import compared to those expressing Htt25Q or vector control (*P<0.0001, $F_{2,18}$=24.42, n=5 (vector), 10 (Htt25Q) or 6 (Htt72Q) mitochondria samples from 3 independent experiments). Htt25Q-expressing neurons showed no impairment of mitochondrial import compared to control neurons transduced with empty vector. Data (4b, 4c) are presented as mean+s.e.m. One-way ANOVA, Bonferroni t-test.

FIGS. 5a-5l. Global and TIM23-driven mitochondrial protein import is necessary for survival of primary neurons. (5a) Knockdown of Tom40 was confirmed using COS cells transfected with Tom40-GFP expression plasmid and Tom40 RNAi (U6-Tom40.2, U6-Tom40.3) or control U6 plasmid. (5b) DIV 5 cortical neurons were cotransfected with U6-Tom40.2 RNAi or U6 plasmid and with β-gal expression plasmid and subjected to immunocytochemistry with anti-β-galactosidase (β-gal) antibody at DIV 8. Arrows indicate representative β-gal+ control (top) and Tom40 RNAi (bottom) neurons, the latter of which show condensed or fragmented nuclei. (5c) Neurons treated as in b were quantified for cell death by scoring nuclear morphology. Neuronal death was significantly increased in Tom40 knockdown cortical and striatal neurons compared to control neurons (one-way ANOVA, Fisher least significant difference; cortical neurons, *P=0.0002, #P<0.0001, $F_{2,12}$=41.65, n=5 coverslips from 4 independent experiments; striatal neurons, *P=0.018, #P<0.0001, $F_{2,14}$=19.46; n=6 (U6 and U6-Tom40.3) or 5 (U6-Tom40.2) coverslips from 4 independent experiments). (5d) Cortical neurons cotransfected with U6-Tom40.3 RNAi or U6 plasmid and with a β-gal plasmid were subjected to immunocytochemistry with anti-β-gal and anti-active caspase-3 antibodies and nuclear labeling with DAPI at the indicated time points after transfection. Active caspase-3+ neurons among β-gal+ transfected neurons were quantified. Inset: representative image of Tom40 knockdown neurons with active-caspase-3 immunoreactivity. Tom40 knockdown neurons showed increased active caspase-3 compared to control neurons (unpaired t-test; *P=0.0005, t=7.71, d.f.=5, n=6 slides per group from 3 independent experiments). (5e) Transfected cortical neurons as in d were treated with qVD-OPh (20 µM) or vehicle (DMSO) and quantified for cell death as in c. qVD-OPh decreased Tom40 RNAi-induced cell death. *P<0.0001 compared to U6 (DMSO), #P<0.0001 compared to U6-Tom40.3 (DMSO), **P<0.0001 compared to U6 (qVD-OPh), $F_{3,20}$=94.96, n=6 coverslips per condition from 3 independent experiments. (5f) Knockdown of Tim23 using shRNA lentiviruses (Tim23.a, Tim23.b and Tim23.c) was confirmed in cortical neurons by immunoblotting. Ctrl: luciferase shRNA lentivirus. (5g) DIV 5 neurons infected with Tim23 shRNA or ctrl shRNA lentiviruses were subjected to MTS assays at DIV 12. Tim23 knockdown decreased mitochondrial metabolic activity in cortical and striatal neurons (cortical neurons: *P<0.0001 compared to ctrl, $F_{3,66}$=121.96, n=13 (ctrl), 19 (Tim23.a, Tim23.b, Tim23.c) cultures per group from 6 independent experiments; striatal neurons: *P<0.0001 compared to ctrl, $F_{3,69}$=57.93, n=16 (ctrl), 19 (Tim23.a, Tim23.b, Tim23.c) cultures per group from 6 independent experiments). (5h, 5i) DIV 5 neurons infected with Tim23.a or luciferase (ctrl) shRNA lentiviruses were fixed at DIV 12 and subjected to immunofluorescence with indicated antibodies and nuclear staining (Hoechst 33342). Cell death was assessed by nuclear morphology. Representative images of transduced cortical neurons (5h). Tim23 knockdown significantly increased the percentage of dead cells in cortical (*P<0.0001 compared to ctrl, $F_{3,24}$=60.98, n=7 cultures per condition from 3 independent experiments) and striatal neurons (*P=0.0004 and #P=0.0013 compared to ctrl, $F_{3,28}$=7.623, n=8 cultures per condition from 3 independent experiments) (5i). (5j) Knockdown of Tim23 was confirmed using N2a cells transfected with Tim23 RNAi or control scrambled (ctrl) pBSU6-GFP plasmid by immunoblotting. (5k, 5l) DIV 5 cortical neurons were transfected with Tim23 RNAi or control pBSU6-GFP plasmid. At DIV 8, loss of mitochondrial membrane potential and cell death were assessed using TMRM and nuclear dye RedDot2 by live confocal imaging. Representative images (z projection) at indicated time points demonstrate Tim23 knockdown induces mitochondrial depolarization and subsequent cell death (5k). The percentage of TMRM+ neurons and live neurons among GFP+ transfected neurons was quantified (5l). Tim23 knockdown significantly decreased the number of TMRM+ neurons and live neurons compared to control transfection (log-rank test, *P=0.002; n=49 neurons from 3 wells per group). Loss of mitochondrial membrane potential preceded neuronal death in Tim23 knockdown neurons by 3.4±0.13 h (n=25). Experiments (5a, 5f, 5j) were successfully repeated three times and full-length blots/gels are presented in FIG. 15. (5c, 5e, 5i) 100-200 β-gal+ neurons per coverslip were counted. Scale bars: 10 µm (5b, 5d, 5k), 20 µm (5h). Data are presented as mean+s.e.m. (5c,5e,5g,5i) or mean±s.d. (5d). (5e, 5g, 5i) One-way ANOVA, Bonferroni t-test.

Figure 6A:
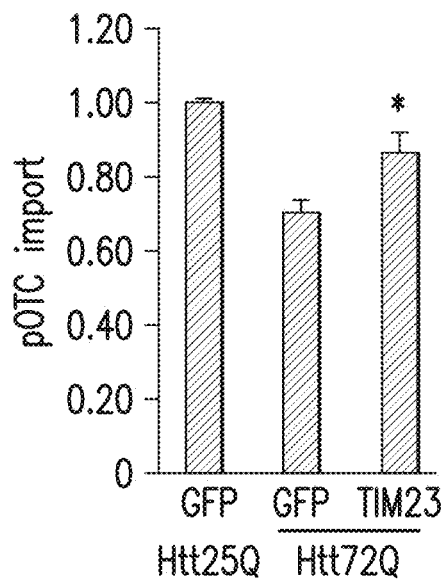
Figure 6B:
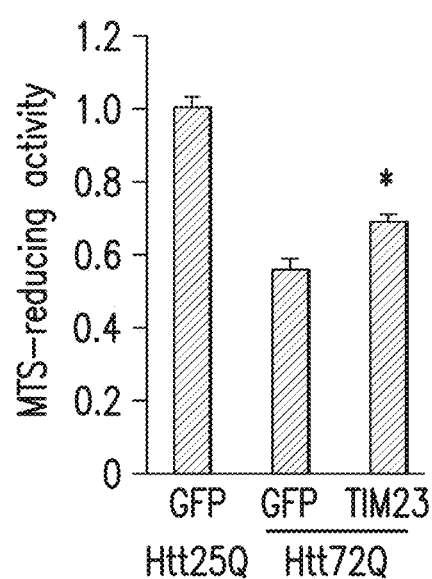
Figure 6C:
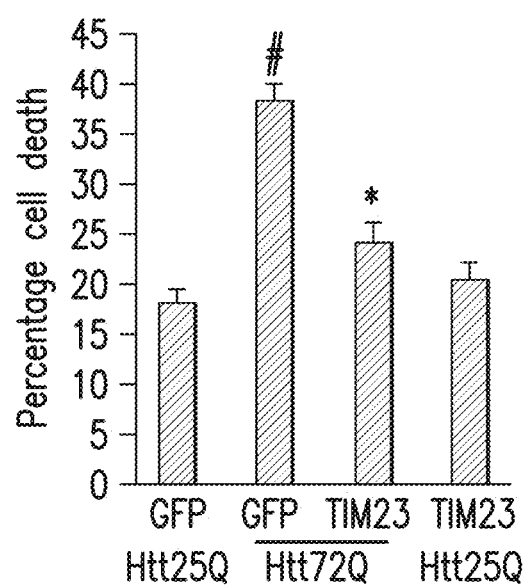

FIGS. 6a-6c. Augmentation of mitochondrial protein import rescues neurons from mutant Htt-induced death. (6a) DIV 5 cortical neurons were transduced with WT Httex1-25Q (Htt25Q) or mutant Httex1-72Q (Htt72Q) lentivirus and at DIV 6 were cotransduced with lentivirus expressing three subunits of the TIM23 complex, Tim23, Tim50 and Tim17a. Mitochondria isolated from transduced neurons at DIV 10 were subjected to pOTC import assay (30 min). Overexpression of the TIM23 complex subunits increased pOTC import in Htt72Q neurons (*P=0.007 compared to GFP-expressing Htt72Q neurons, $F_{2,27}$=14.05, n=10 samples per condition from 5 independent experiments). (6b) Primary cortical neurons transduced as in a were subjected to MTS assays at DIV 14. Overexpression of the TIM23 complex subunits partially but significantly increased mitochondrial metabolic activity (*P=0.006 compared to GFP-expressing Htt72Q neurons, $F_{2,45}$=59.39, n=17 wells per group for GFP-expressing Htt25Q and GFP-expressing Htt72Q neurons, n=14 wells for TIM23-expressing Htt72Q neurons from 4 independent experiments). (6c) Primary cortical neurons transduced as in a were assessed for cell death by scoring nuclear morphology at DIV 14. Htt72Q-expressing neurons showed increased cell death compared to Htt25Q-expressing neurons (#P<0.0001, GFP-expressing Htt72Q compared to GFP-expressing Htt25Q neurons). Overexpression of the TIM23 complex subunits in Htt72Q neurons inhibited neuronal death (*P<0.0001 compared to GFP-expressing Htt72Q neurons). F3,51=29.47, n=16 (GFP-expressing Htt25Q neurons), 15 (GFP-expressing Htt72Q neurons) and 12 (TIM23-expressing Htt72Q and TIM23-expressing Htt25Q neurons) wells per group from 3 independent experiments; 200 neurons were counted per well. (6a-6c) Data are presented as mean+s.e.m. One-way ANOVA, Bonferroni t-test.

Figure 7:
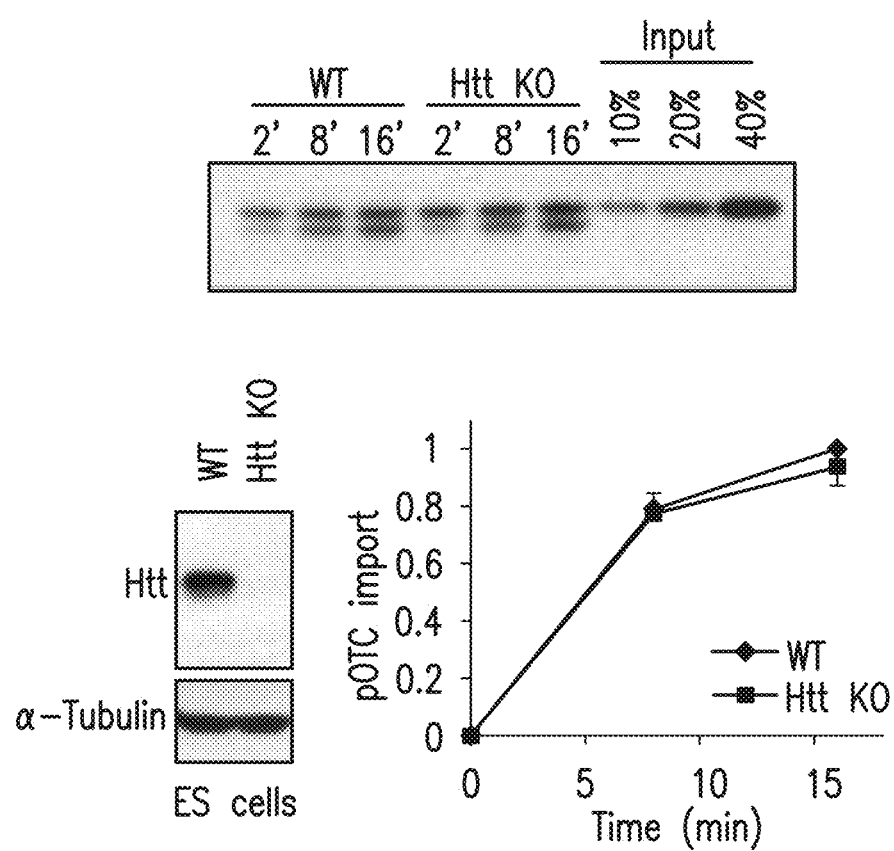

FIG. 7. Endogenous Htt is not required for mitochondrial protein import in embryonic stem (ES) cells. Mitochondria prepared from wild-type (WT) and Htt knockout (KO) ES cells were subjected to in vitro pOTC import assay. A representative gel image is shown (top). Immunoblot analysis confirmed the absence of Htt protein in Htt KO ES cells (bottom left). WT and Htt KO mitochondria demonstrated similar pOTC import activity (bottom right, n=3). Mean±s.e.m.

Figure 8:
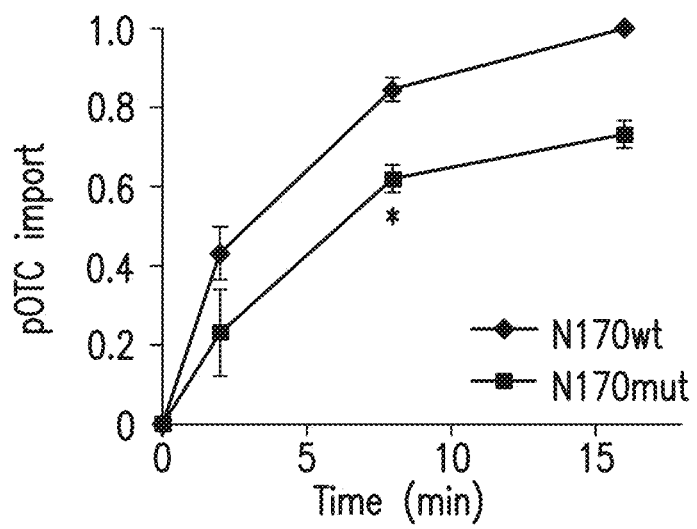
Figure 8:
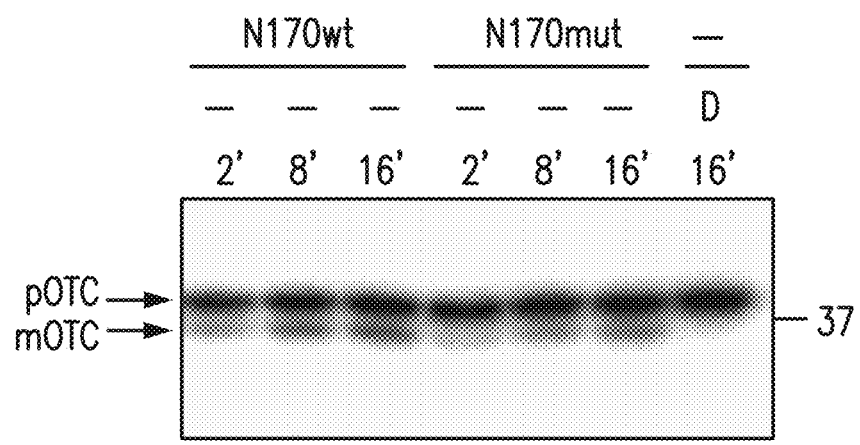

FIG. 8. N-terminal mutant Htt fragments impair mitochondrial protein import. Mitochondria were prepared from rat striatal ST14A cells transiently transfected with the plasmid encoding the N-terminal 170-amino acid fragments of wild-type (N170 wt) or mutant (N170mut) Htt and subjected to protein import assay. Expression of the N-terminal mutant Htt fragments decreased pOTC import into mitochondria (t test; *p<0.05, n=2 independent experiments). Mean±s.e.m. Representative gel image is shown (bottom). D: A mitochondrial uncoupler, 2,4-dinitrophenol was added to mitochondria before starting the import reaction.

FIGS. 9a-9c. Mutant Htt decreases the rate of mitochondria-targeted GFP accumulation in cells. (9a) Time-lapse imaging shows an increase in mitochondria-targeted GFP (mtGFP) fluorescence intensity over time in ST-HdhQ7/Q7 (Q7) cells expressing mtGFP using the BacMam system (Life Technologies) (green). Polarized active mitochondria were identified by mitochondria selective TMRM dye (red). Bar=10 µm. A representative result of 3 independent experiments is shown. See also Supplementary Video 1. (9b) mtGFP fluorescence intensity in Q7 cells in experiments (9a) was recorded and quantified using MetaMorph™ (Molecular Devices) and ImageJ (Wayne Rasband, NIH (rsb.info.nih.gov) software and was plotted against time. tlag: the time between transfection and the detection of GFP fluorescence. Slope=rate of mtGFP accumulation. (9c) The rate of increase in mtGFP fluorescence intensity in mutant ST-HdhQ111/Q111 (Q111) cells were significantly lower compared to that of WT Q7 cells (t test, n=49 cells per group, p=0.02, df=24, t=2.539).

Figure 10A:
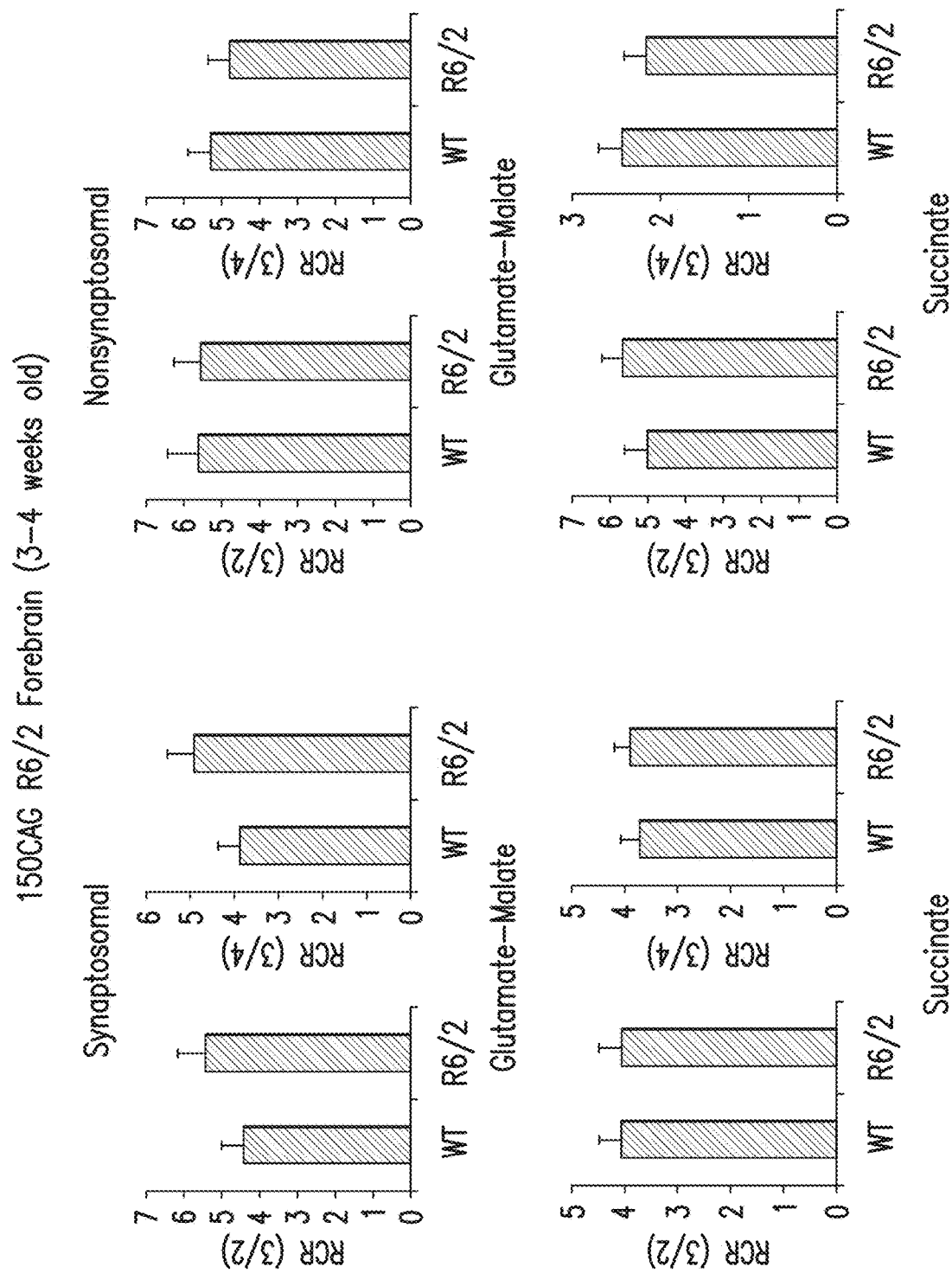
Figure 10B:
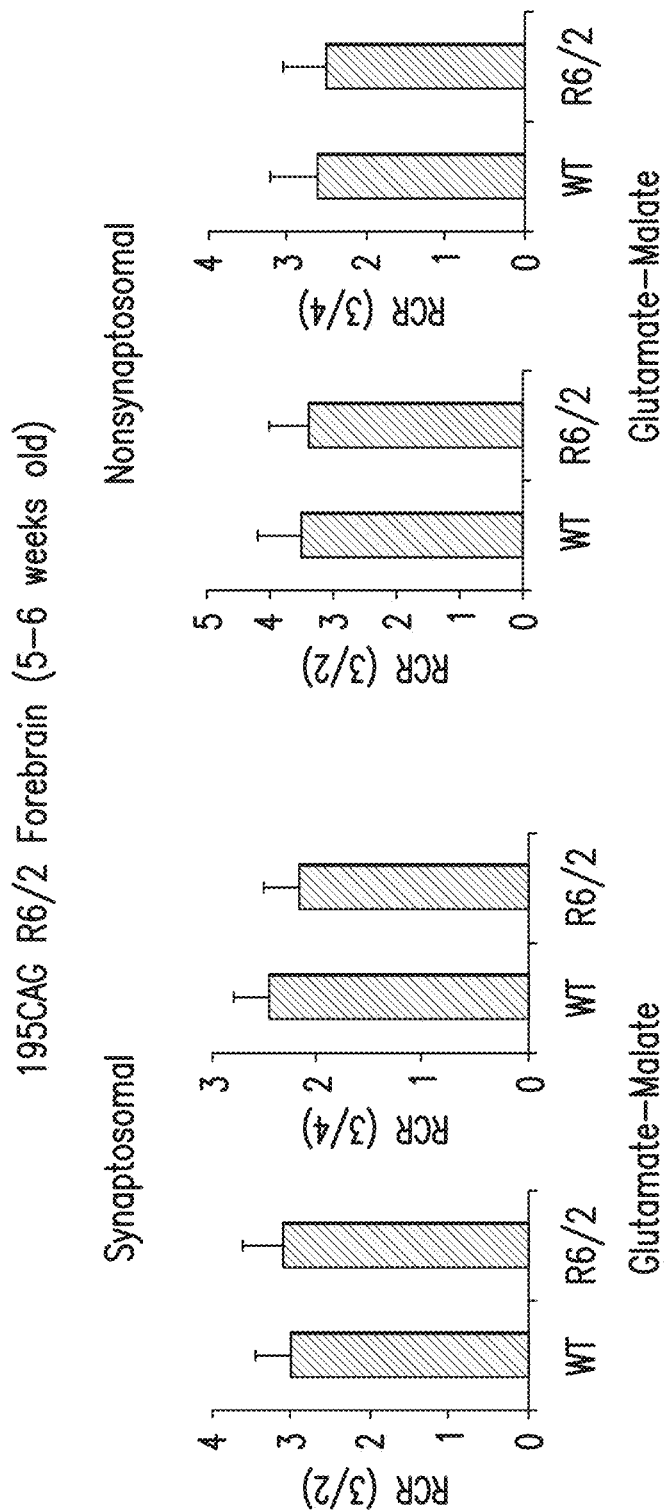

FIGS. 10a-10b. Respiratory function is not altered in forebrain mitochondria isolated from presymptomatic R6/2 mice. (10a) Synaptosomal and nonsynaptosomal mitochondria were isolated from 3-4 week-old 150CAG R6/2 and control WT mice. Respiratory function was measured using the complex I substrate, glutamate-malate (top), or complex II substrate, succinate (bottom). The respiratory control ratios (RCR) were calculated as the ratios of state 3 to state 2 respiration rates (RCR3/2) or the ratios of state 3 to state 4 respiration rates (RCR3/4). Both synaptosomal and non-synaptosomal mitochondria from 150CAG R6/2 forebrain show no significant difference in respiratory function compared to that of WT controls (n=3 and n=4 independent experiments for synaptosomal and nonsynaptosomal mitochondria, respectively). (10b) Synaptosomal and nonsynaptosomal mitochondria isolated from 5-6 week-old 195CAG R6/2 and control WT mice were subjected to respiratory function analysis with the complex I substrate as in (10a). Synaptosomal and nonsynaptosomal mitochondria from 195CAG R6/2 forebrain show no significant difference in respiratory function compared to that of WT controls (n=3 independent experiments for both synaptosomal and nonsynaptosomal mitochondria). Data (10a, 10b) are presented as mean+s.e.m.

Figures 11A, 11B, 11C:
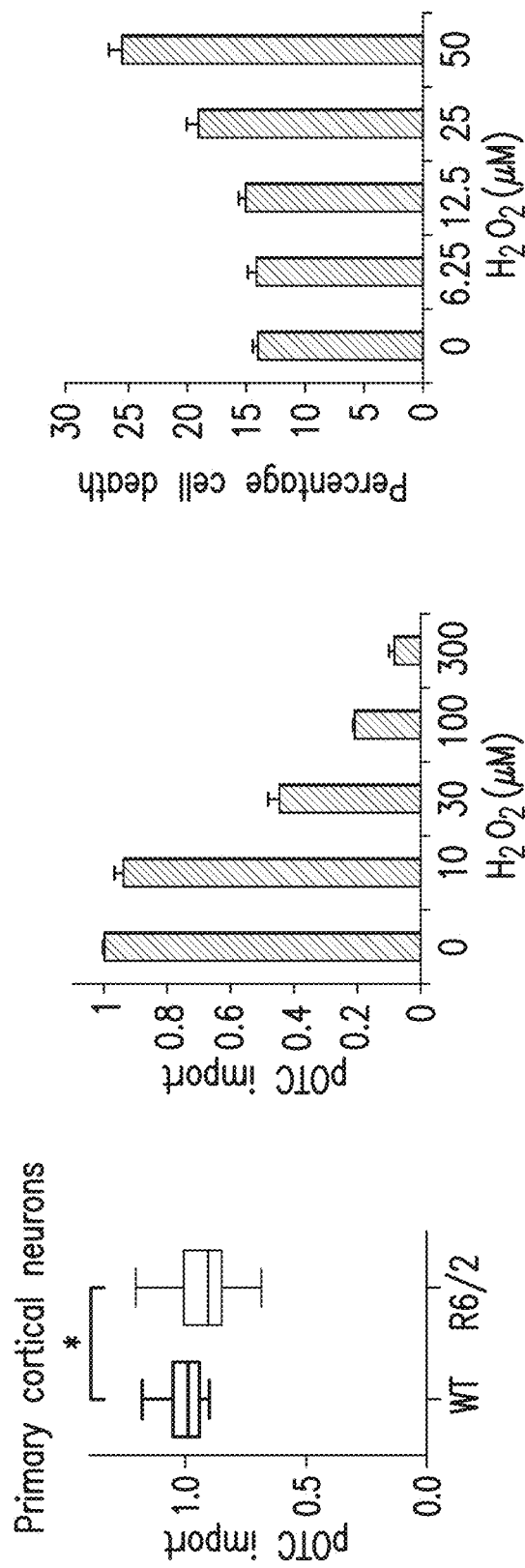

FIGS. 11a-11c. Mutant Htt expression and oxidative stress attenuate mitochondrial protein import in primary cortical neurons. (11a) HD mouse primary neurons expressing mutant Httex1 show impaired mitochondrial protein import. Primary cortical neurons were prepared from R6/2 and WT littermate embryos at E15.5. Neurons prepared from each embryo were plated into separate dishes. Mitochondria isolated from each individual culture at 7-8 days culture in vitro (DIV 7-8) were subjected to pOTC import assay (30 min at 25° C.). Imported mOTC was quantified, and the data were scaled to WT import (=1). R6/2 neuron mitochondria showed a significant reduction in pOTC import compared to that of WT neurons (t test; *p=0.0079, t=2.805, total 18 WT and 24 R6/2 neuron cultures prepared from distinct embryos in 6 independent experiments). The vertical bars represent the range of values. (b,c) Dose-response histogram for the effect of hydrogen peroxide (H2O2) on mitochondrial protein import and cell death in WT primary neurons. Mitochondria were isolated from primary cortical neurons (DIV 7-8) treated with the indicated concentrations of H2O2 for 2 h, and subjected to pOTC import assay (11b). Primary cortical neurons were incubated with the indicated concentrations of H2O2 for 1 day, and neuronal death was analyzed by lactate dehydrogenase (LDH) assay (11c). Data (11b, 11c) are presented as mean+s.e.m.

FIGS. 12a-12b. The effect of polyglutamine proteins on mitochondrial protein import and cell viability in primary neurons. (12a) Mouse primary cortical neurons were transduced with lentiviruses expressing Htt exon1 or the androgen receptor (AR N-terminal 127-amino acid fragment) with normal or pathological length of polyQ repeats, Htt25Q, Htt72Q, AR22Q, and AR65Q, at DIV 5. Mitochondria were isolated at DIV 10 and subjected to pOTC import assays (30 min at 25° C.). Imported mOTC was quantified, and the data were scaled to pOTC import in Htt25Q neuron mitochondria (=1). Primary neurons expressing Htt72Q showed diminished mitochondrial protein import compared to that of Htt25Q (ANOVA followed by Bonferroni post hoc test; *p<0.0001, F(3, 30)=14.76, n=8-10 assays using four to five neuron cultures from four independent experiments. In contrast, neurons expressing AR65Q did not exhibit a decrease in pOTC import compared to control neurons expressing AR22Q. The expression of the Htt and AR proteins was confirmed by immunoblotting (data not shown). (12b) Primary cortical neurons infected with lentiviruses at DIV 5 as in (12a) were subjected to MTS assays at DIV 14. Neurons expressing Htt72Q and AR65Q showed decreased mitochondrial metabolic activity compared to those expressing Htt25Q and AR22Q, respectively (ANOVA followed by Bonferroni test; *p<0.0001 compared to their WT counterparts, F(3, 79)=35.95, n=20-21 neuron cultures from three independent experiments).

Figure 13A:
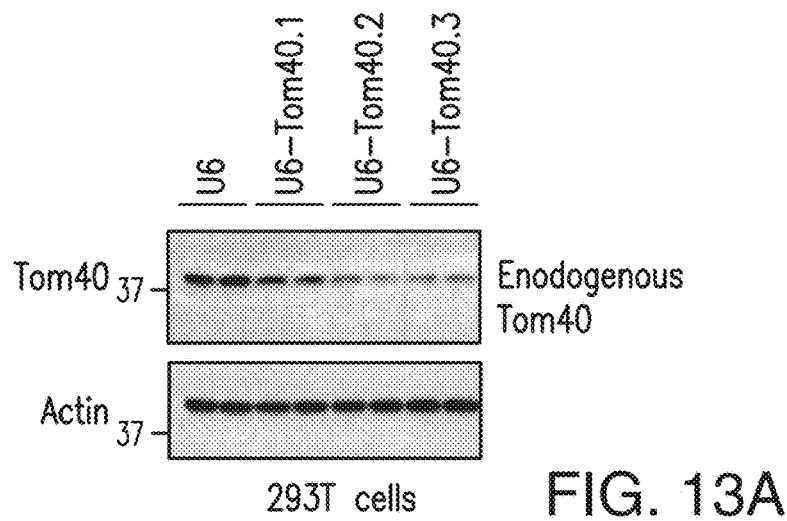
Figure 13B:
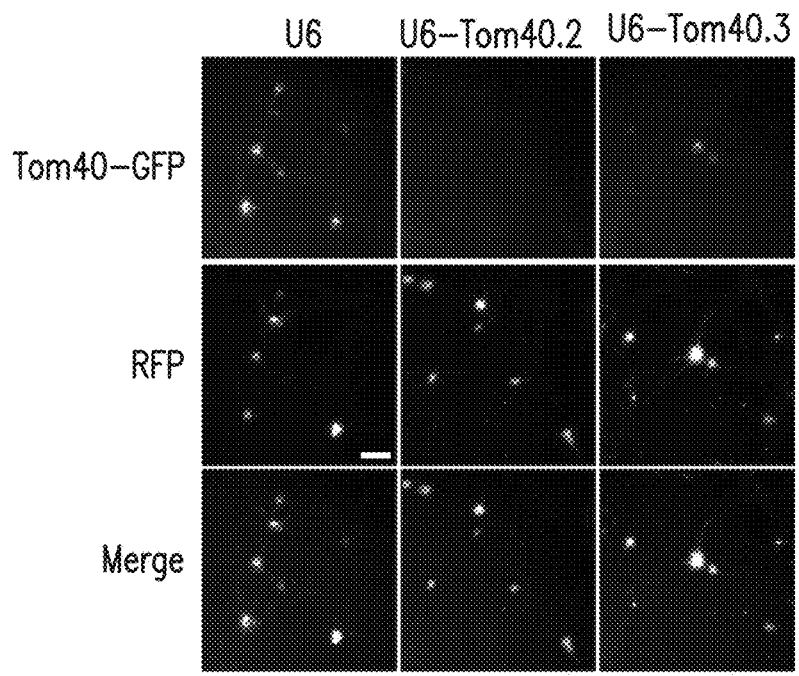
Figure 13C:
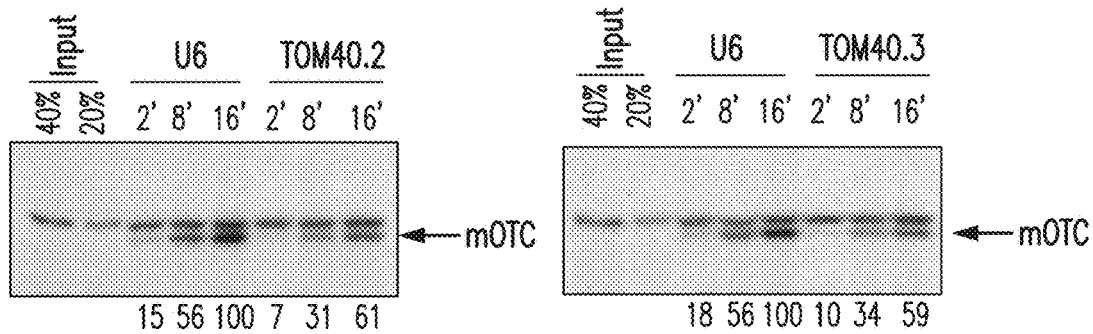

FIGS. 13a-13c. Tom40 knockdown reduces Tom40 protein levels and mitochondrial protein import. (13a) Lysates from 293T cells transfected with three distinct Tom40 RNAi plasmids (U6-Tom40.1, U6-Tom40.2, and U6-Tom40.3) or control U6 plasmid were immunoblotted with indicated antibodies. The U6-Tom40.1 plasmid had little to no effect on Tom40 levels and was not used for further analysis. (13b) Primary cortical neurons cotransfected with Tom40-GFP and RFP expression plasmids together with the Tom40 RNAi (U6-Tom40.2 or U6-Tom40.3) or control U6 plasmid were fixed and subjected to fluorescence microscopy. Bar=50 Tom40 RNAi reduced Tom40 protein levels in primary neurons. (13c) 293T cells transfected with the indicated Tom40 RNAi plasmids or control U6 plasmid were subjected to pOTC import assay. Imported mOTC was quantified, and data were scaled to imported mOTC in control U6 mitochondria at the maximum reaction time (=100).

Figure 14:
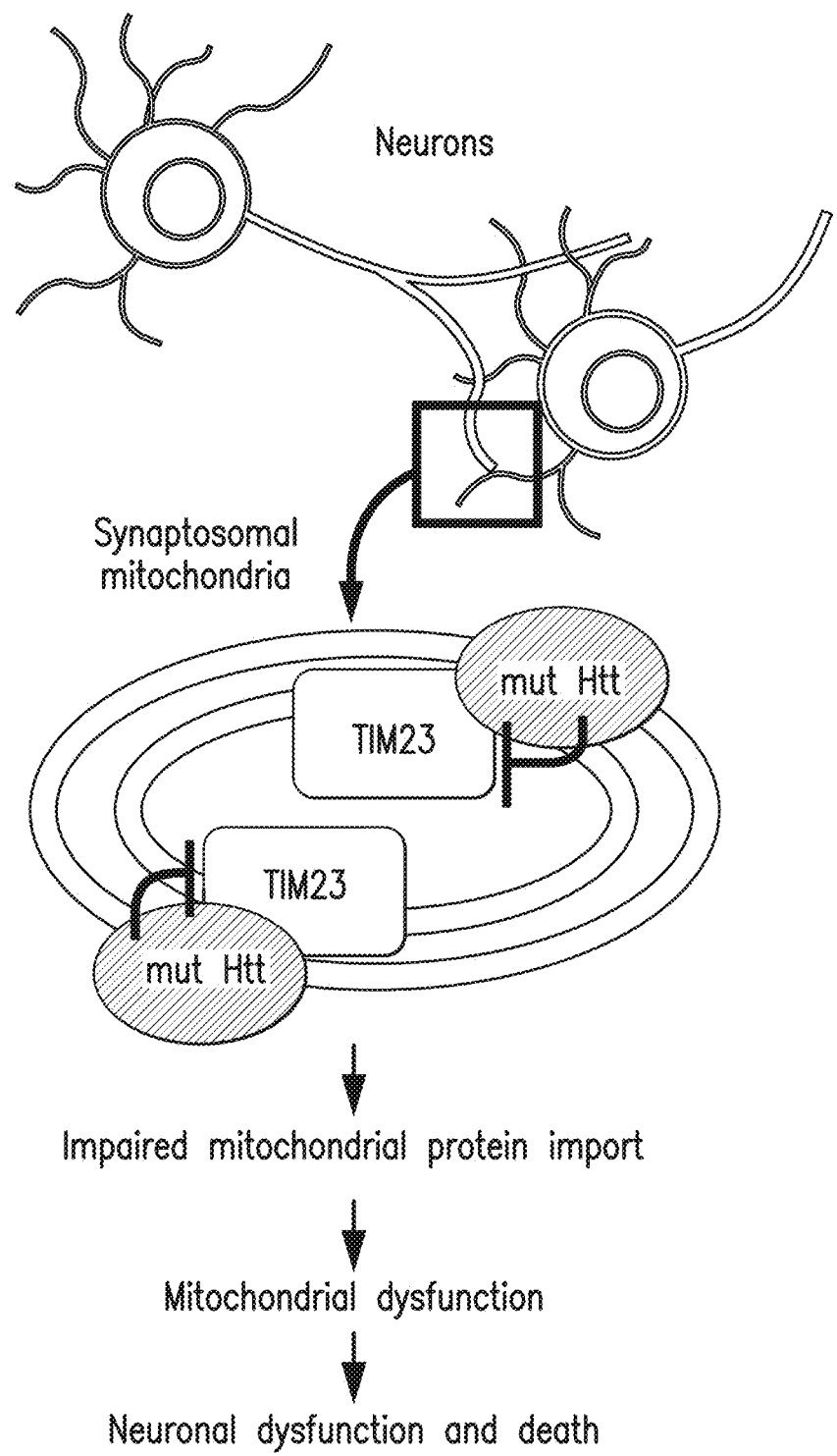

FIG. 14. A model for the mutant Htt-induced mitochondrial protein import defect. Mutant Htt binds the TIM23 complex and prevents the import of nuclear-encoded proteins into neuronal mitochondria early in HD pathogenesis, causing mitochondrial dysfunction and subsequent neuronal dysfunction and death in HD. Inhibition of mitochondrial protein import in R6/2 mice is tissue- and age-dependent.

FIG. 15. Full-length images of blots and gels depicted in FIGS. 1d-1g, 2a, 2c, 3a, 3c, 5a, 5f, and 5j.

Figure 16:
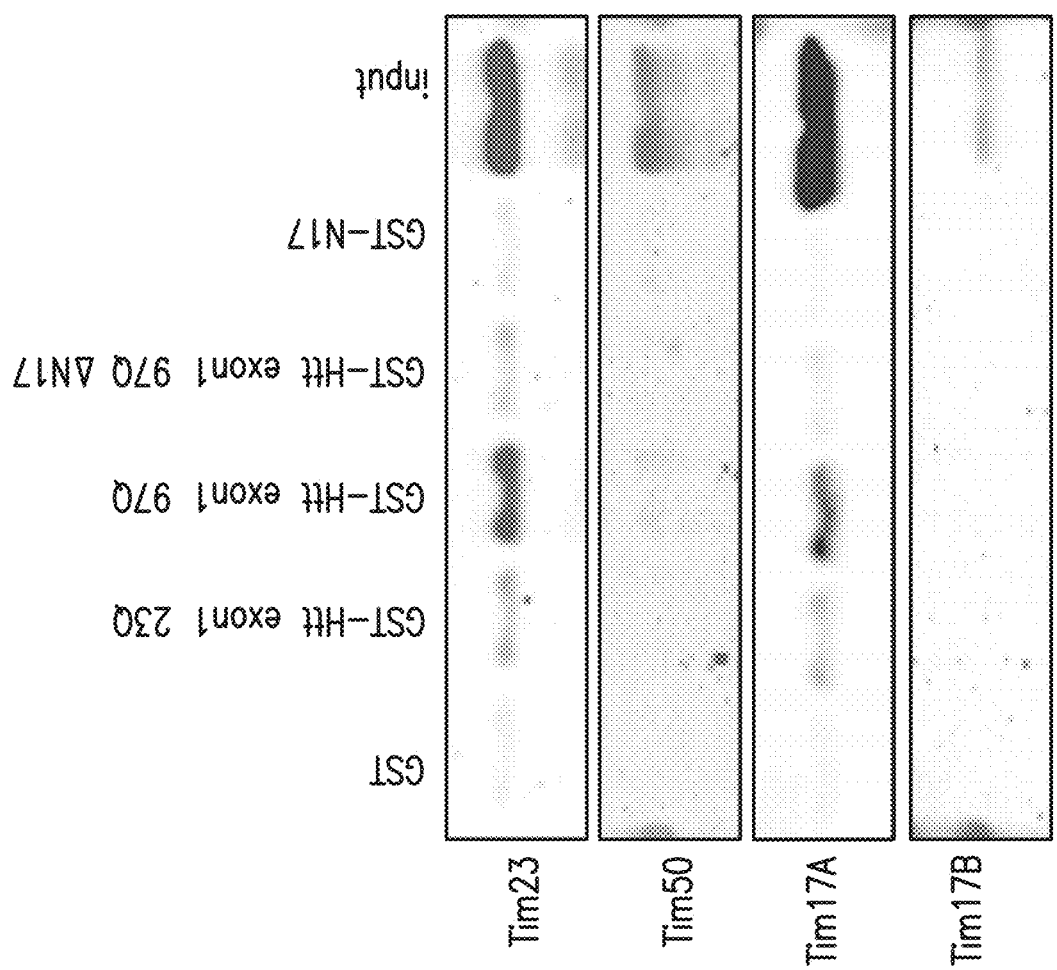

FIG. 16. GST Pull down assay shows that TIM23 subunits bind to mutant Htt. TIM23 subunit proteins were incubated with GST-Httex1 proteins (97Q, 23Q, 97QΔN17, and N17) and captured with GSH sepharose beads. After extensive wash, bound proteins were subjected to SDS-PAGE followed by immunoblotting. Each TIM23 subunit protein was probed with subunit specific antibodies. The blots were later stripped and reprobed with Huntingtin (1C2) antibody and GST antibody to confirm that equal amounts of proteins were loaded into each well of the gel (coomassie Brilliant Blue R-250 stain of SDS-PAGE was also performed to confirm protein loading). Tim23 binds GST-Httex1-97Q protein, but showed minimal binding to GST-Httex1-23Q protein. Tim17A protein exhibited some binding to GST-Httex1-97Q protein. Tim50 bound little to no GST-Httex1-97Q protein, and Tim17B did not bind to any Huntingtin proteins. The N-terminal 17 amino acid deleted Huntingtin protein (GST-Httex1-97Q ΔN17) and GST tagged N terminal 17 amino acids of Huntington protein (GST-N17) did not bind to any Tim proteins.

Figure 17:
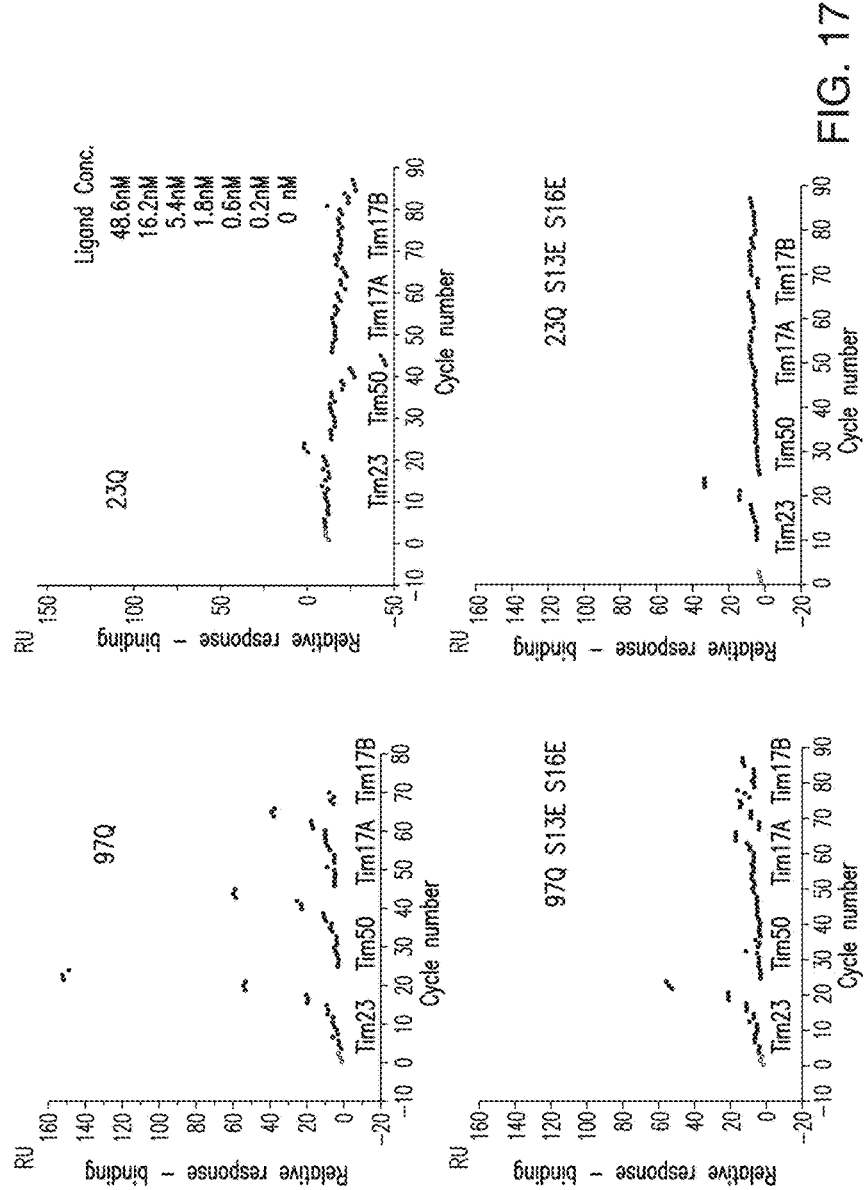

FIG. 17. Surface Plasmon Resonance (SPR) Biacore™ analysis showing that Tim proteins bind less strongly to S13E and S16E phosphomimetic 97Q. Tim 23 bound GST-Httex1-97Q with high affinity, but exhibited reduced affinity for the 97Q phosphomimetic GST-Httex1-97Q S13E S16E protein. In contrast, Tim 23 exhibited low affinity for GST-Httex1-23Q, which increased when 23Q was mutated to the S13E, S16E phosphomimetic GST-Httex1-23Q S13E S16E protein.

5. DETAILED DESCRIPTION OF THE INVENTION

The present invention relates to methods of inhibiting neurodegeneration in a subject suffering from or genetically at risk and/or destined to develop Huntington's Disease (HD) comprising increasing, in neurons of the subject, the activity of the TIM23 mitochondrial protein import complex. It is based, at least in part, on the discoveries that there is an interaction between mutant Huntingtin (Htt) protein and the TIM23 mitochondrial protein import complex, whereby import of protein into mitochondria is inhibited.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

For clarity of description and not by way of limitation, the detailed description of the invention is divided into the following subsections:

(i) TIM23 mitochondrial protein import complex and;
(ii) methods of treatment.

5.1. TIM23 Mitochondrial Protein Import Complex

In certain non-limiting embodiments, the invention provides for a method of treating and/or inhibiting the progression of Huntington's Disease in a subject, and also a method of inhibiting neurodegeneration in a neuron expressing mutant Htt, comprising decreasing the interaction between the mutant Htt and TIM23 mitochondrial complex or a subunit thereof (for example, Tim23, Tim50 and/or Tim17a protein(s)).

In certain non-limiting embodiments, human Tim23 is a protein having an amino acid sequence as set forth in NCBI Accession No. NP_006318, or a sequence at least 95 percent homologous thereto or at least 99 percent homologous thereto (homology, as that term is used herein, may be measured using standard software such as BLAST or FASTA), and is encoded, for example, by a nucleic acid having a sequence as set forth in NCBI Accession No. NM_006327, or a sequence at least 95 percent homologous thereto or at least 99 percent homologous thereto (homology, as that term is used herein, may be measured using standard software such as BLAST or FASTA).

In certain non-limiting embodiments, human Tim50 is a protein having an amino acid sequence as set forth in NCBI Accession No. NP_001001563, or a sequence at least 95 percent homologous thereto or at least 99 percent homologous thereto (homology, as that term is used herein, may be measured using standard software such as BLAST or FASTA), and is encoded, for example, by a nucleic acid having a sequence as set forth in NCBI Accession No. NM_001001563, or a sequence at least 95 percent homologous thereto or at least 99 percent homologous thereto (homology, as that term is used herein, may be measured using standard software such as BLAST or FASTA).

In certain non-limiting embodiments, human Tim17a is a protein having an amino acid sequence as set forth in NCBI Accession No. NP_006326, or a sequence at least 95 percent homologous thereto or at least 99 percent homologous thereto (homology, as that term is used herein, may be measured using standard software such as BLAST or FASTA), and is encoded, for example, by a nucleic acid having a sequence as set forth in NCBI Accession No. NM_006335, or a sequence at least 95 percent homologous

5.2. Methods of Treatment

The present disclosure relates to a method of inhibiting neurodegeneration in a neuron expressing mutant Htt, comprising decreasing an interaction between the mutant Htt and a TIM23 mitochondrial complex or a subunit thereof (for example, Tim23, Tim50 and/or Tim17a protein(s)).

In certain non-limiting embodiments, the Huntingtin protein (Htt) is a human Huntingtin (Htt) protein having an amino acid sequence as set forth in NCBI Accession No. NP_002102, or a sequence at least 95 percent homologous thereto or at least 99 percent homologous thereto (homology, as that term is used herein, may be measured using standard software such as BLAST or FASTA), and is encoded, for example, by a nucleic acid having a sequence as set forth in NCBI Accession No. NM_002111, or a sequence at least 95 percent homologous thereto or at least 99 percent homologous thereto (homology, as that term is used herein, may be measured using standard software such as BLAST or FASTA).

In certain embodiment, a mutant Htt protein is an Htt protein that is encoded by an htt gene comprising repeated CAG (cytosine-adenine-guanine) repeats at the 5' end of the gene, wherein the expressed mutant Htt protein comprises 20 or more glutamine repeats as a result of the CAG repeats. In certain embodiments, the mutant Htt protein comprises 20 or more glutamine repeats (i.e., 20Q). In other embodiments, the number of glutamine repeats is 23 or more, 25 or more, 30 or more, 35 or more, 40 or more, 45 or more, 50 or more, 55 or more, 60 or more, 65 or more, 70 or more, 75 or more, 80 or more, 85 or more, 90 or more, 95 or more, or 100 or more. In certain embodiments, the mutant Htt protein comprises 97 or more glutamine repeats (i.e., 97Q). In certain non-limiting embodiments, the mutant Htt is a mutant human Htt associated with Huntington's Disease or a homologous corresponding non-human protein. In other non-limiting embodiments, the mutant Htt protein comprises non-phosphorylated serine amino acids at positions S13 and S16.

In certain embodiments, "decreasing an interaction between mutant Htt and TIM23 mitochondrial complex" includes decreasing an interaction such as, but not limited to, a physical interaction, protein-protein binding interaction, covalent interaction, and/or non-covalent interaction.

In certain non-limiting embodiments, an interaction between a mutant Htt and a TIM23 complex is decreased by introducing into or providing to the neuron an agent that competes with TIM23 complex for mutant HTT binding.

In certain non-limiting embodiments, the invention provides for a method of inhibiting neurodegeneration in a neuron expressing mutant Htt, comprising increasing the amount, activity, or functionality of a TIM23 complex or a subunit thereof (for example, Tim23, Tim50 and/or Tim17a protein(s)) in the neuron. For example, the increased activity may be the transport of protein into a mitochondrion of the neuron. In other embodiments, the increased activity may be increased mitochondria metabolic activity.

In certain embodiments, the agent is contacted to the neuron in an amount effective to decrease an interaction between a mutant Htt and a TIM23 complex. In other embodiments, the agent is contacted to the neuron in an amount effective to increase the amount, activity, or functionality of a TIM23 complex, for example, an increase in protein import into mitochondria of the neuron or an increase in mitochondria metabolism.

In one non-limiting embodiment, the agent comprises a TIM23 (or subunit thereof) protein and/or nucleic acid, as well as agents that promote TIM23 functionality, for example, agents that increase the import of proteins into mitochondria, or increase mitochondria metabolism.

In certain non-limiting embodiments, the neuron is a human neuron. In alternative non-limiting embodiments, the neuron is a non-human animal neuron, such as but not limited to a mouse neuron, rat neuron, hamster neuron, guinea pig neuron, dog neuron, cat neuron, non-human primate neuron, etc.

In certain non-limiting embodiments, the neuron is in a human subject. In alternative non-limiting embodiments, the neuron is in a non-human subject, such as, but not limited to, a rodent subject, a canine subject, a feline subject, or a non-human primate subject.

In certain non-limiting embodiments, the invention provides for a method of treating and/or inhibiting the progression of Huntington's Disease in a subject, comprising administering, to the subject, an agent that decreases the interaction between mutant Htt and a TIM23 complex, and/or increases the activity of the TIM23 complex. "Treating" Huntington's Disease, as that term is used herein, means one or more of reducing neurological symptoms (physical or cognitive), slowing the progression of neurological symptoms (physical or cognitive, for example, but not limited to, slowing the progression of motor symptoms such as choreiform movements and/or slowing the progression of dementia), and/or prolonging survival, relative to subjects not receiving such treatment.

In certain non-limiting embodiments the human subject is suffering from or genetically at risk for/destined to develop Huntington's disease. For example, the human subject may have a family member who suffers from or has suffered from Huntington's Disease.

In certain embodiments, the method of treating and/or inhibiting the progression of Huntington's Disease in a subject comprises administering an agent in an amount effective to decrease an interaction between a mutant Htt and a TIM23 complex. In other embodiments, the agent is administered in an amount effective to increase activity of a TIM23 complex, for example, an increase in protein import into mitochondria of the subject or an increase in mitochondria metabolism.

In certain non-limiting embodiments, the interaction between mutant Htt and the TIM23 mitochondrial complex is decreased, and/or the activity of the TIM23 complex is increased, as described herein, by increasing the amount of TIM23 complex, for example but not limited to, by increasing the amount of Tim23, Tim50, and/or Tim17a subunits. For example but not by limitation, the amount of Tim23, Tim50 and/or Tim17a subunits may be increased by increasing the amount of Tim23 (also referred to in the art as Timm23 mRNA), Tim50 (also referred to in the art as Timm50 mRNA) and/or Tim17a (also referred to in the art as Timm17a mRNA) mRNAs, respectively, in the neuron or subject described herein. For example but not by limitation, the amount of Tim23, Tim50 and/or Tim17a mRNA(s) may be increased by introducing, into the neuron, one or more nucleic acid encoding Tim23, Tim50 and/or Tim17a, for example one or more DNA molecule comprising nucleic acid encoding Tim23, Tim50 and/or Tim17a operably linked to one or more promoter that is constitutively or inducibly active in the neuron. For example, Tim23 can be human Tim23 and/or Tim23 of the same species as the neuron or subject, Tim50 can be human Tim50 and/or Tim50 of the same species as the neuron or subject, and/or Tim17a can be human Tim17a of the same species as the neuron or subject. Said nucleic acid(s) may optionally be introduced via one or more vector, such as one or more viral vector, or any other vector, as are known in the art.

In other non-limiting embodiments, the agent used in the methods of the present disclosure comprises a TIM23 protein complex, or a TIM23 protein complex subunit selected from the group consisting of Tim23, Tim50, Tim17a, and combination thereof. In other embodiments, the agent comprises a protein or protein fragment that exhibits TIM23 complex activity, for example, increases mitochondria protein import or mitochondria metabolism. Such proteins may be modified by any means known in the art. The proteins can be modified by, for example but not limited to, PEGylation, glycosylation, carboxylation, hydroxylation, sulfation and/or amidation.

In certain non-limiting embodiments, the agent administered according to the methods of the present disclosure is an agent that phosphorylates proteins, for example, a kinase, such as but not limited to, a serine/threonine protein kinase. In certain embodiments, the agent comprises a phosphorylase kinase enzyme. In certain embodiments, the agent comprises a protein kinase A enzyme, protein kinase B enzyme, protein kinase C enzyme, Mos/Raf kinase, mitogen-activated protein kinase (MAPK), casein kinase 2, and/or $Ca^+$/calmodulin-dependent protein kinase. The agent can be administered in an amount effective to phosphorylate a mutant Htt protein, for example, to phosphorylate serine amino acids in the mutant Htt protein. In certain non-limiting embodiments, the agent phosphorylates S13 and/or S16 of the mutant Htt protein.

The present disclosure further provides for kits comprising an agent that can decrease interactions between Htt and a TIM23 complex, increase activity of a TIM23 complex, reduce or inhibit neurodegeneration, and/or phosphorylate a mutant Htt protein.

6. EXAMPLES

The presently disclosed subject matter will be better understood by reference to the following Examples, which are provided as exemplary of the invention, and not by way of limitation.

6.1 Example 1: Inhibition of Mitochondrial Protein Import by Mutant Huntingtin 6.1.1 Materials and Methods HD Transgenic R6/2 Mice.

R6/2 mice, which carry the promoter sequence and exon 1 of a mutant human HTT gene with approximately 150 CAG repeats, were obtained from JAX (Bar Harbor, Me.). A colony was maintained by breeding R6/2 males with B6CBAF1 females (JAX). R6/2 mice with a spontaneous expansion of CAG repeats, 195-205 CAG repeats, were found in the colony and further maintained. PCR genotyping was performed using a primer set (CGGCT-GAGGCAGCAGCGGCTGT (SEQ ID NO:1) and GCAGCAGCAGCAGCAACAGCCGCCACCGCC) (SEQ ID NO:2) as described (18). To maintain mice carrying the same number of CAG repeats, a second PCR analysis was also conducted using a primer set amplifying across the CAG repeats, (ATGAAGGCCTTCGAGTCCCT-CAAGTCCTTC (SEQ ID NO:3) and GGCGGCTGAG-GAAGCTGAGGA) (SEQ ID NO:4). The precise CAG repeat length in the R6/2 mice was determined by ABI377 sequencer using tail DNA (Laragen Inc., Culver City, Calif.). All live vertebrate experiments were performed in compliance with the National Institutes of Health Guide for the Care and Use of Laboratory Animals. Animal protocols were approved by the Institutional Animal Care and Use Committees of the University of Pittsburgh and Washington University.

Antibodies.

Rabbit polyclonal anti-Tom40 (H-300, sc-11414, Santa Cruz Biotechnology), rabbit polyclonal anti-SOD2 (ab13534, Abcam, Cambridge Mass.), rabbit polyclonal anti-Tim23 (ab116329, Abcam), rabbit polyclonal anti-DRP1 (ab54038, Abcam), rabbit monoclonal anti-Tim50 (ab109436, Abcam), mouse monoclonal anti-Tim23 (611222, BD Transduction Laboratories), mouse monoclonal anti-β-galactosidase (β-gal) (Z378B, Promega), mouse anti-actin (A5411, Sigma) and mouse anti-Flag M2 (F3165, Sigma) antibodies were purchased. Anti-cleaved caspase-3 (Asp175) antibody (9661, Cell Signaling Technology), specifically recognizing active caspase-3, and mouse monoclonal anti-Htt antibody EM48 (MAB5374, Millipore), generated against the first 256 amino acids of human Htt with a deletion of the polyQ tract, were purchased. Mouse monoclonal anti-Htt (MAB5492, Millipore), mouse anti-expanded polyglutamine (clone 1C2; MAB1574, Millipore) and rabbit polyclonal anti-GFP (A6455, Life Technologies (Molecular Probes)) antibodies were purchased.

DNA Constructs.

A bacterial expression mutant Htt construct encoding human mutant HTT exon 1 with 97 polyglutamine repeats, pGEX4T3-Httex1-97Q, was generated by standard subcloning. The bacterial expression construct forGST-Httex1-23Q (ref. 24) was kindly provided by M. Lesort (University of Alabama, Birmingham, Ala.). GFP-tagged human N170 WT and mutant Htt expression plasmids was provided by M.E. MacDonald (Harvard Medical Center, Boston, Mass.). Tim23 and Tom40 shRNA plasmids were produced by insertion of annealed oligonucleotides containing the following targeted sequences into pBSU6-GFP and pBSU6, respectively: pBSU6-GFP-Tim23: CGGAG-GAAGTAGCAACAAA (SEQ ID NO:5); pBSU6-Tom40.1: GGAGTGCCACCGGAAGTGCAA (SEQ ID NO:6); pBSU6-Tom40.2: GCTGAGTCCCAC AGAGGCGTT (SEQ ID NO:7); pBSU6-Tom40.3: GGCACTGT-CATGTCTCTAGCT (SEQ ID NO:8). All constructs were confirmed by sequencing. Lentivirus-based Tim23 RNAi constructs (pLKO.1-puro), developed at the Broad Institute of MIT and Harvard, were obtained (RNAi Core, Washington University). The Tim23 targeted sequences are as follows: pLKO.1-Tim23.a: GCTGTGACAAAGATCATGGAT (SEQ ID NO:9); pLKO.1-Tim23.b: GCCTGGTCCAAAC-CAAGAAAT (SEQ ID NO:10); pLKO.1-Tim23.c: CGGTCTTCGTTT AGGATTGAA (SEQ ID NO:11). Tom40-GFP expression plasmid47 was kindly provided by M. Ryan (La Trobe University, Melbourne, Australia). Mouse Timm23, Timm50 and Timm17a cDNAs were cloned by reverse transcription—PCR from mouse brain RNA and subcloned into lentiviral expression plasmid pRRLsinPGK (Hope Center Viral Vectors Core, Washington University). Lentiviral expression plasmids containing Httex1-25Q and Httex1-72Q constructs under the control of the mouse PGK promoter (mPGK-Httex1-25Q and mPGK-Httex1-72Q) were kindly provided by D. Krainc (Harvard Medical Center, Boston, Mass.). cDNA clones encoding the N-terminal 127-amino acid fragment of androgen receptor (AR) containing 22Q and 65Q were kindly provided by M.

Diamond (Washington University, St. Louis, Mo.) and were subcloned into the mPGK lentiviral expression vector.

Cell Culture, DNA Transfection and Lentiviral Transduction.

Mouse primary cortical and striatal neurons from embryonic day (E) 15.5 Swiss Webster mouse fetuses were cultured in plating medium (minimal essential medium (MEM), 10% FBS, 0.45% glucose, 1 mM sodium pyruvate, 2 mM glutamine and penicillin/streptomycin) for 3 h and then maintained in serum-free Neurobasal medium containing B27 supplement (Life Technologies), 0.5 mM glutamine and 25 μM glutamate for the first 3 d in a humidified incubator (37° C. in 5% CO2). Half of the medium was replaced with Neurobasal medium with B27 and 0.5 mM glutamine every 3 d. At 5 d in vitro (DIV 5), neurons were transfected with pBSU6-GFP plasmids or cotransfected with pBSU6 RNAi and β-gal plasmids using Lipofectamine 2000 (Life Technologies). Primary cortical and striatal neurons were infected with Tim23 RNAi lentiviruses at DIV 5 and subjected to mitochondrial metabolic activity assays using MTS (Promega) or cell death assays at DIV 12. For the immunoblotting experiments evaluating Tim23 knockdown efficiency in transduced neurons, neurons were harvested at DIV 10. For the rescue experiments, mouse primary cortical neurons plated on 6-cm or 96-well plates were infected with lentiviruses expressing Httex1-25Q, Httex1-72Q or control empty vector at DIV 5. On the next day (DIV 6), the same neurons were infected with Tim23, Tim17a and Tim50 lentiviruses or GFP lentivirus as control. Viral copy number was adjusted for transduction of neurons on the basis of titer measured using the Lenti-X qRT-PCR titration kit (Clontech). Neurons on 6-cm plates were harvested for mitochondrial protein import assay at DIV 10; neurons on 96-well plates were subjected to MTS assay or cell death assay at DIV 14.

R6/2 and littermate WT primary cortical neurons were prepared from E15.5 embryos, which were obtained from pregnant WT B6CBA females mated with a 195CAG R6/2 male. Neurons obtained from each embryo were cultured separately on poly-1-lysine-coated plates and subjected to in vitro pOTC import assay on DIV 7-8. The genotype of cultured neurons was determined by PCR using embryonic tail DNA.

Mouse knock-in striatal cell lines, ST-Hdh$^{Q111/Q111}$ and ST-Hdh$^{Q7/Q7}$ (ref. 48), were obtained from M.E. MacDonald (Harvard Medical Center, Boston, Mass.) and were cultured at 33° C. in 5% CO2 in Dulbecco's modified Eagle's medium (DMEM) containing 10% FBS and 1 mM sodium pyruvate. The immortalized rat striatal cell line ST14A (ref. 49), as well as ST14A stably expressing the N-terminal 548 amino acid fragments of WT or mutant Htt, which were obtained from E. Cattaneo (Milano, Italy), were cultured at 33° C. in 5% CO2 in DMEM containing 10% FBS and 0.1 mM nonessential amino acids (Life Technologies). These striatal cell lines stably express the temperature-sensitive SV40 large T antigen and stop dividing when cultured at the nonpermissive temperature of 37° C. Cells were cultured at 37° C. for 24-36 h before mitochondrial isolation for in vitro pOTC import assays. Human embryonic kidney (HEK) 293 cells were cultured at 37° C. in 5% CO2 in DMEM containing 10% FBS. For transient transfection experiments with cell lines, cells were grown on poly-1-lysine coated plates and transfected with indicated plasmids using Lipofectamine 2000 (Life Technologies). Mitochondria-targeted GFP (mtGFP), which contains a presequence from E1-α pyruvate dehydrogenase, was expressed in ST-Hdh cells using the BacMam system (Life Technologies).

Cell Death Assays.

Primary neurons infected with Tim23 shRNA or control luciferase shRNA lentivirus at DIV 5 were fixed 7 d after infection. Nuclei were stained with Hoechst 33342, and neurons were assessed in a blinded fashion for cell death by scoring condensed or fragmented nuclei. Primary neurons plated in a 24-well plate were transfected with Tom40 shRNA or control pBSU6 plasmid along with β-gal expression plasmid at DIV 5, fixed 3 d after transfection and subjected to indirect immunofluorescence with anti-β-gal antibody and nuclear DAPI staining. β-gal-positive neurons were assessed for cell death as described above. Experiments were performed in duplicate or triplicate in three or more independent experiments.

Isolation of Mitochondria.

Brain synaptosomal and nonsynaptosomal mitochondria were isolated from R6/2 mice and sex-matched littermate or sex- and age-matched WT mice using differential centrifugation followed by discontinuous Percoll gradient centrifugations as described (50). Briefly, 2-3 mouse forebrains were homogenized in IM buffer (5 mM HEPES-Tris (pH 7.4), 225 mM sucrose, 75 mM mannitol and 1 mM EGTA) and then centrifuged at 1,300 g for 3 min. The supernatant was spun at 12,700 g for 10 min. The resulting pellet was resuspended in 15% Percoll, laid on top of 24% and 40% Percoll, and subjected to centrifugation at 30,700 g for 8 min. The band at the boundary between 24% and 40% Percoll contains nonsynaptosomal mitochondria and the band in the 24% Percoll contains the fraction enriched in synaptosomes. The nonsynaptosomal mitochondrial fraction was collected, washed with IM buffer to remove Percoll, spun down and resuspended in the IM buffer without EGTA. The synaptosomal fraction was diluted 1.5 times with IM buffer and placed in the nitrogen disruption vessel (45 ml; Parr Instrument, cat. no. 4639) and incubated on ice for 15 min at 1,500 p.s.i. The disrupted synaptosomal fraction was layered on top of 24% Percoll and centrifuged at 30,700 g for 8 min. The bottom fraction enriched with synaptosomal mitochondria was collected, washed with IM buffer, spun down and resuspended in IM buffer without EGTA. Isolated mitochondria were kept on ice and used for mitochondrial protein import assay and/or respiratory function assays within 3 h after preparation. Liver mitochondria were isolated as described previously (51). Mitochondria from primary cultured neurons or cell lines were isolated as described with a modification to the homogenization step (52). Cells were homogenized in mitochondrial isolation buffer by passing through a 23-G needle 15-20 times, and the homogenates were subjected to differential centrifugation (600 g and 8,000 g) to obtain the mitochondrial fraction.

Preparation of GST-Htt Exon 1 Fusion Proteins from Bacteria.

GST and GST-Htt exon 1 (GST-Httex1) fusion proteins were purified from transformed BL21star (DE3) cells (Life Technologies) as previously described (24). GST fusion proteins bound to glutathione 4B Sepharose beads (GE Healthcare) were eluted with 50 mM Tris buffer (pH 8) containing 10 mM reduced glutathione, and the purified proteins in the glutathione elution buffer were concentrated in PBS using AmiconUltra-10K (Millipore).

GST Pull-Down Assays and Protein Sequence Analysis by LCLC-MS/MS.

Mitochondria isolated from adult mouse forebrains were incubated with GST, GST-Httex1-23Q or GST-Httex1-97Q in the mitochondrial isolation buffer (3 mM HEPES-KOH, pH 7.6, 210 mM mannitol, 70 mM sucrose and 0.2 mM EGTA) for 1 h on ice and then lysed in TNE buffer (10 mM Tris, pH 8.0, 150 mM NaCl, 1 mM EDTA, 1% NP-40) containing protease inhibitors on ice for 30 min. Extracts were spun at 14,000 r.p.m. at 4° C., and clarified supernatants were incubated with glutathione 4B Sepharose beads (GE Healthcare) at 4° C. overnight. The glutathione beads were then washed extensively with ice-cold TNE buffer, and bound proteins were subjected to SDS-PAGE followed by immunoblotting analysis. For the samples subjected to mass spectrometry, glutathione bead-bound proteins from equal amounts (600 μg) of mitochondria were further washed with high stringency RIPA buffer following TNE buffer wash to decrease nonspecific interaction. Proteins were then eluted from the glutathione beads in SDS sample buffer, separated by SDS-PAGE and stained with Coomassie. Proteins in the gel were digested with trypsin and analyzed by mass spectrometry (LC-MS/MS) at the Taplin Biological Mass Spectrometry Facility (Harvard Medical School, Boston, Mass.).

Immunoprecipitation.

Cell or brain lysates were prepared in TNE buffer containing protease inhibitors and phosphatase inhibitors and immunoprecipitated with anti-Tim50 rabbit monoclonal antibody followed by protein A magnetic beads (Life Technologies). The immunoprecipitates were subjected to SDS-PAGE and immunoblotting with indicated antibodies, and the proteins were visualized using enhanced chemiluminescence (Pierce).

Mitochondrial pOTC Import Assay.

The assay was performed as previously described (52,53). Pre-ornithine transcarbamylase (pOTC) cDNA in pGEM-3Zf(+)-pOTC plasmid, which was kindly provided by M. Yano (Kumamoto University, Kumamoto, Japan), was transcribed and translated in vitro using the TNT-coupled reticulocyte lysate system (Promega) in the presence of 1-[$^{35}$S] methionine (PerkinElmer). Following translation, [35 S]methionine-labeled pOTC was incubated with isolated mitochondria at 25° C. for the indicated times, and mitochondria containing imported OTC were collected by centrifugation (9,000 g, 10 min) and subjected to SDS-PAGE. The radioactive polypeptides on the gel were visualized by fluorography with Amplify (GE Healthcare) followed by exposure to X-ray film. Cleaved mature OTC (mOTC), which represents the completion of import into the mitochondrial matrix and migrates faster than pOTC on SDS-PAGE, was quantified by ImageJ (NIH). The data are presented as the percentage of mOTC compared to input (total [$^{35}$S]pOTC amount added to each reaction) and scaled to imported mOTC in control mitochondria after the maximum reaction time (set equal to 1) unless otherwise specified. In the import assay with forebrain mitochondria, data are scaled to imported mOTC in control WT mitochondria at 60 min reaction time (which was set equal to 1).

Mitochondrial Respiration Measurements.

Respiration in isolated mitochondria was measured in buffer containing 125 mM KCl, 5 mM HEPES-KOH (pH 7.4), 2 mM KH2PO4, and 10 mM glutamate and malate or 10 mM succinate as respiratory substrates using the Oroboros Oxygraph-2k high-resolution respirometry system (Oroboros, Austria) equipped with two Clark-type electrodes. Respiration in the presence of substrates-only corresponds to resting state (state 2) respiration. The subsequent addition of ADP (100 μM) initiates ATP synthesis coupled to proton reentry across the membrane, which corresponds to ADP-stimulated (state 3) respiration. ADP exhaustion then leads to a reduction of the respiratory rate and corresponds to state 4 respiration. The respiratory control ratios (RCR), an index of the efficiency of coupled respiration to phosphorylate ADP, were calculated as the ratios of state 3 to state 2 respiration rates (RCR3/2) or the ratios of state 3 to state 4 respiration rates (RCR3/4) for both respiratory complex I- and complex II-dependent respiration using glutamate-malate and succinate, respectively.

Immunofluorescence Microscopy.

Cells were fixed in 4% paraformaldehyde in PBS for 20 min, permeabilized with 0.1% Triton X-100 in PBS for 15 min at room temperature and subjected to immunofluorescence with the indicated primary antibodies and secondary antibodies, Cy3-conjugated goat anti-mouse IgG (Jackson ImmunoResearch) and/or Alexa Fluor 488-conjugated goat anti-rabbit IgG (Molecular Probes) antibodies, according to standard protocols. Cell nuclei were labeled with DAPI or Hoechst 33342. Images were captured using SensiCam CCD camera with imaging software IPLab 4.0 (BD Biosciences) through a fluorescence microscope (Nikon) or using a confocal laser scanning microscope system (FluoView FV1000; Olympus, Inc.).

For immunostaining of human grade-2 HD and control age-matched caudate nucleus samples, sections (50 μm) were incubated with indicated antibodies in Tris buffer (pH 7) containing 0.3% Triton X-100 for 24-72 h at 4° C., followed by incubation with FITC-conjugated horse anti-rabbit IgG (Vector) and Cy3-conjugated donkey anti-mouse IgG (Jackson ImmunoResearch) antibodies. Digital imaging was performed using an IX81 microscope (Olympus, Inc.) equipped with an IX2-DSUA-SP confocal spinning disk and a 100× UPLSAPO objective (NA 1.40; Olympus, Inc.) and UIS dichromatic mirror and emission filter sets (Olympus, Inc.). Images were captured with a cooled charge-coupled device camera (Orca R2; Hamamatsu). Optical sections and three-dimensional image reconstructions were performed using Metamorph software (Molecular Devices, LLC). Images were captured at 0.2-μm intervals for 50 focal planes, and stacks were deconvolved with a constrained iterative algorithm.

Time-Lapse Live Cell Imaging.

Mouse primary cortical neurons were plated at 0.3×106 cells per well of 24-well #1.5-coverglass-bottom plates (In Vitro Scientific) and transfected with a Tim23 RNAi or control pBSU6-GFP plasmid at DIV 5. Three days after transfection, neurons were loaded with the red fluorescent TMRM dye (200 nM) and the cell membrane-impermeable, far-red nuclear dye RedDot2 and placed into an on-stage incubation chamber (WSKM-FI; Prior Scientific, Rockland, Mass.) at 37° C. and 5% CO2. Sets of images were acquired every 1.5 h using an Olympus IX81-DSU inverted confocal microscope with UPLSAPO 40× air 0.95 NA lens, Lumen 200 (Prior Scientific) light source, H117 motorized linear encoded x-y stage (Prior Scientific) and Hamamatsu Orca R2 CCD camera and analyzed using Metamorph image acquisition software (Molecular Devices). For quantitative analyses, GFP-positive transfected neurons were assessed over time for the loss of TMRM signal from mitochondria and the appearance of RedDot2 signal in nucleus, which represent mitochondrial depolarization and cell death, respectively. Data collection and analysis were performed in a manner blinded to the conditions of the experiments.

Human Brain Tissues.

Postmortem striatal tissue specimens from three patients with neuropathological grade 2 HD (sex, age (years): male, 54; male, 46; female, 68) and three controls (female, 67; female, 57; male, 44) were subjected to immunohistochemical analysis. The brain specimens were received from the Bedford Veterans Administration Medical Center Brain Tissue Archive. The postmortem intervals did not exceed 15 h and were similar between controls and HD patients. Work involving human brain tissue samples was approved by the IRB and the Committee for Oversight of Research Involving the Dead at the University of Pittsburgh.

Statistics.

Statistical analyses were performed with Prism 6 and XLSTAT2012 software. Data are obtained from at least three independent experiments and expressed as mean±s.e.m. unless otherwise specified. The Student's t-test (unpaired, two-tailed) for parametric data and the Mann-Whitney U test for nonparametric data were used for analysis of two groups. Equal variance for parametric data was formally tested using an F-test. In experiments with more than two groups, analysis of variance (ANOVA) was performed followed by Fisher's least significant difference (three groups) or Bonferroni test (three groups or greater) for pairwise comparisons. For time-lapse imaging analysis, Kaplan-Meier curves were used to estimate survival function, and statistical comparisons between Tim23 knockdown and control neurons were made using the log-rank test. No randomization was used, but treatments and assays for different conditions were performed in a blinded fashion. No statistical methods were used to predetermine sample sizes, but our sample sizes are similar to those reported in previous publications (54).

6.1.2 Results

Mutant Htt Binds to the Mitochondrial Import Machinery.

Mutant Htt associates with mitochondria in the brain of various HD transgenic mice (9,10,15,16). To determine whether mutant Htt protein localizes to mitochondria in human brains affected by HD, we examined the caudate nucleus, the area most severely affected, from patients with grade 2 HD. Brain sections were subjected to immunohistochemistry with antibodies recognizing mitochondrial resident proteins, including a mitochondrial inner membrane translocase subunit, Tim23 and dynamin-related protein 1 (DRP1), and aggregated mutant Htt. Confocal immunofluorescence microscopy revealed localization of aggregated mutant Htt to mitochondria (FIG. 1a). Additionally, confocal microscopy identified partial colocalization of mutant Htt with mitochondrially targeted GFP (mtGFP) in mutant Htt knock-in mouse striatal cells (ST-Hdh$^{Q111/Q111}$) (FIG. 1b). These results suggest that mutant Htt may affect mitochondrial function by interacting with specific mitochondrial proteins.

To identify mitochondrial proteins that form a complex with mutant Htt, we used a biochemical approach and performed a pull-down experiment using a recombinant mutant Htt exon 1 (Httex1) N-terminal fragment fused to glutathione S-transferase (GST). We incubated purified mouse forebrain mitochondria with GST alone or GST fusion proteins containing Httex1 with a normal (GST-Httex1-23Q) or pathological (GST-Httex1-97Q) polyQ repeat, and subjected bound proteins to mass spectrometry (FIG. 1c). We identified 96 proteins that bound only to Httex1-97Q, but not to GST alone or GST-Httex1-23Q (FIG. 1c and Table 1). Among the Httex1-97Q-specific binding proteins, we found Tim50, Tim23 and Tim17a, all of which are subunits of the TIM23 complex in the inner membrane (FIG. 1c). Notably, although we detected several subunits of the TIM23 complex, we detected no subunits of the TIM22 carrier translocase complex, suggesting a specific interaction of mutant Htt with the TIM23 import pathway. All other proteins identified in the analysis are presented in Table 1.

We verified interaction of mutant Htt with components of the TIM23 complex by GST pull-down assays using isolated forebrain mitochondria (FIG. 1d). We found that the Tim23 subunit robustly bound to Httex1-97Q, with much weaker affinity for Httex1-23Q, but not to GST alone (FIG. 1d). An endogenous interaction between mutant Htt and TIM23 complex subunit Tim50 was detected in knock-in striatal cells expressing full-length mutant Htt and in R6/2 HD transgenic mouse brain, which expresses the mutant Httex1 N-terminal fragment (FIGS. 1e and 1f). Together, these results suggest that the N-terminal portion of mutant Htt can associate with mitochondria through a specific interaction with the import complex.

It has been suggested that the first N-terminal 17 amino acids (N17) of Htt are key to its subcellular localization (17). We therefore performed GST pull-down assays using purified GST-Httex1-97Q, GST-Httex1-97Q-ΔN17, which lacks the N17 sequence, and GST-N17 with mitochondria isolated from ST14A striatal cells and mouse brain. Both GST-Httex1-97Q-ΔN17 and GST-N17 showed little, if any, interaction with Tim17a, Tim23 and Tim50 (FIGS. 1g and 1h and data not shown), suggesting that N17 is required but not sufficient for interaction with the TIM23 complex. These results suggest that both N17 and the polyQ domains of mutant Htt are critical for the interaction with the TIM23 import machinery. Moreover, compared to Tim23 and Tim50, Tim17a was most enriched by GST-Httex1-97Q pulldown, suggesting that Httex1-97Q may interact primarily with Tim17a within the TIM23 complex. Collectively, these findings suggest that mutant Htt associates with mitochondria through a specific and direct interaction with the TIM23 complex and raise the hypothesis that mutant Htt may interfere with the import machinery.

Mutant Htt Inhibits Brain Mitochondrial Protein Import.

Given the physical association of mutant Htt with a mitochondrial translocase (FIGS. 1c-1g), we reasoned that mutant Htt may act directly on mitochondria to inhibit protein import and took advantage of an established in vitro protein import assay with a radiolabeled precursor matrix protein, pre-ornithine transcarbamylase (pOTC), to examine import activity in normal mitochondria in the presence of recombinant GST-Htt fusion proteins in vitro. pOTC is translocated across the outer and inner mitochondrial membranes via the TOM and TIM23 complexes, respectively, and is destined for the matrix, where the N-terminal presequence in pOTC is cleaved by a mitochondrial processing peptidase, producing mature OTC (mOTC). We incubated isolated mitochondria with $^{35}$S-labeled pOTC and detected imported mOTC in the matrix by fluorography after SDS-PAGE. This assay reflects the import activity for many nuclearly encoded mitochondrial proteins, including presequence-containing matrix, inner membrane and intermembrane space proteins that also utilize the TOM and TIM23 complexes (12).

We first incubated isolated mouse forebrain mitochondria with GST, GST-Httex1-23Q or GST-Httex1-97Q recombinant proteins (FIG. 2a) and then subjected them to the in vitro mitochondrial pOTC import assay (FIGS. 2b and 2c). GST-Httex1-97Q proteins inhibited pOTC import in mitochondria as compared to GST alone or GST-Httex1-23Q (FIGS. 2b and 2c). Incubation of wild-type (WT) mitochondria with 3 µM and 10 µM GST-Httex1-97Q reduced pOTC import by 50% and 73%, respectively, compared to that of control GST (FIG. 2b), indicating that the mutant Htt N-terminal fragment directly inhibits mitochondrial protein import in vitro. Incubation of mitochondria with GST-Httex1-23Q also led to a modest inhibitory effect on pOTC import as compared to incubation with GST (FIGS. 2b and 2c), raising the possibility that normal Htt may regulate protein import in mitochondria. However, two lines of evidence suggest this is not the case in cells. First, we observed no difference in mitochondrial protein import activity in Htt-null embryonic stem cells as compared to WT embryonic stem cells or in Htt knockdown ST14A cells as compared to vector-transfected cells (FIG. 7 and data not shown). Second, N-terminal WT Httex1-25Q does not to localize to mitochondria in transfected neurons, whereas mutant Httex1-97Q does11, suggesting that, in cells, WT Htt is not poised to affect mitochondrial protein import. Together, our results suggest that mutant Htt directly inhibits mitochondrial protein import via interaction with the import machinery.

Mutant Htt Impairs Mitochondrial Protein Import in Cells.

Next we examined whether mutant Htt inhibits import in cells. The mutant Htt knock-in striatal cell line ST-Hdh$^{Q111/Q111}$, which expresses full-length mutant Htt protein, demonstrated decreased pOTC import as compared to control knock-in striatal line ST-Hdh$^{Q7/Q7}$, which expresses full-length WT Htt (FIG. 3a, left). We observed a similar deficit in import activity using mitochondria isolated from rat striatal ST14A cells that stably express the N-terminal 548-amino-acid fragment of mutant Htt with a 120Q repeat (N548mut) compared with that of cells expressing the N-terminal Htt fragment with a 15Q repeat (N548 wt) (FIG. 3a, right). Finally, ST14A cells transiently transfected with plasmids encoding the N-terminal 170 amino acids of Htt with a pathological-length polyQ stretch (150Q) showed decreased import activity as compared with that of cells expressing Htt with a normal polyQ stretch (21Q) (FIG. 8). In addition to pOTC import assays, we measured mitochondrial protein import in living cells expressing mtGFP, which contains a presequence from a different mitochondrial matrix protein, pyruvate dehydrogenase (FIGS. 9a-9c), determining the rate of mtGFP accumulation in mitochondria by live time-lapse fluorescence imaging. The rate was significantly lower in ST-Hdh$^{Q111/Q111}$ than in ST-Hdh$^{Q7/Q7}$ cells (FIG. 9c), supporting our findings obtained with the radiolabeled pOTC import assay using isolated mitochondria. Thus, two different assay systems using distinct mitochondrial presequences demonstrated that mutant Htt decreases mitochondrial protein import (FIG. 3a and FIG. 9c).

Impaired Protein Import in HD Synaptosomal Mitochondria.

Next we determined whether the mitochondrial protein import deficiency occurs in vivo in mutant Htt-expressing transgenic mouse brain. For these experiments, we used two lines of R6/2 mice, carrying 150 (±5) and 195 (±10) CAG repeats, respectively. The 150CAG R6/2 is the original R6/2 line (18), whereas 195CAG R6/2 was spontaneously derived from the 150CAG R6/2 colony as a result of CAG repeat instability. Although the 195CAG R6/2 mice have a longer CAG repeat length, these mice die at 16-18 weeks of age, surviving approximately 3 weeks longer than 150CAG R6/2 mice. The investigation of two distinct R6/2 lines with differing CAG repeat lengths and disease severity may be informative, as it may reflect the heterogeneity of the human HD population.

Figure 3D:
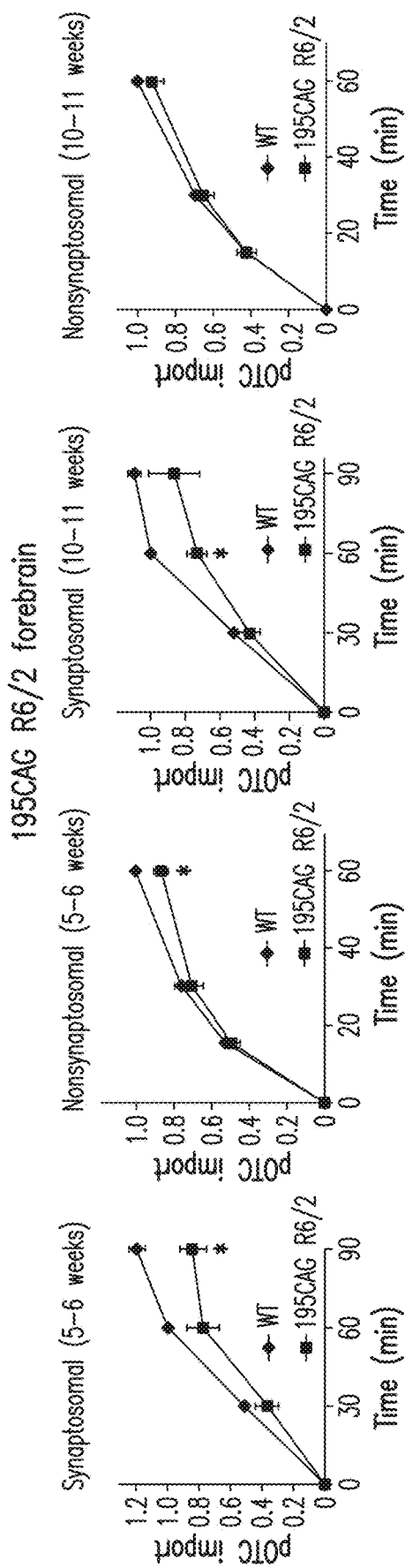

To evaluate protein import activity in brain mitochondria, we used highly purified synaptosomal mitochondria from neuronal synapses and nonsynaptosomal mitochondria from all cell populations in the brain, including neuronal and non-neuronal cells (FIG. 3b). Because of the energetic demands of synaptic transmission, we hypothesized that synaptosomal mitochondria might be preferentially vulnerable to disturbances in mitochondrial function. We subjected nonsynaptosomal and synaptosomal mitochondria isolated simultaneously from forebrains of presymptomatic 150CAG R6/2 and control WT mice at 22-24 d of age to the pOTC import assay (FIG. 3c). Nonsynaptosomal mitochondria from 150CAG R6/2 and WT mice did not exhibit a significant difference in protein import activity (FIG. 3c). In contrast, neuronal mitochondria purified from presymptomatic 150CAG R6/2 brain synaptosomes exhibited a 20-24% reduction in protein import as compared to that of mitochondria from WT brains (FIG. 3c), suggesting that synaptic neuronal mitochondria may be more vulnerable to mutant Htt toxicity than nonsynaptosomal mitochondria. Similarly, synaptosomal mitochondria from 195CAG R6/2 mice in presymptomatic mice (5-6 weeks old) and those with mid-stage disease (10-11 weeks old) showed decreased protein import compared to that of mitochondria from WT brains (FIG. 3d). Nonsynaptosomal mitochondria isolated from 195CAG R6/2 mice 5-6 weeks old showed only a modest reduction in protein import compared to WT brains (FIG. 3d). Both 150CAG and 195CAG R6/2 synaptosomal mitochondria demonstrated a protein import defect early in disease pathogenesis, suggesting that this defect might act as an early trigger for synaptic mitochondrial dysfunction and subsequent neurodegeneration.

Figure 3E:
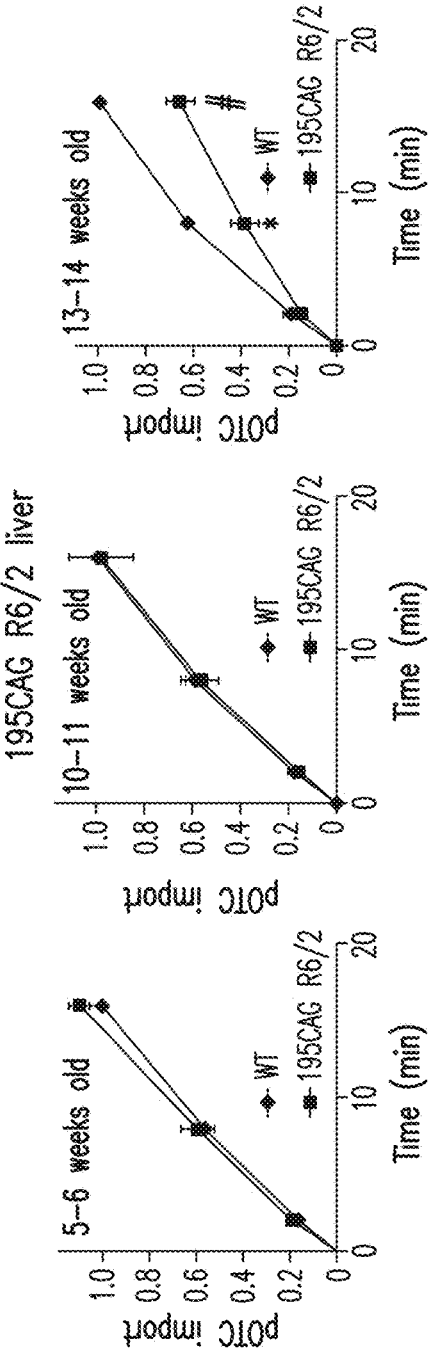

The clinical phenotype of HD is most selective to brain, and, in particular, to neurons. However, Htt is ubiquitously expressed in tissues outside of the CNS, including the liver. Expression of the N-terminal fragment of mutant human Htt exon 1 in R6/2 mice is driven by the human HTT promoter, and thus R6/2 liver expresses mutant Htt. We therefore determined whether liver mitochondria isolated from presymptomatic 195CAG R6/2 mice exhibit abnormalities in protein import. Unlike brain synaptosomal mitochondria, liver mitochondria demonstrated little or no deficit in protein import in the presymptomatic (5-6 weeks) or middle stage of the disease (10-11 weeks), but did demonstrate a protein import deficit at end-stage disease (13-14 weeks) (FIG. 3e). This tissue difference in mitochondrial protein import activity between brain and liver suggests that the mitochondrial import defect is an early cellular event specific to brain mitochondria in HD and, in particular, to neuronal mitochondria.

HD Import Defect Precedes Mitochondrial Respiratory Dysfunction.

The translocation of presequence proteins across the inner membrane to the matrix requires an intact mitochondrial membrane potential (12). Therefore, it is possible that the import deficit in R6/2 mice results from an impairment of the mitochondrial respiratory chain, which generates the mitochondrial membrane potential. To test this possibility, we assessed respiratory function in synaptosomal and nonsynaptosomal mitochondria isolated from forebrains of presymptomatic and mid-stage disease R6/2 mice at times when the import deficit in synaptosomal mitochondria is observed. We measured the resting (state 2) respiration rate with the addition of NAD-linked substrates, glutamate and malate, or FAD-linked substrate, succinate, using high-resolution respirometry and estimated the respiratory control ratio (FIGS. 10a-10b). Overall, the respiratory function of synaptosomal and nonsynaptosomal mitochondria from presymptomatic 150CAG R6/2 mice and presymptomatic and mid-stage disease 195CAG R6/2 mice was not different from that of WT littermates (FIGS. 10a-10b). Thus, in two distinct R6/2 lines with two different CAG repeat lengths, brain mitochondria with a protein import deficit demonstrated preserved mitochondrial bioenergetic integrity. These results suggest that the impairment in protein import is not due to altered mitochondrial respiratory function or membrane potential, in accord with previous studies showing decreased respiratory chain function only in advanced disease in mice and in human HD (19-21).

Impaired Protein Import in Mutant Htt-Expressing Neurons.

Because the protein import defect occurs in synaptosomal mitochondria from presymptomatic R6/2 mice before mitochondrial energetic failure, we hypothesized that import impairment may be an early, cell-intrinsic abnormality in neurons. To investigate mitochondrial protein import specifically in neurons before disease onset, we isolated mitochondria from primary cortical neurons prepared from embryonic day 15.5 (E15.5) 195CAG R6/2 and WT littermates and subjected them to the pOTC import assay (Supplementary FIG. 5a). Notably, we observed a modest but significant reduction in pOTC import in mitochondria isolated from R6/2 primary cortical neurons compared to those of WT littermates (FIG. 11a), suggesting a mild neuron-specific import defect in HD mice.

HD is an age-dependent progressive neurodegenerative disease, and therefore age-related insults, including oxidative stress, may contribute to the progressive nature of this disease. We hypothesized that mitochondrial protein import may be specifically vulnerable to reactive oxygen species-induced stress in HD neurons as compared to normal neurons. To test this hypothesis, we assessed protein import activity in mitochondria prepared from WT and 195CAG R6/2 neurons exposed to a sublethal dose of hydrogen peroxide (10 µM), which does not affect mitochondrial protein import or survival in WT neurons (FIG. 4a and FIGS. 11b-11c). Whereas sublethal hydrogen peroxide had little to no effect on import in WT neurons as compared to vehicle, hydrogen peroxide significantly decreased import in R6/2 neurons as compared to vehicle treatment (FIG. 4a), suggesting that mitochondrial protein import in R6/2 neurons is more vulnerable to sublethal oxidative stress, a phenomenon that may contribute to the age dependence observed in human HD.

We next took advantage of a primary cortical neuron model of HD to investigate the temporal relationships among mitochondrial protein import, mitochondrial metabolic activity and cell viability. In this system, lentivirally expressed mutant Httex1 (Httex1-72Q) but not WT Htt exon 1 (Httex1-25Q) accumulates as aggregates and decreases mitochondrial metabolic activity and cell viability (FIG. 4b and data not shown). We detected impaired protein import in mitochondria isolated from mutant Httex1-72Q-expressing neurons as compared to those expressing WT Httex1-25Q at a time before neurons begin to lose mitochondrial metabolic activity (FIG. 4c), suggesting that the mitochondrial protein import defect triggered by mutant Htt might cause cell death.

Because a pathological length of glutamine repeats is required for mutant Htt-induced impairment of protein import, we then asked whether mitochondrial import defect might be a common mechanism among various polyQ diseases. To address this question, we examined whether another polyQ disease protein, the mutant androgen receptor (AR), which is the causal protein in spinal and bulbar muscular atrophy (SBMA), would alter mitochondrial protein import in neurons by the pOTC import assay. Primary cortical neurons infected with mutant AR-expressing lentivirus (the N-terminal 127-amino-acid fragment of AR containing 65Q; AR-65Q) did not exhibit a decrease in mitochondrial protein import as compared to control- or WT AR-22Q-infected neurons, whereas primary neurons expressing Httex1-72Q, but not Httex1-25Q, demonstrated diminished mitochondrial protein import (FIG. 12a and data not shown), suggesting that inhibition of protein import is not a mechanism common to all polyQ diseases. In other experiments, expression of AR-65Q or Httex1-72Q, but not their WT counterparts, decreased mitochondrial metabolic activity in primary neurons (FIG. 12b), suggesting that AR-65Q decreases neuronal viability by a mechanism independent of mitochondrial import.

Inhibition of Protein Import Triggers Neuronal Death.

Figure 5A:
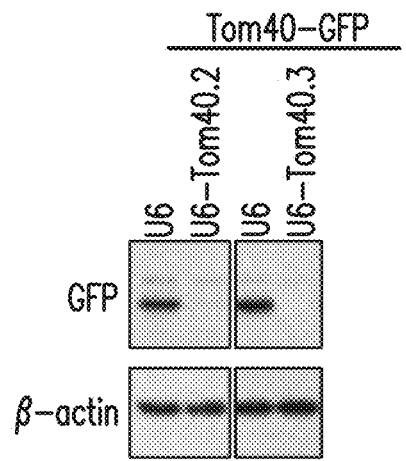
Figure 5B:
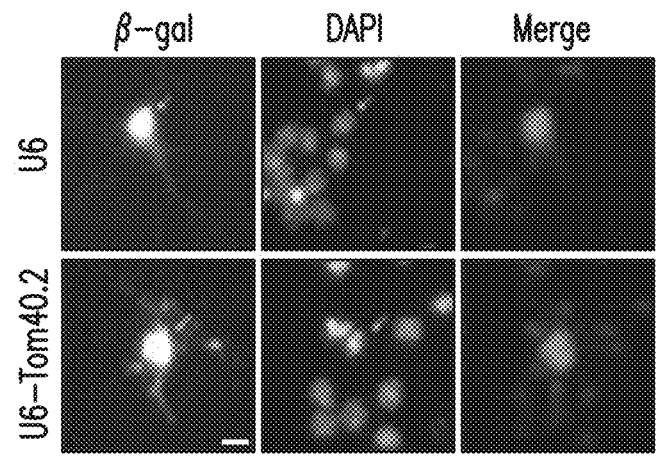
Figure 5C:
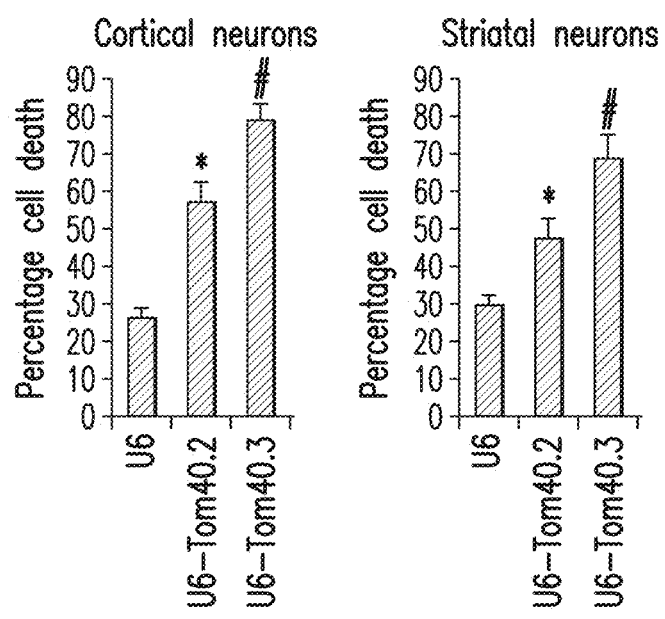

Given that protein import was perturbed in HD synaptosomal mitochondria early in the disease progression of R6/2 mice, before mitochondrial bioenergetic failure (FIGS. 3c-3d and FIGS. 10a-10b), in R6/2 primary cortical neurons (FIG. 4a and FIG. 11a) and in mutant Htt lentivirus-infected primary cortical neurons before cell death (FIGS. 4b-4c), we hypothesized that impaired mitochondrial protein import might contribute to disease pathogenesis. To understand the biological consequences of deficient mitochondrial protein import in neurons, we first knocked down the Tom40 subunit, a core component of the TOM complex essential for import of almost all nuclearly encoded mitochondrial proteins, in primary neurons. Transfection of short hairpin RNA plasmids targeting two distinct regions of Tomm40, encoding Tom40, efficiently reduced the levels of exogenous and endogenous Tom40 in cell lines and primary neurons (FIG. 5a and FIGS. 13a-13b). Mitochondria isolated from Tom40 knockdown cells demonstrated a decrease in protein import by 40% relative to that of control U6-transfected cells (FIG. 13c). Using these Tom40 shRNA plasmids, we then evaluated whether protein import was required for neuronal survival (FIGS. 5b-5c). Tom40 knockdown in primary cortical and striatal neurons triggered cell death as compared to vector transfection, suggesting mitochondrial protein import is essential for neuronal survival (FIGS. 5b-5c).

Caspase activation has been demonstrated to function in cellular and in vivo models of HD (22,23). We characterized Tom40 RNA interference-induced cell death in primary neurons by assessing the activation of caspase-3, an effector molecule of apoptotic signaling. Tom40 knockdown neurons demonstrated increased caspase-3 activation compared to that in vector-transfected neurons (FIG. 5d), and inhibition of caspase activation by a broad-spectrum caspase inhibitor, qVD-OPh, partially but significantly inhibited Tom40 RNAi-induced neuronal death (FIG. 5e). These results suggest that inhibition of mitochondrial protein import in neurons robustly activates caspase-dependent apoptotic signaling but that neuronal death occurs via caspase-dependent and caspase-independent pathways.

Figure 5G:
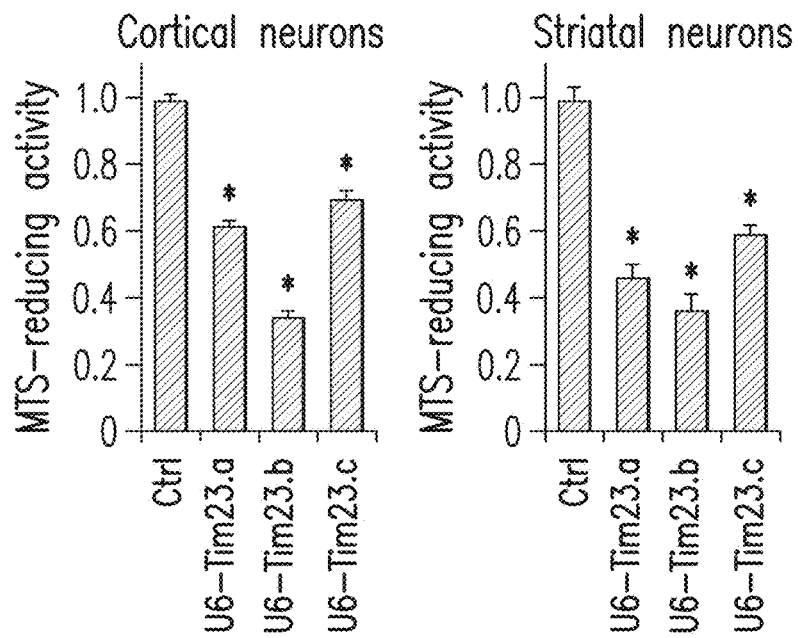
Figure 5H:
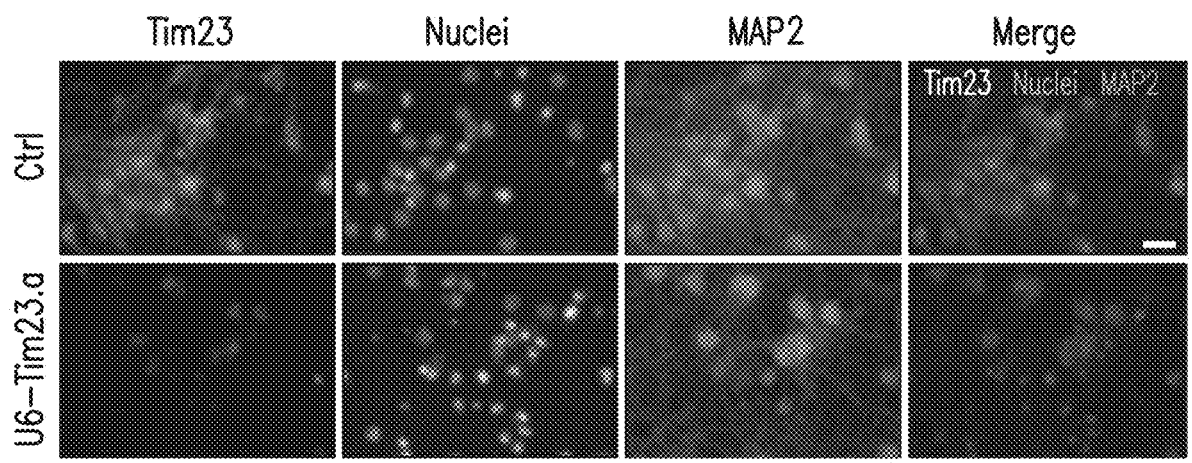

Given that the vast majority of nuclearly encoded mitochondrial proteins require the TOM import machinery for mitochondrial entry, our results indicate that global inhibition of mitochondrial protein import leads to neuronal death. Unlike the TOM complex, the TIM23 complex is responsible for the entry of a subset of, but not all, nuclearly encoded mitochondrial proteins. Our finding that mutant Htt binds to the TIM23 complex (FIGS. 1c-1g) raises the question of whether inhibition of TIM23-dependent import activity alone can also lead to mitochondrial dysfunction and neuronal death in neurons. Lentivirus-mediated delivery of shRNAs targeting three distinct regions of core TIM23 complex subunit mRNA Timm23, encoding Tim23, efficiently reduced the levels of endogenous Tim23 protein in primary neurons (FIG. 5f). Using these Tim23 shRNA lentiviruses, we evaluated whether Tim23 is required for mitochondrial function and cell survival in neurons. We subjected primary cortical and striatal neurons transduced with Tim23 RNAi lentiviruses to the MTS assay to determine mitochondrial metabolic activity. Knockdown of Tim23 decreased MTS-reducing activity in neurons compared to that in control-infected neurons, suggesting that Tim23 is essential for mitochondrial metabolic activity (FIG. 5g). In addition, knockdown of Tim23 in primary cortical and striatal neurons triggered cell death compared to control infection (FIGS. 5h and 5i), suggesting that the TIM23 import complex is critical for neuronal survival.

Figure 5K:
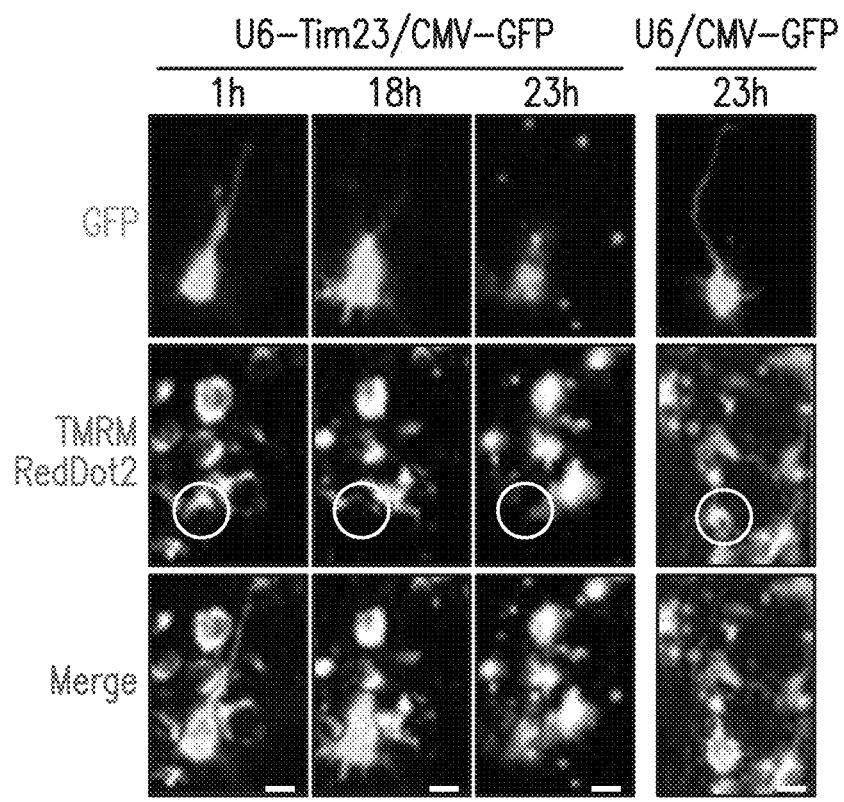
Figure 5L:
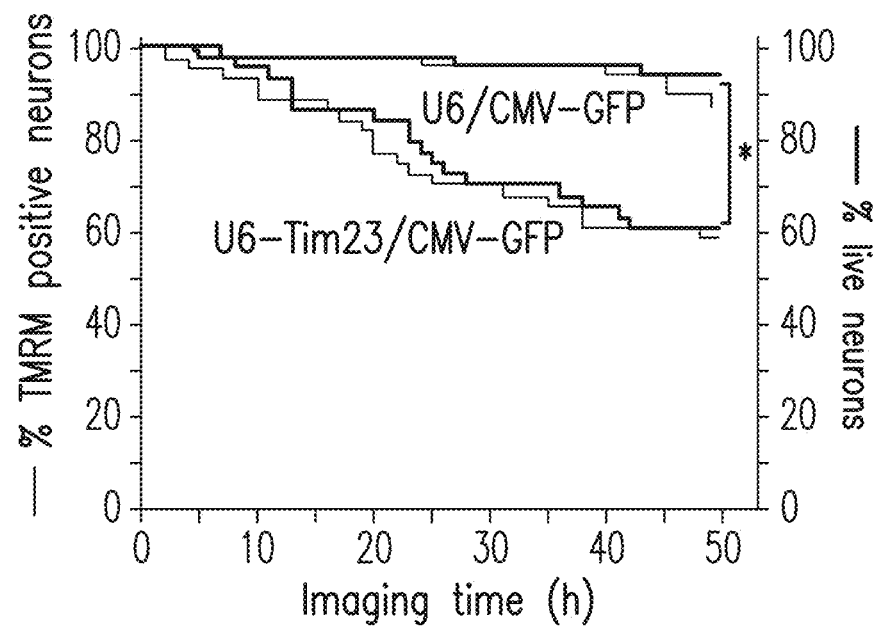

To delineate the temporal relationship between mitochondrial dysfunction and death caused by Tim23 knockdown, we took advantage of live time-lapse imaging to examine the functional effects of Tim23 knockdown in primary neurons. Transfection of the Tim23 shRNA plasmid reduced the levels of endogenous Tim23 protein in cells (FIG. 5j). Following transfection, we assessed the loss of mitochondrial membrane potential and cell death by live confocal imaging in neurons using, respectively, TMRM, a fluorescent dye that accumulates only in polarized mitochondria, and RedDot2, a nuclear dye with high selectivity for membrane-compromised dead cells (FIGS. 5k, 5l). Tim23 knockdown decreased the percentage of TMRM-positive neurons compared to that in control-transfected neurons, suggesting that defective TIM23-dependent protein import leads to loss of mitochondrial membrane potential (FIG. 5l). Notably, we found that Tim23 knockdown always induced loss of mitochondrial membrane potential before cell death (by 3.4±0.13 h) (FIGS. 5k, 5l). Together, our results indicate that impairment of both global and TIM23-driven mitochondrial protein import leads to neuronal death.

Deficient Protein Import Contributes to Neuronal Death by Mutant Htt.

The finding that protein import was impaired in mutant Htt-expressing primary neurons before decreased mitochondrial metabolic activity (FIGS. 4b, 4c) raises the hypothesis that impaired import may drive cell death. We therefore increased protein import in mutant Httex1-72Q-expressing neurons through enforced expression of the TIM23 complex by lentivirus-mediated expression of the three major subunits, Tim23, Tim50 and Tim17a (FIG. 6a). We confirmed the expression of these subunits by qRT-PCR and by immunoblotting (data not shown). Overexpression of the major subunits of the TIM23 complex in mutant Httex1-expressing primary neurons rescued the mitochondrial protein import defect and partially but significantly increased mitochondrial metabolic activity (FIG. 6b). Overexpression of individual subunits was not observed to rescue the protein import defect. Notably, overexpression of the TIM23 complex subunits inhibited mutant Htt-induced cell death (FIG. 6c). Taken together, these findings indicate that mutant Htt-induced inhibition of mitochondrial protein import can cause mitochondrial dysfunction and neuronal death. Collectively, we have provided a mechanism by which mutant Htt directly impairs mitochondrial protein import through an interaction with the import machinery and have demonstrated that this mitochondrial import defect triggers mutant Htt-induced cell death (FIG. 14).

6.1.3 Discussion

Direct association of N-terminal mutant Htt fragments with mitochondria has been found in transfected primary neurons and brain neurons from several HD transgenic mice (9-11). In this study, we have demonstrated that mutant Htt localizes to mitochondria in the caudate nucleus of patients with HD, suggesting a direct toxic effect of mutant Htt on mitochondria. Although a large body of evidence has implicated mitochondrial dysfunction as central to HD, the underlying molecular basis for mutant Htt-induced mitochondrial abnormalities had remained largely undefined. We have found that mutant Htt interacts with the mitochondrial TIM23 translocase complex and directly causes protein import deficiency. We also provide evidence that mutant Htt-induced protein import defect causes mitochondrial dysfunction and neuronal death in primary neurons. The machinery provides not only a specific molecular basis for the association of mutant Htt with mitochondria but also reveals an important biological process disrupted by mutant Htt, leading to mitochondrial dysfunction. Thus, our study highlights an important and early contribution of disruption of the mitochondrial protein import system to neuronal death in HD.

Several mitochondrial deficits, including decreased membrane potential and respiratory function, decreased calcium buffering capacity, and altered mitochondrial number and morphology, have been associated with HD (3, 11, 16, 24-27). The defect in protein import is an early, specific event observed in R6/2 forebrain neuronal mitochondria, as we found no alterations in respiratory function using the respiratory complex I and II substrates at a time when import deficits are observed. These results suggest that protein import deficiency is not a consequence of a reduction in mitochondrial membrane potential and likely drives further mitochondrial insults by decreasing the levels of key imported proteins involved in essential mitochondrial functions. Reduced import of proteins involved in the tricarboxylic acid cycle, oxidative phosphorylation, defense mechanisms against reactive oxygen species, and mitochondrial DNA repair may result in lower mitochondrial ATP production and increased oxidative damage of mitochondrial proteins and DNA, which are observed in HD (9,28-31). Previous studies using isolated mitochondria showed that the N-terminal fragment of mutant Htt or expanded polyQ domain alone directly decreases the calcium threshold for the mitochondrial permeability transition pore, calcium retention capacity and mitochondrial membrane potential (16,17,24). The relationship between these mitochondrial deficits and protein import will be a worthwhile focus for future studies.

Mitochondrial morphology is regulated by a dynamic balance between fusion and fission. Recent studies have suggested that mutant Htt affects mitochondrial dynamics via its abnormal interaction with and activation of the mitochondrial fission GTPase DRP1 to increase mitochondrial fragmentation (11,27,32). Notably, a previous yeast mutant screen demonstrated that yeast lacking subunits of the TOM, the sorting and assembly machinery (SAM) or the TIM23 complexes show severe defects in mitochondrial morphology, suggesting that mitochondrial protein import, assembly and sorting are required for mitochondrial morphogenesis (33,34). Thus, it is conceivable that the early defect in mitochondrial protein import in neurons of presymptomatic HD-affected brain might lead to aberrant mitochondrial morphology by affecting the levels of proteins related to mitochondrial morphogenesis.

A fundamental question in HD is why the brain and, in particular, neurons are selectively affected, even though mutant Htt is expressed throughout the body. The early impairment in mitochondrial protein import observed in forebrain synaptosomal mitochondria of R6/2 mice but not liver mitochondria in vivo suggests that the mitochondrial protein import defect occurs in a tissue-, cell type- and time-dependent manner. To our knowledge, this is the first time a mitochondrial protein import defect has been observed in synaptosomal mitochondria in any neurological disease. It is noteworthy that, in HD knock-in mouse brain, ATP levels are reduced in the synaptosomal fraction, but not in the cytoplasmic fraction, late in disease (9). Together, these findings suggest the decreased levels of ATP and degenerated mitochondria in synaptic sites in HD may result from an early impairment in mitochondrial protein import. Given that presynaptic mitochondria are important for synaptic vesicle release and recycling, it is possible that the early protein import deficit in synaptic mitochondria in HD model mice may result in altered synaptic transmission, leading potentially to the neuronal dysfunction observed in patients with HD35.

Mitochondrial protein import in primary R6/2 cortical neurons was particularly sensitive to sublethal hydrogen peroxide compared to that in WT neurons. Oxidative stress may thus amplify a neuronal vulnerability in mitochondrial protein import over time and contribute to the progressive deficits seen in patients with HD. Because antioxidants have been shown to be effective in slowing disease progression in HD transgenic mice36, our results raise the possibility that the therapeutic effect of antioxidants may be mediated, at least in part, by modifying mitochondrial protein import.

The mechanism of mutant Htt action on mitochondrial protein import and the downstream mitochondrial pathophysiology has implications for diverse neurological disorders. Mitochondrial protein import has been implicated in other neurodegenerative diseases, including Alzheimer's disease and amyotrophic lateral sclerosis (37-39). Interestingly, genetic mutation of an import-associated gene has been shown to lead to the X-linked recessive disorder Mohr-Tranebjaerg syndrome (also known as deafness dystonia syndrome), a progressive neurodegenerative disease caused by mutations in the deafness-dystonia protein-1 (DDP1) gene, Tim8a (ref 40). A link between an import defect and neurological disease has also been demonstrated in heterozygous Timm23 knockout mice, which exhibit a neurological phenotype, although the exact molecular and cellular nature of the abnormality remains to be elucidated (41). Our finding that a mitochondrial import deficit directly causes neurodegeneration raises the possibility that other neurodegenerative diseases exhibiting import defects might use common cell death mechanisms. Impairment of mitochondrial protein import in neurons triggered cell death by caspase-dependent and caspase-independent mechanisms, consistent with reported mechanisms of mutant Htt-induced cell death observed in striatal cell lines and in mice in vivo (22,23). Recent studies have identified proteins that monitor mitochondrial homeostasis through the protein import machinery (42), raising the possibility that such molecular sensors may activate specific death pathways in response to a global decrease in protein import. The identification of specific matrix proteins whose levels are decreased in mitochondria in HD neurons may also provide insights into the detailed mechanism of how protein import inhibition might lead to neuronal death.

In addition to HD, there are eight polyQ diseases, including SBMA, dentatorubral-pallidoluysian atrophy and spinocerebellar ataxia type 1, that are caused by the expansion of a polyQ tract in specific proteins and are also progressive neurodegenerative disorders with the loss of selective neurons (43,44), raising the possibility that other polyQ diseases may trigger protein import defects. Our experiments, however, indicate that the causal protein in SBMA, mutant AR, which harbors an expanded glutamine repeat, has little to no effect on mitochondrial protein import, suggesting that import deficits are not common to all polyQ disorders, consistent with the requirement for both the N17 N-terminal sequence and the polyQ of mutant Httex1 for interaction with the TIM23 complex. It will be of great future interest to examine whether other polyQ disease proteins might carry an N17-like sequence and therefore potentially affect mitochondrial protein import.

In addition to a direct effect of mutant Htt on mitochondrial function, many lines of evidence have suggested that transcriptional dysregulation is important to the mechanism of mitochondrial dysfunction. PGC-1α, a key transcriptional coactivator that regulates the expression of genes involved in energy metabolism and mitochondrial biogenesis, has been shown to be downregulated in HD (25,45,46). As such, therapeutic strategies targeting both the direct action of mutant Htt on mitochondria and the transcriptional deregulation of mitochondrial proteins may thus be necessary to effectively rescue mitochondrial dysfunction in HD.

TABLE 1

Proteins pulled down with GST-Httex1-97Q, but not GST or GST-Httex1-23Q (96 proteins)

| Protein | No. of unique peptides | No. of total peptides |
| --- | --- | --- |
| Ppp3r1_IPI:IPI00474116.3 | 7 | 7 |
| Dci_IPI:IPI00114416.1 | 6 | 7 |
| Cplx1_IPI:IPI00132278.1 | 4 | 6 |
| Brp44_IPI:IPI00131896.1 | 5 | 5 |
| Echs1_IPI:IPI00454049.4 | 5 | 5 |
| Afg3l2_IPI:IPI00170357.5 | 4 | 5 |
| Dsp_IPI:IPI00553419.3 | 4 | 4 |
| Letm1_IPI:IPI00131177.1 | 4 | 4 |
| Mpst_IPI:IPI00604945.2 | 4 | 4 |
| Ppdpf_IPI:IPI00133078.1 | 4 | 4 |
| Etfa_IPI:IPI00116753.4 | 3 | 4 |
| Mrpl14_IPI:IPI00133778.1 | 3 | 4 |
| Arf2_IPI:IPI00135730.1 | 3 | 3 |
| Asah1_IPI:IPI00125266.1 | 3 | 3 |
| Gnao1_IPI:IPI00115546.4 | 3 | 3 |
| Isca2_IPI:IPI00120671.2 | 3 | 3 |
| LOC100044454_IPI:IPI00135284.1 | 3 | 3 |
| Mtch1_IPI:IPI00137173.1 | 3 | 3 |
| Mtx1_IPI:IPI00112327.1 | 3 | 3 |
| Ociad2_IPI:IPI00112139.1 | 3 | 3 |
| Prdx3_IPI:IPI00116192.1 | 3 | 3 |
| Rab14_IPI:IPI00126042.3 | 3 | 3 |
| Timm50_IPI:IPI00111045.1 | 3 | 3 |
| Cisd1_IPI:IPI00128346.1 | 2 | 3 |
| Acadsb_IPI:IPI00119842.1 | 2 | 2 |
| Acp6_IPI:IPI00624175.1 | 2 | 2 |
| Chchd3_IPI:IPI00133562.1 | 2 | 2 |
| Coq5_IPI:IPI00379695.2 | 2 | 2 |
| Fis1_IPI:IPI00132217.1 | 2 | 2 |
| Gm561_IPI:IPI00344567.1 | 2 | 2 |
| Hagh_IPI:IPI00115866.2 | 2 | 2 |
| Hsdl1_IPI:IPI00225301.1 | 2 | 2 |
| Idh3g_IPI:IPI00109169.1 | 2 | 2 |
| Iscu_IPI:IPI00110578.1 | 2 | 2 |
| Mthfd1l_IPI:IPI00228113.5 | 2 | 2 |
| Sfxn1_IPI:IPI00115454.3 | 2 | 2 |
| Slc25a27_IPI:IPI00108998.1 | 2 | 2 |
| Suclg2_IPI:IPI00459487.3 | 2 | 2 |
| Coq3_IPI:IPI00467124.2 | 1 | 2 |
| 1700020C11Rik_IPI:IPI00315908.1 | 1 | 1 |
| 2900010M23Rik_IPI:IPI00133350.1 | 1 | 1 |
| 5730469M10Rik_IPI:IPI00187272.3 | 1 | 1 |
| Acad8_IPI:IPI00274222.2 | 1 | 1 |
| Actg1_IPI:IPI00136929.1 | 1 | 1 |
| Agk_IPI:IPI00113606.2 | 1 | 1 |
| Asrgl1_IPI:IPI00223875.1 | 1 | 1 |
| Atp1a1_IPI:IPI00311682.5 | 1 | 1 |
| Chchd4_IPI:IPI00124389.1 | 1 | 1 |
| Cisd3_IPI:IPI00345740.4 | 1 | 1 |
| Cyc1_IPI:IPI00132728.2 | 1 | 1 |
| Dnaja3_IPI:IPI00120414.1 | 1 | 1 |
| Dnajc19_IPI:IPI00111111.5 | 1 | 1 |
| Dsg1c_IPI:IPI00331259.3 | 1 | 1 |
| Fabp5_IPI:IPI00114162.3 | 1 | 1 |
| Fahd1_IPI:IPI00468850.1 | 1 | 1 |

TABLE 1-continued

| Protein | | |
|---|---|---|
| Gm6180__IPI:IPI00409405.2 | 1 | 1 |
| Gnb3__IPI:IPI00116938.1 | 1 | 1 |
| Gstk1__IPI:IPI00121051.3 | 1 | 1 |
| Hint2__IPI:IPI00133034.3 | 1 | 1 |
| Hmgcl__IPI:IPI00379694.4 | 1 | 1 |
| Hsd17b10__IPI:IPI00320847.1 | 1 | 1 |
| Hspa5__IPI:IPI00319992.1 | 1 | 1 |
| Lyrm4__IPI:IPI00169804.1 | 1 | 1 |
| Lyrm7__IPI:IPI00117832.1 | 1 | 1 |
| Mrpl43__IPI:IPI00278781.1 | 1 | 1 |
| Mrps33__IPI:IPI00135214.1 | 1 | 1 |
| Ndufa11__IPI:IPI00318645.6 | 1 | 1 |
| Nsf__IPI:IPI00656325.2 | 1 | 1 |
| Nubpl__IPI:IPI00317709.1 | 1 | 1 |
| Nup210l__IPI:IPI00356451.5 | 1 | 1 |
| Oxa1l__IPI:IPI00308001.1 | 1 | 1 |
| Pnkd__IPI:IPI00187405.4 | 1 | 1 |
| Ppt1__IPI:IPI00331318.2 | 1 | 1 |
| Pptc7__IPI:IPI00421081.3 | 1 | 1 |
| Pycr2__IPI:IPI00123278.1 | 1 | 1 |
| Rab15__IPI:IPI00170032.1 | 1 | 1 |
| Rab2a__IPI:IPI00137227.1 | 1 | 1 |
| Rab5b__IPI:IPI00116563.2 | 1 | 1 |
| Rdh13__IPI:IPI00229040.1 | 1 | 1 |
| Rdh14__IPI:IPI00112377.1 | 1 | 1 |
| Rhot1__IPI:IPI00123186.4 | 1 | 1 |
| Rtn1__IPI:IPI00395193.1 | 1 | 1 |
| Sccpdh__IPI:IPI00153266.1 | 1 | 1 |
| Slc25a10__IPI:IPI00317074.3 | 1 | 1 |
| Slc25a19__IPI:IPI00118826.1 | 1 | 1 |
| Slc6a11__IPI:IPI00136867.1 | 1 | 1 |
| Snap25__IPI:IPI00125635.1 | 1 | 1 |
| Stoml2__IPI:IPI00115117.1 | 1 | 1 |
| Synj2bp__IPI:IPI00109206.1 | 1 | 1 |
| Timm17a__IPI:IPI00129506.1 | 1 | 1 |
| Timm23__IPI:IPI00123712.1 | 1 | 1 |
| Tpi1__IPI:IPI00467833.6 | 1 | 1 |
| Uqcrb__IPI:IPI00132347.1 | 1 | 1 |
| Uqcrq__IPI:IPI00224210.5 | 1 | 1 |
| Ywhaq__IPI:IPI00408378.4 | 1 | 1 |
| Ywhaz__IPI:IPI00116498.1 | 1 | 1 |

Proteins pulled down with GST-Httex1-97Q and GST-Httex1-23Q, but not GST (24 proteins)

| | GST-Httex1-23Q | | GST-Httex1-97Q | |
|---|---|---|---|---|
| Protein | No. of unique peptides | No. of total peptides | No. of unique peptides | No. of total peptides |
| Sfxn5__IPI:IPI00221602.1 | 3 | 3 | 5 | 6 |
| Cplx2__IPI:IPI00111501.1 | 1 | 1 | 5 | 6 |
| Ccdc127__IPI:IPI00131843.3 | 2 | 2 | 5 | 5 |
| Cend1__IPI:IPI00122826.1 | 3 | 3 | 4 | 5 |
| Gbas__IPI:IPI00115827.1 | 2 | 2 | 3 | 5 |
| Atp5f1__IPI:IPI00341282.2 | 3 | 3 | 4 | 4 |
| mt-Co2__IPI:IPI00131176.1 | 1 | 1 | 3 | 4 |
| Atp1a3__IPI:IPI00122048.2 | 2 | 2 | 3 | 3 |
| C1qbp__IPI:IPI00132799.4 | 3 | 6 | 2 | 3 |
| Tuba4a__IPI:IPI00117350.1 | 3 | 3 | 2 | 2 |
| Acsl6__IPI:IPI00123390.8 | 2 | 2 | 2 | 2 |
| IPI:IPI00123176.1__IPI:IPI00123176.1 | 1 | 1 | 2 | 2 |
| Pfn2__IPI:IPI00227805.6 | 1 | 1 | 2 | 2 |
| Slc25a1__IPI:IPI00276926.3 | 1 | 1 | 2 | 2 |
| Syngr3__IPI:IPI00331579.1 | 1 | 1 | 2 | 2 |
| Vsnl1__IPI:IPI00230418.5 | 1 | 1 | 2 | 2 |
| Timm17b__IPI:IPI00129504.1 | 3 | 3 | 1 | 1 |
| Hmgcl__IPI:IPI00127625.1 | 1 | 1 | 1 | 1 |
| Hspa9__IPI:IPI00880839.1 | 1 | 1 | 1 | 1 |
| Loh12cr1__IPI:IPI00457620.2 | 1 | 1 | 1 | 1 |
| Ndufb5__IPI:IPI00132531.1 | 1 | 1 | 1 | 1 |
| Nipsnap1__IPI:IPI00115824.1 | 1 | 1 | 1 | 1 |
| Slc1a2__IPI:IPI00230289.1 | 1 | 1 | 1 | 1 |
| Tomm20__IPI:IPI00120715.1 | 1 | 1 | 1 | 1 |

6.2 Example 2: Serine S13 and S16 Phosphomimetic Mutations of Mutant 97Q Htt Reduce Tim23 Binding to 97Q Htt 6.2.1 Materials and Methods Mutagenesis of Serine at Positions 13 and 16 of Huntingtin Fusion Protein.

Phosphomimetic glutamic acid mutations were introduced at amino acids S13 and S16 of the GST-Httex1-97Q and GST-Httex1-23Q fusion proteins. S13E and S16E mutations were introduced through use of the GeneArt mutagenesis kit (Invitrogen) and the following primer sets: 5'-CTG ATG AAG GCC TTC GAG GAA CTC AAG GAA TTC CAG CAG CA-3' (SEQ ID NO:12) and 5'-CTG CTG CTG GAA TTC CTT GAG TTC CTC GAA GGC CTT CAT CA-3' (SEQ ID NO:13).

Preparation of Fusion Proteins from Bacteria.

GST and GST-Htt exon 1 (GST-Httex1) fusion proteins (97Q, 23Q, 97Q S13E S16E, 23Q S13E S16E, 97Q S13A S16A, 23Q S13A S16A) were purified from transformed BL21star (DE3) cells (Life Technologies) (55). GST fusion proteins bound to glutathione 4B Sepharose beads (GE Healthcare) were eluted with 50 mM Tris buffer (pH 8) containing 10 mM reduced glutathione. The purified proteins in the glutathione elution buffer were then concentrated in PBS using AmiconUltra-10K centrifugal filters (Millipore).

Mouse Timm23, Timm50, Timm17A, and Timm17B cDNA were subcloned into the GST-Httex1 vector and transformed into BL21star (DE3) cells (Life Technologies). GST-Tim23, GST-Tim50, GST-Tim17A, and GST-Tim17B fusion proteins were purified from the cells by using glutathione 4B Sepharose beads (GE Healthcare) to bind the fusion proteins. To purify Tim proteins from GST, the GST fusion protein-bead complexes were digested with thrombin protease (GE Healthcare) at 25° C. overnight, and eluted with PBS. The eluted proteins were concentrated in PBS using AmiconUltra-10K centrifugal filters (Millipore).

GST Pull Down Assay.

GST-Htt exon 1 proteins and GST removed Tim proteins were incubated with glutathione 4B Sepharose beads (GE Healthcare) at 4° C. overnight. The glutathione beads were then washed extensively with ice-cold PBS, and bound proteins were subjected to SDS-PAGE followed by immunoblotting analysis.

Surface Plasmon Resonance (SPR) Biacore™ Analysis.

Experiments were performed using a Biacore™ 1000 instrument (GE Healthcare) and HBS-EP running buffer, pH 7.4, containing 10 mM HEPES, 150 mM NaCl, 3 mM EDTA, and 0.005% surfactant P20. Anti-GST antibody was diluted (30 µg/ml) and coupled to Series S CMS sensor chips by an amine-coupling procedure, as recommended by the manufacture, with a mixture containing EDC (N-ethyl-N'-(dimethylaminopropyl) carbodiide and NHS (N-hydroxysuccinimide).

Typically, between 100 and 150 resonance units (RU) of GST antibody were immobilized. High affinity GST binding sites were blocked with GST proteins. A reference surface was prepared with activation and deactivation treatments, but with no protein coupled to an adjacent flow cell. For the experimental conditions, diluted GST fusion proteins (5 µg/ml) (GST-Httex1-97Q, GST-Httex1-23Q, GST-Httex1-97Q S13E S16E, and GST-Httex1-23Q S13E S16E), were injected for 2 min at a flow rate of 20 µl/min. Purified Tim23, Tim50, Tim17A and Tim17B were then injected onto the immobilized ligand surface at different concentrations to obtain SPR response curves (sensorgrams). Baseline-corrected sensorgrams (with the buffer blank run further subtracted) were globally fitted to a predefined binding model using BIAevaluation software (version 2.0.4). Between experiments, the surfaces were strictly regenerated with multiple pulses of 2M NaCl and 1.5 M glycine-HCl, pH 2.5, followed by an extensive wash procedure with running buffer.

6.2.2 Results

GST Pull Down Assay.

Tim23 bound to the GST-Httex1-97Q fusion protein, but showed minimal bind to GST-Httex1-23Q fusion protein (FIG. 16). Furthermore, deleting the N-terminal 17 amino acids from Htt (GST-Httex1-97Q ΔN17) prevented the 97Q fusion protein from binding to Tim23. Similarly, the N-terminal 17 amino acids alone (GST-N17) did not bind to Tim proteins (FIG. 16). Tim17A protein shows some binding to GST-Httex1-97Q protein in a similar pattern as Tim23. Tim50 binds more weakly to GST-Httex1-97Q, and Tim17B did not bind to any of the Htt fusion proteins. (FIG. 16).

Surface Plasmon Resonance (SPR) Biacore™ Analysis.

Tim23 binds with high affinity to GST-Httex1-97Q, but not with GST-Httex1-23Q (FIG. 17). Tim23 exhibited reduced affinity for phosphomimetic 97Q S13E S16E proteins (GST-Httex1-97Q S13E S16E) compared to the 97Q counterpart protein (GST-Httex1-97Q) (FIG. 17). However, unlike GST-Httex1-97Q proteins, Tim 23 showed increased affinity for phosphomimetic Htt exon1 23Q S13E S16E proteins (GST-Httex1-23Q S13E S16E) compared to the non-phosphomutated counterpart 23Q protein. Thus, while phosphorylation of S13 and S16 of Htt 97Q may decrease binding of Tim23 to the mutant Htt protein, phosphorylation of these serine residues in the non-mutant 23Q Htt protein may increase binding to Tim23.

7. REFERENCES

1. Hersch, S. M., Rosas, H. R. & Ferrante, R. J. Neuropathology and pathophysiology of Huntington's disease. in Movement Disorders 3rd edn. (eds. Watts, R. L., Standaert, D. G. & Obeso, J. A.) 683 (McGraw-Hill, New York, 2012).
2. The Huntington's Disease Collaborative Research Group. A novel gene containing a trinucleotide repeat that is expanded and unstable on Huntington's disease chromosomes. Cell 72, 971-983 (1993).
3. Damiano, M., Galvan, L., Deglon, N. & Brouillet, E. Mitochondria in Huntington's disease. Biochim. Biophys. Acta 1802, 52-61 (2010).
4. Costa, V. & Scorrano, L. Shaping the role of mitochondria in the pathogenesis of Huntington's disease. EMBO J. 31, 1853-1864 (2012).
5. Reddy, P. H. & Shirendeb, U. P. Mutant huntingtin, abnormal mitochondrial dynamics, defective axonal transport of mitochondria, and selective synaptic degeneration in Huntington's disease. Biochim. Biophys. Acta 1822, 101-110 (2012).
6. Bates, G. Huntingtin aggregation and toxicity in Huntington's disease. Lancet 361, 1642-1644 (2003).
7. Li, H., Li, S. H., Johnston, H., Shelbourne, P. F. & Li, X. J. Amino-terminal fragments of mutant huntingtin show selective accumulation in striatal neurons and synaptic toxicity. Nat. Genet. 25, 385-389 (2000).
8. DiFiglia, M. et al. Aggregation of huntingtin in neuronal intranuclear inclusions and dystrophic neurites in brain. Science 277, 1990-1993 (1997).
9. Orr, A. L. et al. N-terminal mutant huntingtin associates with mitochondria and impairs mitochondrial trafficking. J. Neurosci. 28, 2783-2792 (2008).
10. Yu, Z. X. et al. Mutant huntingtin causes context-dependent neurodegeneration in mice with Huntington's disease. J. Neurosci. 23, 2193-2202 (2003).
11. Song, W. et al. Mutant huntingtin binds the mitochondrial fission GTPase dynamin-related protein-1 and increases its enzymatic activity. Nat. Med. 17, 377-382 (2011).
12. Chacinska, A., Koehler, C. M., Milenkovic, D., Lithgow, T. & Pfanner, N. Importing mitochondrial proteins: machineries and mechanisms. Cell 138, 628-644 (2009).
13. Baker, M. J., Frazier, A. E., Gulbis, J. M. & Ryan, M. T. Mitochondrial protein-import machinery: correlating structure with function. Trends Cell Biol. 17, 456-464 (2007).
14. MacKenzie, J. A. & Payne, R. M. Mitochondrial protein import and human health and disease. Biochim. Biophys. Acta 1772, 509-523 (2007).
15. Li, H., Li, S. H., Yu, Z. X., Shelbourne, P. & Li, X. J. Huntingtin aggregate-associated axonal degeneration is an early pathological event in Huntington's disease mice. J. Neurosci. 21, 8473-8481 (2001).
16. Panov, A. V. et al. Early mitochondrial calcium defects in Huntington's disease are a direct effect of polyglutamines. Nat. Neurosci. 5, 731-736 (2002).
17. Rockabrand, E. et al. The first 17 amino acids of Huntingtin modulate its sub-cellular localization, aggregation and effects on calcium homeostasis. Hum. Mol. Genet. 16, 61-77 (2007).
18. Mangiarini, L. et al. Exon 1 of the HD gene with an expanded CAG repeat is sufficient to cause a progressive neurological phenotype in transgenic mice. Cell 87, 493-506 (1996).
19. Browne, S. E. et al. Oxidative damage and metabolic dysfunction in Huntington's disease: selective vulnerability of the basal ganglia. Ann. Neurol. 41, 646-653 (1997).
20. Gu, M. et al. Mitochondrial defect in Huntington's disease caudate nucleus. Ann. Neurol. 39, 385-389 (1996).
21. Browne, S. E. & Beal, M. F. The energetics of Huntington's disease. Neurochem. Res. 29, 531-546 (2004).
22. Ona, V. O. et al. Inhibition of caspase-1 slows disease progression in a mouse model of Huntington's disease. Nature 399, 263-267 (1999).
23. Wang, X. et al. Minocycline inhibits caspase-independent and -dependent mitochondrial cell death pathways in models of Huntington's disease. Proc. Natl. Acad. Sci. USA 100, 10483-10487 (2003).
24. Choo, Y. S., Johnson, G. V., MacDonald, M., Detloff, P. J. & Lesort, M. Mutant huntingtin directly increases susceptibility of mitochondria to the calcium-induced permeability transition and cytochrome c release. Hum. Mol. Genet. 13, 1407-1420 (2004).
25. Kim, J. et al. Mitochondrial loss, dysfunction and altered dynamics in Huntington's disease. Hum. Mol. Genet. 19, 3919-3935 (2010).
26. Reddy, P. H. et al. Abnormal mitochondrial dynamics and synaptic degeneration as early events in Alzheimer's disease: implications to mitochondria-targeted antioxidant therapeutics. Biochim. Biophys. Acta 1822, 639-649 (2012).
27. Costa, V. et al. Mitochondrial fission and cristae disruption increase the response of cell models of Huntington's disease to apoptotic stimuli. EMBO Mol. Med. 2, 490-503 (2010).

28. Gines, S. et al. Specific progressive cAMP reduction implicates energy deficit in presymptomatic Huntington's disease knock-in mice. Hum. Mol. Genet. 12, 497-508 (2003).

29. Mochel, F. et al. Early alterations of brain cellular energy homeostasis in Huntington disease models. J. Biol. Chem. 287, 1361-1370 (2012).

30. Mochel, F. & Haller, R. G. Energy deficit in Huntington disease: why it matters. J. Clin. Invest. 121, 493-499 (2011).

31. Acevedo-Torres, K. et al. Mitochondrial DNA damage is a hallmark of chemically induced and the R6/2 transgenic model of Huntington's disease. DNA Repair (Amst.) 8, 126-136 (2009).

32. Shirendeb, U. P. et al. Mutant huntingtin's interaction with mitochondrial protein Drp1 impairs mitochondrial biogenesis and causes defective axonal transport and synaptic degeneration in Huntington's disease. Hum. Mol. Genet. 21, 406-420 (2012).

33. Meisinger, C. et al. The mitochondrial morphology protein Mdm10 functions in assembly of the preprotein translocase of the outer membrane. Dev. Cell 7, 61-71 (2004).

34. Altmann, K. & Westermann, B. Role of essential genes in mitochondrial morphogenesis in *Saccharomyces cerevisiae*. Mol. Biol. Cell 16, 5410-5417 (2005).

35. Milnerwood, A. J. & Raymond, L. A. Early synaptic pathophysiology in neurodegeneration: insights from Huntington's disease. Trends Neurosci. 33, 513-523 (2010).

36. Johri, A. & Beal, M. F. Antioxidants in Huntington's disease. Biochim. Biophys. Acta 1822, 664-674 (2012).

37. Devi, L., Prabhu, B. M., Galati, D. F., Avadhani, N. G. & Anandatheerthavarada, H. K. Accumulation of amyloid precursor protein in the mitochondrial import channels of human Alzheimer's disease brain is associated with mitochondrial dysfunction. J. Neurosci. 26, 9057-9068 (2006).

38. Li, Q. et al. ALS-linked mutant superoxide dismutase 1 (SOD1) alters mitochondrial protein composition and decreases protein import. Proc. Natl. Acad. Sci. USA 107, 21146-21151 (2010).

39. Liu, J. et al. Toxicity of familial ALS-linked SOD1 mutants from selective recruitment to spinal mitochondria. Neuron 43, 5-17 (2004).

40. Roesch, K., Curran, S. P., Tranebjaerg, L. & Koehler, C. M. Human deafness dystonia syndrome is caused by a defect in assembly of the DDP1/TIMM8a-TIMM13 complex. Hum. Mol. Genet. 11, 477-486 (2002).

41. Ahting, U. et al. Neurological phenotype and reduced lifespan in heterozygous Tim23 knockout mice, the first mouse model of defective mitochondrial import. Biochim. Biophys. Acta 1787, 371-376 (2009).

42. Vögtle, F. N. & Meisinger, C. Sensing mitochondrial homeostasis: the protein import machinery takes control. Dev. Cell 23, 234-236 (2012).

43. Shao, J. & Diamond, M. I. Polyglutamine diseases: emerging concepts in pathogenesis and therapy. Hum. Mol. Genet. 16, R115-R123 (2007).

44. Zoghbi, H. Y. & Orr, H. T. Glutamine repeats and neurodegeneration. Annu. Rev. Neurosci. 23, 217-247 (2000).

45. Cui, L. et al. Transcriptional repression of PGC-1alpha by mutant huntingtin leads to mitochondrial dysfunction and neurodegeneration. Cell 127, 59-69 (2006).

46. Weydt, P. et al. Thermoregulatory and metabolic defects in Huntington's disease transgenic mice implicate PGC-1alpha in Huntington's disease neurodegeneration. Cell Metab. 4, 349-362 (2006).

47. Humphries, A. D. et al. Dissection of the mitochondrial import and assembly pathway for human Tom40. J. Biol. Chem. 280, 11535-11543 (2005).

48. Trettel, F. et al. Dominant phenotypes produced by the HD mutation in STHdhQ111 striatal cells. Hum. Mol. Genet. 9, 2799-2809 (2000).

49. Ehrlich, M. E. et al. ST14A cells have properties of a medium-size spiny neuron. Exp. Neurol. 167, 215-226 (2001).

50. Kristian, T. Isolation of mitochondria from the CNS. Curr. Protoc. Neurosci. 7, 7.22 (2010).

51. Baranov, S. V., Stavrovskaya, I. G., Brown, A. M., Tyryshkin, A. M. & Kristal, B. S. Kinetic model for Ca2+-induced permeability transition in energized liver mitochondria discriminates between inhibitor mechanisms. J. Biol. Chem. 283, 665-676 (2008).

52. Yano, M., Hoogenraad, N., Terada, K. & Mori, M. Identification and functional analysis of human Tom22 for protein import into mitochondria. Mol. Cell. Biol. 20, 7205-7213 (2000).

53. Terada, K. et al. Participation of the import receptor Tom20 in protein import into mammalian mitochondria: analyses in vitro and in cultured cells. FEBS Lett. 403, 309-312 (1997).

54. Kim, A. H. et al. A centrosomal Cdc20-APC pathway controls dendrite morphogenesis in postmitotic neurons. Cell 136, 322-336 (2009).

55. Yano et al., Inhibition of mitochondrial protein import by mutant huntingtin. Nat Neurosci. 2014 June; 17(6):822-31. doi: 10.1038/nn.3721. Epub 2014 May 18.

Although the presently disclosed subject matter and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Various patents, patent applications, publications, product descriptions, protocols, and sequence accession numbers are cited throughout this application, the disclosures of which are incorporated herein by reference in their entireties for all purposes.

What is claimed is:

1. A method for attenuating a mitochondrial protein import defect in a subject, comprising administering to the subject an effective amount of an agent that comprises:
   (a) an exogenous TIM23 complex protein consisting essentially of the translocase of inner mitochondrial membrane 23 (Tim23) subunit, translocase of inner mitochondrial membrane 50 (Tim50) subunit, and translocase of inner mitochondrial membrane 17a (Tim17a) subunit; or
   (b) a nucleic acid molecule encoding the subunits Tim23, Tim50, and Tim17a.

2. The method of claim 1, wherein the nucleic acid molecule is operably linked to a promoter that is constitutively active or inducible in the subject, and wherein the promoter is a PGK promoter.

3. The method of claim 1, wherein the nucleic acid molecule is administered to the subject via a vector.

4. The method of claim 1, wherein the subject is a human subject.

5. The method of claim 1, wherein the subject has Huntington's Disease.

6. A method for attenuating a mitochondrial protein import defect in a neuron, comprising:
   (a) contacting the neuron with an effective amount of an exogenous TIM23 complex protein that consists essentially of the translocase of inner mitochondrial membrane 23 (Tim23) subunit, translocase of inner mitochondrial membrane 50 (Tim50) subunit, and translocase of inner mitochondrial membrane 17a (Tim17a) subunit; or
   (b) introducing into the neuron a nucleic acid molecule encoding the subunits Tim23, Tim50, and Tim17a.

7. The method of claim 6, wherein the nucleic acid molecule is operably linked to a promoter that is constitutively active or inducible in the neuron, and wherein the promoter is a PGK promoter.

8. The method of claim 6, wherein the nucleic acid molecule is introduced into the neuron via a vector.

9. The method of claim 6, wherein the neuron is a human neuron.

10. The method of claim 6, wherein the neuron locates in vivo in a human subject.

11. The method of claim 10, wherein the human subject has Huntington's Disease.

12. The method of claim 10, the human subject is genetically susceptible to Huntington's Disease.

13. The method of claim 10, the human subject has a family member who has Huntington's Disease.

* * * * *

SEQUENCE LISTING

<160> NUMBER OF SEQ ID NOS: 13

<210> SEQ ID NO 1
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 1
cggctgaggc agcagcggct gt                                        22

<210> SEQ ID NO 2
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 2
gcagcagcag cagcaacagc cgccaccgcc                                30

<210> SEQ ID NO 3
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 3
atgaaggcct tcgagtccct caagtccttc                                30

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
ggcggctgag gaagctgagg a                                         21

<210> SEQ ID NO 5
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 5
cggaggaagt agcaacaaa                                            19

<210> SEQ ID NO 6
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 6
ggagtgccac cggaagtgca a                                         21

<210> SEQ ID NO 7
<211> LENGTH: 21
<212> TYPE: DNA
<213> ORGANISM: Artificial sequence

```
<220> FEATURE:
<223> OTHER INFORMATION: Synthetic oligonucleotide

<400> SEQUENCE: 7
gctgagtccc acagaggcgt t                                              21

<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 8
ggcactgtca tgtctctagc t                                              21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
gctgtgacaa agatcatgga t                                              21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
gcctggtcca aaccaagaaa t                                              21

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
cggtcttcgt ttaggattga a                                              21

<210> SEQ ID NO 12
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 12
ctgatgaagg ccttcgagga actcaaggaa ttccagcagc a                        41

<210> SEQ ID NO 13
<211> LENGTH: 41
<212> TYPE: DNA
<213> ORGANISM: Artificial sequence
<220> FEATURE:
<223> OTHER INFORMATION: Synthetic oligonucleotide

<400> SEQUENCE: 13
ctgctgctgg aattccttga gttcctcgaa ggccttcatc a                        41
```